(12) United States Patent
Hayes et al.

(10) Patent No.: US 12,295,865 B2
(45) Date of Patent: May 13, 2025

(54) EXPANDABLE INTERBODY IMPLANT AND CORRESPONDING INSERTER

(71) Applicant: Warsaw Orthopedic, Inc., Warsaw, IN (US)

(72) Inventors: Stanley K. Hayes, Mission Viejo, CA (US); Charlie J. Barfield, East Hernando, MS (US); Dimitri K. Protopsaltis, Memphis, TN (US); Robert M. Loke, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 727 days.

(21) Appl. No.: 17/515,709

(22) Filed: Nov. 1, 2021

(65) Prior Publication Data

US 2022/0409397 A1 Dec. 29, 2022

Related U.S. Application Data

(63) Continuation-in-part of application No. 17/356,950, filed on Jun. 24, 2021, now Pat. No. 11,612,499.

(51) Int. Cl.
*A61F 2/44* (2006.01)
*A61F 2/30* (2006.01)
*A61F 2/46* (2006.01)

(52) U.S. Cl.
CPC ........ *A61F 2/4611* (2013.01); *A61F 2/30749* (2013.01); *A61F 2/442* (2013.01);
(Continued)

(58) Field of Classification Search
CPC ........ A61F 2/447; A61F 2/442; A61F 2/4455; A61F 2002/30331; A61F 2002/30405;
(Continued)

(56) References Cited

U.S. PATENT DOCUMENTS 1,677,337 A 7/1928 Grove
3,847,154 A 11/1974 Nordin
(Continued)

FOREIGN PATENT DOCUMENTS

CN 107 137 166 A 9/2017
DE 44 16 605 C1 6/1995
(Continued)

OTHER PUBLICATIONS

International Search Report and Written Opinion in Application No. PCT/US2022/030094 dated Sep. 16, 2022.
(Continued)

*Primary Examiner* — Jessica Weiss
(74) *Attorney, Agent, or Firm* — FOX ROTHSCHILD LLP

(57) ABSTRACT

An expandable implant may include an expandable body defined by a superior endplate and an inferior endplate that are hingedly coupled and may be expanded and lordosed by an external surgical tool. The superior endplate may include a first core having a distal engagement surface and the inferior endplate may a second core having a proximal engagement surface and a threaded screw aperture. The implant may include a threaded locking screw disposed in the threaded screw aperture and movable between a locked position and an unlocked position, for example. In the locked position, the threaded locking screw may urge the distal engagement surface of the first core into direct contact with the proximal engagement surface of the second core. The implant may include a pair of mounting tangs that may be sheared off and/or recesses. The locking screw may be a break-off screw.

20 Claims, 30 Drawing Sheets

(52) U.S. Cl.
CPC ..... *A61F 2/447* (2013.01); *A61F 2002/30112* (2013.01); *A61F 2002/30383* (2013.01); *A61F 2002/30405* (2013.01); *A61F 2002/30507* (2013.01); *A61F 2002/30561* (2013.01); *A61F 2002/30579* (2013.01); *A61F 2002/4627* (2013.01)

(58) Field of Classification Search
CPC .. A61F 2002/30428; A61F 2002/30471; A61F 2002/30507; A61F 2250/0071; A61F 2002/30564
USPC ........ 623/17.11–17.16; 606/70–71, 280–299
See application file for complete search history.

(56) References Cited

U.S. PATENT DOCUMENTS

| | | | |
|---|---|---|---|
| 4,401,112 A | 8/1983 | Rezaian | |
| 4,553,273 A | 11/1985 | Wu | |
| 4,636,217 A | 1/1987 | Ogilvie et al. | |
| 4,716,894 A | 1/1988 | Lazzeri et al. | |
| 4,759,769 A | 7/1988 | Hedman et al. | |
| 5,059,193 A | 10/1991 | Kuslich | |
| 5,171,278 A | 12/1992 | Pisharodi | |
| 5,228,811 A | 7/1993 | Potter | |
| 5,284,483 A | 2/1994 | Johnson et al. | |
| 5,336,223 A | 8/1994 | Rogers | |
| 5,390,683 A | 2/1995 | Pisharodi | |
| 5,522,899 A | 6/1996 | Michelson | |
| 5,554,191 A | 9/1996 | Lahille et al. | |
| 5,575,790 A | 11/1996 | Chen et al. | |
| 5,609,635 A | 3/1997 | Michelson | |
| 5,653,762 A | 8/1997 | Pisharodi | |
| 5,653,763 A | 8/1997 | Errico et al. | |
| 5,658,336 A | 8/1997 | Pisharodi | |
| 5,665,122 A | 9/1997 | Kambin | |
| 5,693,100 A | 12/1997 | Pisharodi | |
| 5,697,977 A | 12/1997 | Pisharodi | |
| 5,702,391 A | 12/1997 | Lin | |
| 5,702,453 A | 12/1997 | Rabbe et al. | |
| 5,702,455 A | 12/1997 | Saggar | |
| 5,797,918 A | 8/1998 | McGuire et al. | |
| 5,800,550 A | 9/1998 | Sertich | |
| 5,865,848 A | 2/1999 | Baker | |
| 5,893,890 A | 4/1999 | Pisharodi | |
| 5,931,777 A | 8/1999 | Sava | |
| 5,941,885 A | 8/1999 | Jackson | |
| 5,971,987 A | 10/1999 | Huxel et al. | |
| 5,980,522 A | 11/1999 | Koros et al. | |
| 6,045,579 A | 4/2000 | Hochshuler et al. | |
| 6,074,343 A | 6/2000 | Nathanson et al. | |
| 6,080,193 A | 6/2000 | Hochshuler et al. | |
| 6,099,531 A | 8/2000 | Bonutti | |
| 6,102,949 A | 8/2000 | Biedermann et al. | |
| 6,102,950 A | 8/2000 | Vaccaro | |
| 6,106,557 A | 8/2000 | Robioneck et al. | |
| 6,113,638 A | 9/2000 | Williams et al. | |
| 6,117,174 A | 9/2000 | Nolan | |
| 6,132,465 A | 10/2000 | Ray et al. | |
| 6,159,211 A | 12/2000 | Boriani et al. | |
| 6,159,244 A | 12/2000 | Suddaby | |
| 6,176,882 B1 | 1/2001 | Biedermann et al. | |
| 6,179,873 B1 | 1/2001 | Zientek | |
| 6,190,414 B1 | 2/2001 | Young et al. | |
| 6,193,757 B1 | 2/2001 | Foley et al. | |
| 6,217,579 B1 | 4/2001 | Koros | |
| 6,245,108 B1 | 6/2001 | Biscup | |
| 6,309,421 B1 | 10/2001 | Pisharodi | |
| 6,342,074 B1 | 1/2002 | Simpson | |
| 6,371,989 B1 | 4/2002 | Chauvin et al. | |
| 6,395,031 B1 | 5/2002 | Foley et al. | |
| 6,423,063 B1 | 7/2002 | Bonutti | |
| 6,432,106 B1 | 8/2002 | Fraser | |
| 6,436,140 B1 | 8/2002 | Liu et al. | |
| 6,443,989 B1 | 9/2002 | Jackson | |
| 6,443,990 B1 | 9/2002 | Aebi et al. | |
| 6,454,806 B1 | 9/2002 | Cohen et al. | |
| 6,454,807 B1 | 9/2002 | Jackson | |
| 6,461,359 B1 | 10/2002 | Tribus et al. | |
| 6,475,218 B2 * | 11/2002 | Gournay ............ A61B 17/7034 606/272 |
| 6,491,724 B1 | 12/2002 | Ferree | |
| 6,520,991 B2 | 2/2003 | Huene | |
| 6,520,993 B2 | 2/2003 | James et al. | |
| 6,524,238 B2 | 2/2003 | Velikaris et al. | |
| 6,527,803 B1 | 3/2003 | Crozet et al. | |
| 6,562,074 B2 | 5/2003 | Gerbec et al. | |
| 6,576,016 B1 | 6/2003 | Hochshuler et al. | |
| 6,623,525 B2 | 9/2003 | Ralph et al. | |
| 6,629,998 B1 | 10/2003 | Lin | |
| 6,635,086 B2 | 10/2003 | Lin | |
| 6,648,917 B2 | 11/2003 | Gerbec et al. | |
| 6,676,703 B2 | 1/2004 | Biscup | |
| 6,685,742 B1 | 2/2004 | Jackson | |
| 6,723,126 B1 | 4/2004 | Berry | |
| 6,770,096 B2 | 8/2004 | Bolger et al. | |
| 6,773,460 B2 | 8/2004 | Jackson | |
| 6,821,298 B1 | 11/2004 | Jackson | |
| 6,835,206 B2 | 12/2004 | Jackson | |
| 6,849,093 B2 | 2/2005 | Michelson | |
| 6,852,129 B2 | 2/2005 | Gerbec et al. | |
| 6,863,673 B2 | 3/2005 | Gerbec et al. | |
| 6,923,814 B1 | 8/2005 | Hildebrand et al. | |
| 6,926,737 B2 | 8/2005 | Jackson | |
| 6,953,477 B2 | 10/2005 | Berry | |
| 6,964,687 B1 | 11/2005 | Bernard et al. | |
| 6,974,480 B2 | 12/2005 | Messerli et al. | |
| 6,984,234 B2 | 1/2006 | Bray | |
| 7,112,222 B2 | 9/2006 | Fraser et al. | |
| 7,135,043 B2 | 11/2006 | Nakahara et al. | |
| 7,137,997 B2 | 11/2006 | Paul | |
| 7,172,627 B2 | 2/2007 | Fiere et al. | |
| 7,188,626 B2 | 3/2007 | Foley et al. | |
| 7,204,853 B2 | 4/2007 | Gordon et al. | |
| 7,232,464 B2 | 6/2007 | Mathieu et al. | |
| 7,238,203 B2 | 7/2007 | Bagga et al. | |
| 7,255,700 B2 | 8/2007 | Kaiser et al. | |
| 7,316,532 B2 | 1/2008 | Matthys-Mark | |
| 7,316,714 B2 | 1/2008 | Gordon et al. | |
| 7,407,483 B2 | 8/2008 | Perez-Cruet et al. | |
| 7,481,766 B2 | 1/2009 | Lee et al. | |
| 7,491,168 B2 | 2/2009 | Raymond et al. | |
| 7,537,565 B2 | 5/2009 | Bass | |
| 7,618,456 B2 | 11/2009 | Mathieu et al. | |
| 7,625,394 B2 | 12/2009 | Molz, IV et al. | |
| 7,635,366 B2 | 12/2009 | Abdou | |
| 7,637,909 B2 | 12/2009 | Lechot et al. | |
| 7,655,046 B2 | 2/2010 | Dryer et al. | |
| 7,678,148 B2 | 3/2010 | Peterman | |
| 7,703,727 B2 | 4/2010 | Selness | |
| 7,708,778 B2 | 5/2010 | Gordon et al. | |
| 7,708,779 B2 | 5/2010 | Edie et al. | |
| 7,727,280 B2 | 6/2010 | McLuen | |
| 7,753,958 B2 | 7/2010 | Gordon et al. | |
| 7,780,594 B2 | 8/2010 | Hutton | |
| 7,806,932 B2 | 10/2010 | Webb et al. | |
| 7,815,682 B1 | 10/2010 | Peterson et al. | |
| 7,819,801 B2 | 10/2010 | Miles et al. | |
| 7,824,428 B2 | 11/2010 | Mikkonen et al. | |
| 7,828,849 B2 | 11/2010 | Lim | |
| 7,846,167 B2 | 12/2010 | Garcia et al. | |
| 7,846,207 B2 | 12/2010 | Lechmann et al. | |
| 7,850,731 B2 | 12/2010 | Brittan et al. | |
| 7,850,733 B2 | 12/2010 | Baynham et al. | |
| 7,862,616 B2 | 1/2011 | Lechmann et al. | |
| 7,875,076 B2 | 1/2011 | Mathieu et al. | |
| 7,883,542 B2 | 2/2011 | Zipnick | |
| 7,892,173 B2 | 2/2011 | Miles et al. | |
| 7,909,869 B2 | 3/2011 | Gordon et al. | |
| 7,914,559 B2 | 3/2011 | Carls et al. | |
| 7,967,821 B2 | 6/2011 | Sicvol et al. | |
| 7,981,031 B2 | 7/2011 | Frasier et al. | |
| 8,016,836 B2 | 9/2011 | Corrao et al. | |
| 8,062,375 B2 | 11/2011 | Glerum et al. | |

(56) References Cited

U.S. PATENT DOCUMENTS

| | | |
|---|---|---|
| 8,105,382 B2 | 1/2012 | Olmos et al. |
| 8,118,870 B2 | 2/2012 | Gordon et al. |
| 8,118,871 B2 | 2/2012 | Gordon et al. |
| 8,123,810 B2 | 2/2012 | Gordon et al. |
| 8,147,550 B2 | 4/2012 | Gordon et al. |
| 8,172,903 B2 | 5/2012 | Gordon et al. |
| 8,182,539 B2 | 5/2012 | Tyber et al. |
| 8,257,442 B2 | 9/2012 | Edie et al. |
| 8,262,570 B2 | 9/2012 | White et al. |
| 8,262,662 B2 | 9/2012 | Beardsley et al. |
| 8,262,710 B2 | 9/2012 | Freedman et al. |
| 8,287,597 B1 | 10/2012 | Pimenta et al. |
| 8,303,498 B2 | 11/2012 | Miles et al. |
| 8,303,658 B2 | 11/2012 | Peterman |
| 8,303,663 B2 | 11/2012 | Jimenez et al. |
| 8,317,866 B2 | 11/2012 | Palmatier et al. |
| 8,323,185 B2 | 12/2012 | Perez-Cruet et al. |
| 8,328,872 B2 | 12/2012 | Duffield et al. |
| 8,343,048 B2 | 1/2013 | Warren, Jr. |
| 8,353,826 B2 | 1/2013 | Weiman |
| 8,355,780 B2 | 1/2013 | Miles et al. |
| 8,382,842 B2 | 2/2013 | Greenhalgh et al. |
| 8,388,527 B2 | 3/2013 | Miles et al. |
| 8,398,713 B2 | 3/2013 | Weiman |
| 8,403,990 B2 | 3/2013 | Dryer et al. |
| 8,419,797 B2 | 4/2013 | Biedermann et al. |
| 8,425,528 B2 | 4/2013 | Berry et al. |
| 8,435,298 B2 | 5/2013 | Weiman |
| 8,480,576 B2 | 7/2013 | Sandhu |
| 8,496,706 B2 | 7/2013 | Ragab et al. |
| 8,500,634 B2 | 8/2013 | Miles et al. |
| 8,506,635 B2 | 8/2013 | Palmatier et al. |
| 8,517,935 B2 | 8/2013 | Marchek et al. |
| 8,518,120 B2 | 8/2013 | Glerum et al. |
| 8,535,380 B2 | 9/2013 | Greenhalgh et al. |
| 8,550,994 B2 | 10/2013 | Miles et al. |
| 8,556,808 B2 | 10/2013 | Miles et al. |
| 8,556,979 B2 | 10/2013 | Glerum et al. |
| 8,579,809 B2 | 11/2013 | Parker |
| 8,579,898 B2 | 11/2013 | Prandi et al. |
| 8,579,979 B2 | 11/2013 | Edie et al. |
| 8,579,981 B2 | 11/2013 | Lim et al. |
| 8,602,984 B2 | 12/2013 | Raymond et al. |
| 8,608,785 B2 | 12/2013 | Reed et al. |
| 8,628,576 B2 | 1/2014 | Triplett et al. |
| 8,628,578 B2 | 1/2014 | Miller et al. |
| 8,632,595 B2 | 1/2014 | Weiman |
| 8,641,768 B2 | 2/2014 | Duffield et al. |
| 8,647,386 B2 | 2/2014 | Gordon et al. |
| 8,663,329 B2 | 3/2014 | Ernst |
| 8,668,419 B2 | 3/2014 | Hardt et al. |
| 8,668,715 B2 | 3/2014 | Sandhu |
| 8,679,183 B2 | 3/2014 | Glerum et al. |
| 8,685,095 B2 * | 4/2014 | Miller ............... A61F 2/4611 623/17.11 |
| 8,685,098 B2 | 4/2014 | Glerum et al. |
| 8,696,559 B2 | 4/2014 | Miles et al. |
| 8,709,083 B2 | 4/2014 | Duffield et al. |
| 8,709,085 B2 | 4/2014 | Lechmann et al. |
| 8,709,086 B2 | 4/2014 | Glerum |
| 8,715,285 B2 | 5/2014 | Lewis et al. |
| 8,715,353 B2 | 5/2014 | Bagga et al. |
| 8,740,983 B1 | 6/2014 | Arnold et al. |
| 8,753,271 B1 | 6/2014 | Miles et al. |
| 8,753,396 B1 | 6/2014 | Hockett et al. |
| 8,764,649 B2 | 7/2014 | Miles et al. |
| 8,771,360 B2 | 7/2014 | Jimenez et al. |
| 8,778,025 B2 | 7/2014 | Ragab et al. |
| 8,778,027 B2 | 7/2014 | Medina |
| 8,795,366 B2 | 8/2014 | Varela |
| 8,808,305 B2 | 8/2014 | Kleiner |
| 8,827,902 B2 | 9/2014 | Dietze, Jr. et al. |
| 8,828,085 B1 | 9/2014 | Jensen |
| 8,840,668 B1 | 9/2014 | Donahoe et al. |
| 8,845,731 B2 | 9/2014 | Weiman |
| 8,845,732 B2 | 9/2014 | Weiman |
| 8,845,734 B2 | 9/2014 | Weiman |
| 8,852,252 B2 | 10/2014 | Venturini et al. |
| 8,852,282 B2 | 10/2014 | Farley et al. |
| 8,864,833 B2 | 10/2014 | Glerum et al. |
| 8,882,813 B2 | 11/2014 | Jones et al. |
| 8,888,853 B2 | 11/2014 | Glerum et al. |
| 8,894,708 B2 | 11/2014 | Thalgott et al. |
| 8,894,711 B2 | 11/2014 | Varela |
| 8,894,712 B2 | 11/2014 | Varela |
| 8,906,095 B2 | 12/2014 | Christensen et al. |
| 8,920,500 B1 | 12/2014 | Pimenta et al. |
| 8,926,704 B2 | 1/2015 | Glerum et al. |
| 8,936,641 B2 | 1/2015 | Cain |
| 8,940,049 B1 | 1/2015 | Jimenez et al. |
| 8,968,363 B2 | 3/2015 | Weiman et al. |
| 8,986,344 B2 | 3/2015 | Sandhu |
| 8,992,425 B2 | 3/2015 | Karpowicz et al. |
| 8,992,544 B2 | 3/2015 | Sasing |
| 9,005,292 B2 | 4/2015 | Melamed |
| 9,005,293 B2 | 4/2015 | Moskowitz et al. |
| 9,005,295 B2 | 4/2015 | Kueenzi et al. |
| 9,017,412 B2 | 4/2015 | Wolters et al. |
| 9,034,045 B2 | 5/2015 | Davenport et al. |
| 9,050,146 B2 | 6/2015 | Woolley et al. |
| 9,050,194 B2 | 6/2015 | Thibodeau |
| 9,060,877 B2 | 6/2015 | Kleiner |
| 9,072,548 B2 | 7/2015 | Matityahu |
| 9,072,563 B2 | 7/2015 | Garcia et al. |
| 9,084,591 B2 | 7/2015 | Reglos et al. |
| 9,113,854 B2 | 8/2015 | Ellman |
| 9,119,730 B2 | 9/2015 | Glerum et al. |
| 9,125,757 B2 | 9/2015 | Weiman |
| 9,132,021 B2 | 9/2015 | Mermuys et al. |
| 9,138,217 B2 | 9/2015 | Smith et al. |
| 9,138,330 B2 | 9/2015 | Hansell et al. |
| 9,138,331 B2 | 9/2015 | Aferzon |
| 9,149,367 B2 | 10/2015 | Davenport et al. |
| 9,155,628 B2 | 10/2015 | Glerum et al. |
| 9,155,631 B2 | 10/2015 | Seifert et al. |
| 9,161,841 B2 | 10/2015 | Kana et al. |
| 9,179,903 B2 | 11/2015 | Cianfrani et al. |
| 9,179,952 B2 | 11/2015 | Biedermann et al. |
| 9,186,193 B2 | 11/2015 | Kleiner et al. |
| 9,186,258 B2 | 11/2015 | Davenport et al. |
| 9,192,482 B1 | 11/2015 | Pimenta et al. |
| 9,192,483 B1 | 11/2015 | Radcliffe et al. |
| 9,198,772 B2 | 12/2015 | Weiman |
| 9,204,972 B2 | 12/2015 | Weiman et al. |
| 9,204,974 B2 | 12/2015 | Glerum et al. |
| 9,211,194 B2 | 12/2015 | Bagga et al. |
| 9,211,196 B2 | 12/2015 | Glerum et al. |
| 9,216,095 B2 | 12/2015 | Glerum et al. |
| 9,226,836 B2 | 1/2016 | Glerum |
| 9,233,007 B2 | 1/2016 | Sungarian et al. |
| 9,233,009 B2 | 1/2016 | Gray et al. |
| 9,233,010 B2 | 1/2016 | Thalgott et al. |
| 9,259,327 B2 | 2/2016 | Niemiec et al. |
| 9,271,846 B2 | 3/2016 | Lim et al. |
| 9,308,099 B2 | 4/2016 | Triplett et al. |
| 9,320,610 B2 | 4/2016 | Alheidt et al. |
| 9,351,845 B1 | 5/2016 | Pimenta et al. |
| 9,351,848 B2 | 5/2016 | Glerum et al. |
| 9,357,909 B2 | 6/2016 | Perez-Cruet et al. |
| 9,358,126 B2 | 6/2016 | Glerum et al. |
| 9,358,127 B2 | 6/2016 | Duffield et al. |
| 9,358,128 B2 | 6/2016 | Glerum et al. |
| 9,358,129 B2 | 6/2016 | Weiman |
| 9,364,341 B2 | 6/2016 | Gowan |
| 9,364,343 B2 | 6/2016 | Duffield et al. |
| 9,370,434 B2 | 6/2016 | Weiman |
| 9,370,435 B2 | 6/2016 | Walkenhorst et al. |
| 9,381,008 B2 | 7/2016 | Thornburg |
| 9,386,916 B2 | 7/2016 | Predick et al. |
| 9,387,092 B2 | 7/2016 | Mermuys et al. |
| 9,402,673 B2 | 8/2016 | Cormier et al. |
| 9,402,739 B2 | 8/2016 | Weiman et al. |
| 9,408,596 B2 | 8/2016 | Blain |
| 9,408,708 B2 | 8/2016 | Greenhalgh |

(56) References Cited

U.S. PATENT DOCUMENTS

| | | |
|---|---|---|
| 9,414,828 B2 | 8/2016 | Abidin et al. |
| 9,414,934 B2 | 8/2016 | Cain |
| 9,414,937 B2 | 8/2016 | Carlson et al. |
| 9,421,110 B2 | 8/2016 | Masson et al. |
| 9,427,331 B2 | 8/2016 | Amin |
| 9,445,919 B2 | 9/2016 | Palmatier et al. |
| 9,452,063 B2 | 9/2016 | Glerum et al. |
| 9,456,903 B2 | 10/2016 | Glerum et al. |
| 9,456,906 B2 | 10/2016 | Gray et al. |
| 9,468,405 B2 | 10/2016 | Miles et al. |
| 9,474,622 B2 | 10/2016 | McLaughlin et al. |
| 9,474,625 B2 | 10/2016 | Weiman |
| 9,480,573 B2 | 11/2016 | Perloff et al. |
| 9,480,576 B2 | 11/2016 | Pepper et al. |
| 9,480,579 B2 | 11/2016 | Davenport et al. |
| 9,486,133 B2 | 11/2016 | Lee et al. |
| 9,486,325 B2 | 11/2016 | Davenport et al. |
| 9,486,327 B2 | 11/2016 | Martynova et al. |
| 9,486,328 B2 | 11/2016 | Jimenez et al. |
| 9,492,287 B2 | 11/2016 | Glerum et al. |
| 9,492,288 B2 | 11/2016 | Wagner et al. |
| 9,492,289 B2 | 11/2016 | Davenport et al. |
| 9,498,349 B2 | 11/2016 | Patterson et al. |
| 9,510,954 B2 | 12/2016 | Glerum et al. |
| 9,517,098 B2 | 12/2016 | Anderson |
| 9,522,070 B2 | 12/2016 | Flower et al. |
| 9,526,620 B2 | 12/2016 | Slivka et al. |
| 9,526,625 B2 | 12/2016 | Cain |
| 9,532,821 B2 | 1/2017 | Moskowitz et al. |
| 9,539,103 B2 | 1/2017 | McLaughlin et al. |
| 9,539,108 B2 | 1/2017 | Glerum et al. |
| 9,545,320 B2 | 1/2017 | Padovani et al. |
| 9,549,723 B2 | 1/2017 | Hynes et al. |
| 9,549,824 B2 | 1/2017 | McAfee |
| 9,561,116 B2 | 2/2017 | Weiman et al. |
| 9,566,163 B2 | 2/2017 | Suddaby et al. |
| 9,566,166 B2 | 2/2017 | Parry et al. |
| 9,566,168 B2 | 2/2017 | Glerum et al. |
| 9,572,560 B2 | 2/2017 | Mast et al. |
| 9,572,677 B2 | 2/2017 | Davenport et al. |
| 9,572,681 B2 | 2/2017 | Mathieu et al. |
| 9,579,124 B2 | 2/2017 | Gordon et al. |
| 9,579,139 B2 | 2/2017 | Cormier et al. |
| 9,579,213 B2 | 2/2017 | Bal et al. |
| 9,585,649 B2 | 3/2017 | Blain et al. |
| 9,585,762 B2 | 3/2017 | Suddaby et al. |
| 9,585,766 B2 | 3/2017 | Robinson |
| 9,585,767 B2 | 3/2017 | Robinson |
| 9,592,129 B2 | 3/2017 | Slivka et al. |
| 9,597,195 B2 | 3/2017 | Cain |
| 9,603,643 B2 | 3/2017 | Reed et al. |
| 9,603,713 B2 | 3/2017 | Moskowitz et al. |
| 9,603,717 B2 | 3/2017 | Ibarra et al. |
| 9,615,818 B2 | 4/2017 | Baudouin et al. |
| 9,615,936 B2 | 4/2017 | Duffield et al. |
| 9,622,732 B2 | 4/2017 | Martinelli et al. |
| 9,622,875 B2 | 4/2017 | Moskowitz et al. |
| 9,622,876 B1 | 4/2017 | Greenhalgh et al. |
| 9,629,729 B2 | 4/2017 | Grimberg, Jr. et al. |
| 9,636,097 B2 | 5/2017 | Bass |
| 9,642,720 B2 | 5/2017 | Radcliffe et al. |
| 9,649,198 B2 | 5/2017 | Wolters et al. |
| 9,655,746 B2 | 5/2017 | Seifert |
| 9,655,747 B2 | 5/2017 | Glerum et al. |
| 9,662,224 B2 | 5/2017 | Weiman et al. |
| 9,668,784 B2 | 6/2017 | Brumfield et al. |
| 9,668,876 B2 | 6/2017 | Blain et al. |
| 9,668,879 B2 | 6/2017 | Jimenez et al. |
| 9,675,465 B2 | 6/2017 | Padovani et al. |
| 9,675,467 B2 | 6/2017 | Duffield et al. |
| 9,675,468 B1 | 6/2017 | Jensen |
| 9,693,871 B2 | 7/2017 | Richerme et al. |
| 9,700,428 B2 | 7/2017 | Niemiec et al. |
| 9,707,092 B2 | 7/2017 | Davenport et al. |
| 9,713,536 B2 | 7/2017 | Foley et al. |
| 9,717,601 B2 | 8/2017 | Miller |
| 9,730,684 B2 | 8/2017 | Beale et al. |
| 9,730,806 B2 | 8/2017 | Capote |
| 9,737,288 B2 | 8/2017 | Karpowicz et al. |
| 9,750,617 B2 | 9/2017 | Lim et al. |
| 9,750,618 B1 | 9/2017 | Daffinson et al. |
| 9,757,249 B2 | 9/2017 | Radcliffe et al. |
| 9,763,722 B2 | 9/2017 | Roybal |
| 9,770,343 B2 | 9/2017 | Weiman |
| 9,782,265 B2 | 10/2017 | Weiman et al. |
| 9,788,971 B1 | 10/2017 | Stein |
| 9,795,370 B2 | 10/2017 | O'Connell et al. |
| 9,795,371 B2 | 10/2017 | Miles et al. |
| 9,801,733 B2 | 10/2017 | Wolters et al. |
| 9,801,734 B1 | 10/2017 | Stein et al. |
| 9,808,352 B2 | 11/2017 | Suddaby et al. |
| 9,826,966 B2 | 11/2017 | Mast et al. |
| 9,827,024 B2 | 11/2017 | Cormier et al. |
| 9,827,107 B1 | 11/2017 | Amin |
| 9,833,333 B2 | 12/2017 | Duffield et al. |
| 9,833,336 B2 | 12/2017 | Davenport et al. |
| 9,839,527 B2 | 12/2017 | Robinson |
| 9,839,528 B2 | 12/2017 | Weiman et al. |
| 9,848,993 B2 | 12/2017 | Moskowitz et al. |
| 9,848,996 B2 | 12/2017 | Faulhaber |
| 9,855,151 B2 | 1/2018 | Weiman |
| 9,867,715 B2 | 1/2018 | McLaughlin et al. |
| 9,872,779 B2 | 1/2018 | Miller et al. |
| 9,889,019 B2 | 2/2018 | Rogers et al. |
| 9,907,671 B2 | 3/2018 | Fessler |
| 9,907,673 B2 | 3/2018 | Weiman et al. |
| 9,918,709 B2 | 3/2018 | Sandhu |
| 9,924,859 B2 | 3/2018 | Lee et al. |
| 9,924,940 B2 | 3/2018 | Moskowitz et al. |
| 9,925,062 B2 | 3/2018 | Glerum et al. |
| 9,925,064 B2 | 3/2018 | Duffield et al. |
| 9,931,223 B2 | 4/2018 | Cain |
| 9,937,053 B2 | 4/2018 | Melkent et al. |
| 9,937,060 B2 | 4/2018 | Fuhrer et al. |
| 9,943,342 B2 | 4/2018 | Tanaka et al. |
| 9,943,418 B2 | 4/2018 | Davenport et al. |
| 9,949,775 B2 | 4/2018 | Reed et al. |
| 9,949,841 B2 | 4/2018 | Glerum et al. |
| 9,956,087 B2 | 5/2018 | Seifert et al. |
| 9,962,202 B2 | 5/2018 | Anderson |
| 9,962,270 B2 | 5/2018 | Alheidt et al. |
| 9,962,271 B2 | 5/2018 | Glerum |
| 9,962,272 B1 | 5/2018 | Daffinson et al. |
| 9,968,461 B2 | 5/2018 | Zappacosta et al. |
| 9,968,462 B2 | 5/2018 | Weiman |
| 9,974,531 B2 | 5/2018 | Miles et al. |
| 9,974,662 B2 | 5/2018 | Hessler et al. |
| 9,974,664 B2 | 5/2018 | Emerick et al. |
| 9,980,825 B2 | 5/2018 | Nichols et al. |
| 9,980,826 B2 | 5/2018 | Martynova et al. |
| 9,987,141 B2 | 6/2018 | Duffield et al. |
| 9,987,143 B2 | 6/2018 | Robinson et al. |
| 9,987,144 B2 | 6/2018 | Seifert et al. |
| 9,987,146 B1 | 6/2018 | Lentner et al. |
| 9,993,239 B2 | 6/2018 | Karpowicz et al. |
| 9,993,350 B2 | 6/2018 | Cain |
| 10,004,607 B2 | 6/2018 | Weiman et al. |
| 10,004,608 B2 * | 6/2018 | Carnes ................. A61F 2/4455 |
| 10,016,282 B2 | 7/2018 | Seifert et al. |
| 10,016,284 B2 | 7/2018 | Moskowitz et al. |
| 10,022,239 B1 | 7/2018 | Lentner et al. |
| 10,028,842 B2 | 7/2018 | Gray et al. |
| 10,034,765 B2 | 7/2018 | Blain et al. |
| 10,034,769 B2 | 7/2018 | Baynham |
| 10,034,771 B2 | 7/2018 | Capote et al. |
| 10,034,772 B2 | 7/2018 | Glerum et al. |
| 10,034,773 B2 | 7/2018 | McLaughlin et al. |
| 10,039,539 B2 | 8/2018 | Friedrich et al. |
| 10,039,650 B2 | 8/2018 | Lamborne et al. |
| 10,052,214 B2 | 8/2018 | Jimenez et al. |
| 10,058,431 B2 | 8/2018 | Tyber et al. |
| 10,060,469 B2 | 8/2018 | Jimenez et al. |
| 10,070,852 B2 | 9/2018 | Mast et al. |
| 10,076,320 B2 | 9/2018 | Mast et al. |

(56) References Cited

U.S. PATENT DOCUMENTS

| | | |
|---|---|---|
| 10,076,423 B2 | 9/2018 | Miller et al. |
| 10,080,666 B2 | 9/2018 | Suddaby et al. |
| 10,080,669 B2 | 9/2018 | Davenport et al. |
| 10,085,846 B2 | 10/2018 | Grotz |
| 10,085,849 B2 | 10/2018 | Weiman et al. |
| 10,092,417 B2 | 10/2018 | Weiman et al. |
| 10,098,758 B2 | 10/2018 | Matthews et al. |
| 10,098,759 B2 | 10/2018 | Weiman |
| 10,111,755 B2 | 10/2018 | Foley et al. |
| 10,111,758 B2 | 10/2018 | Robinson |
| 10,117,754 B2 | 11/2018 | Davenport et al. |
| 10,117,755 B2 | 11/2018 | Emerick et al. |
| 10,137,002 B2 | 11/2018 | Padovani et al. |
| 10,137,006 B2 | 11/2018 | Dewey et al. |
| 10,137,007 B2 | 11/2018 | Dewey et al. |
| 10,137,009 B2 | 11/2018 | Weiman et al. |
| 10,149,671 B2 | 12/2018 | Predick et al. |
| 10,149,710 B2 | 12/2018 | Tanaka et al. |
| 10,154,781 B2 | 12/2018 | Weiman |
| 10,154,912 B2 | 12/2018 | Glerum |
| 10,154,914 B2 | 12/2018 | Robinson |
| 10,159,584 B2 | 12/2018 | Carnes et al. |
| 10,166,117 B1 | 1/2019 | Daffinson et al. |
| 10,172,515 B2 | 1/2019 | Lee et al. |
| 10,172,652 B2 | 1/2019 | Woolley et al. |
| 10,178,987 B2 | 1/2019 | Predick et al. |
| 10,179,053 B2 | 1/2019 | Zappacosta et al. |
| 10,182,922 B2 | 1/2019 | Nichols et al. |
| 10,188,527 B2 | 1/2019 | Rogers et al. |
| 10,195,050 B2 | 2/2019 | Palmatier et al. |
| 10,201,431 B2 | 2/2019 | Slater et al. |
| 10,213,192 B2 | 2/2019 | Capote |
| 10,213,193 B2 | 2/2019 | Karpowicz et al. |
| 10,219,798 B2 | 3/2019 | Capote |
| 10,219,913 B2 | 3/2019 | Matthews et al. |
| 10,219,914 B2 | 3/2019 | Faulhaber |
| 10,219,915 B1 | 3/2019 | Stein |
| 10,226,356 B2 | 3/2019 | Grotz |
| 10,226,359 B2 | 3/2019 | Glerum et al. |
| 10,238,375 B2 | 3/2019 | O'Connell et al. |
| 10,238,383 B2 | 3/2019 | Moskowitz et al. |
| 10,238,503 B2 | 3/2019 | Branch et al. |
| 10,245,015 B2 | 4/2019 | Predick et al. |
| 10,251,643 B2 | 4/2019 | Moskowitz et al. |
| 10,265,191 B2 | 4/2019 | Lim et al. |
| 10,278,686 B2 | 5/2019 | Baudouin et al. |
| 10,278,786 B2 | 5/2019 | Friedrich et al. |
| 10,278,830 B1 | 5/2019 | Walker et al. |
| 10,278,831 B2 | 5/2019 | Sandul |
| 10,278,832 B2 | 5/2019 | Nichols et al. |
| 10,285,680 B2 | 5/2019 | Friedrich et al. |
| 10,285,819 B2 | 5/2019 | Greenhalgh |
| 10,285,824 B2 | 5/2019 | Robinson |
| 10,292,828 B2 | 5/2019 | Greenhalgh |
| 10,299,777 B2 | 5/2019 | Mast et al. |
| 10,299,934 B2 | 5/2019 | Seifert et al. |
| 10,299,937 B2 | 5/2019 | McAfee |
| 10,307,268 B2 | 6/2019 | Moskowitz et al. |
| 10,314,622 B2 | 6/2019 | Brumfield et al. |
| 10,314,719 B2 | 6/2019 | Hessler et al. |
| 10,322,007 B2 | 6/2019 | Masson et al. |
| 10,322,009 B2 | 6/2019 | Aghayev et al. |
| 10,327,909 B2 | 6/2019 | Baynham |
| 10,327,912 B1 | 6/2019 | Suddaby |
| 10,327,917 B2 | 6/2019 | Glerum et al. |
| 10,342,675 B2 | 7/2019 | Alheidt |
| 10,350,085 B2 | 7/2019 | Glerum et al. |
| 10,357,233 B2 | 7/2019 | Miles et al. |
| 10,363,142 B2 | 7/2019 | McClintock et al. |
| 10,363,144 B2 | 7/2019 | Overes et al. |
| 10,369,004 B2 | 8/2019 | Faulhaber |
| 10,369,008 B2 | 8/2019 | Jimenez et al. |
| 10,369,010 B2 | 8/2019 | Robinson et al. |
| 10,369,012 B2 | 8/2019 | Fessler |
| 10,376,377 B2 | 8/2019 | Seifert et al. |
| 10,390,962 B2 | 8/2019 | Weiman |
| 10,390,964 B2 | 8/2019 | Faulhaber |
| 10,398,563 B2 | 9/2019 | Engstrom |
| 10,398,566 B2 | 9/2019 | Olmos et al. |
| 10,413,419 B2 | 9/2019 | Thibodeau |
| 10,413,422 B2 | 9/2019 | Flower et al. |
| 10,413,423 B2 | 9/2019 | Overes et al. |
| 10,426,450 B2 | 10/2019 | Vogel et al. |
| 10,426,633 B2 | 10/2019 | Moskowitz et al. |
| 10,426,634 B1 | 10/2019 | Al-Jazaeri et al. |
| 10,441,430 B2 | 10/2019 | Ludwig et al. |
| 10,449,056 B2 | 10/2019 | Cain |
| 10,456,122 B2 | 10/2019 | Koltz et al. |
| 10,470,894 B2 | 11/2019 | Foley et al. |
| 10,478,319 B2 | 11/2019 | Moskowitz et al. |
| 10,492,912 B2 | 12/2019 | Gregersen et al. |
| 10,492,922 B2 | 12/2019 | Mathieu et al. |
| 10,492,924 B2 | 12/2019 | Stein et al. |
| 10,500,064 B2 | 12/2019 | Robinson |
| 10,512,550 B2 | 12/2019 | Bechtel et al. |
| 10,517,645 B2 | 12/2019 | van der Pol |
| 10,524,924 B2 | 1/2020 | Davenport et al. |
| 10,531,903 B2 | 1/2020 | Daly et al. |
| 10,537,436 B2 | 1/2020 | Maguire et al. |
| 10,537,438 B2 | 1/2020 | Martynova et al. |
| 10,555,729 B1 | 2/2020 | Cole et al. |
| 10,561,411 B1 | 2/2020 | Cole et al. |
| 10,575,889 B2 | 3/2020 | Roybal |
| 10,575,960 B2 | 3/2020 | Duffield et al. |
| 10,582,959 B2 | 3/2020 | Langer et al. |
| 10,583,015 B2 | 3/2020 | Olmos et al. |
| 10,603,078 B2 | 3/2020 | Simpson et al. |
| 10,610,376 B2 | 4/2020 | Kuyler et al. |
| 10,624,757 B2 | 4/2020 | Bost et al. |
| 10,624,758 B2 | 4/2020 | Slivka et al. |
| 10,624,761 B2 | 4/2020 | Davenport et al. |
| 10,639,163 B2 | 5/2020 | Tyber et al. |
| 10,639,166 B2 | 5/2020 | Weiman et al. |
| 10,653,458 B2 | 5/2020 | Tanaka et al. |
| 10,667,925 B2 | 6/2020 | Emerick et al. |
| 10,667,927 B2 | 6/2020 | Lamborne et al. |
| 10,675,157 B2 | 6/2020 | Zakelj et al. |
| 10,682,241 B2 | 6/2020 | Glerum et al. |
| 10,687,963 B2 | 6/2020 | Jimenez et al. |
| 10,702,393 B2 | 7/2020 | Davenport et al. |
| 10,709,569 B2 | 7/2020 | McLaughlin et al. |
| 10,709,571 B2 | 7/2020 | Iott et al. |
| 10,709,572 B2 | 7/2020 | Daffinson et al. |
| 10,709,575 B2 | 7/2020 | Robinson |
| 10,722,377 B2 | 7/2020 | Glerum et al. |
| 10,722,379 B2 | 7/2020 | McLaughlin et al. |
| 10,729,561 B2 | 8/2020 | Glerum |
| 10,743,858 B1 | 8/2020 | Cole et al. |
| 10,744,002 B2 | 8/2020 | Glerum et al. |
| 10,758,366 B2 | 9/2020 | Daffinson et al. |
| 10,758,367 B2 | 9/2020 | Weiman et al. |
| 10,758,369 B2 | 9/2020 | Rogers et al. |
| 10,765,528 B2 | 9/2020 | Weiman et al. |
| 10,772,737 B2 | 9/2020 | Gray et al. |
| 10,779,955 B2 | 9/2020 | Kuyler et al. |
| 10,779,957 B2 | 9/2020 | Weiman et al. |
| 10,786,364 B2 | 9/2020 | Davenport et al. |
| 10,786,369 B2 | 9/2020 | Carnes et al. |
| 10,799,368 B2 | 10/2020 | Glerum et al. |
| 10,835,387 B2 | 11/2020 | Weiman et al. |
| 10,842,640 B2 | 11/2020 | Weiman et al. |
| 10,842,644 B2 | 11/2020 | Weiman et al. |
| 10,856,997 B2 | 12/2020 | Cowan et al. |
| 10,869,769 B2 | 12/2020 | Eisen et al. |
| 10,874,447 B2 | 12/2020 | Tanaka et al. |
| 10,874,522 B2 | 12/2020 | Weiman |
| 10,874,523 B2 | 12/2020 | Weiman et al. |
| 10,874,524 B2 | 12/2020 | Bjork |
| 10,881,524 B2 | 1/2021 | Eisen et al. |
| 10,881,531 B2 | 1/2021 | Berry |
| 10,888,431 B1 | 1/2021 | Robinson |
| 10,898,344 B2 | 1/2021 | Alheidt et al. |
| 10,898,346 B1 | 1/2021 | Suddaby |
| 10,925,656 B2 | 2/2021 | Cole et al. |

(56) References Cited

U.S. PATENT DOCUMENTS

| | | |
|---|---|---|
| 10,925,750 B2 | 2/2021 | Zappacosta et al. |
| 10,925,752 B2 | 2/2021 | Weiman |
| 10,932,920 B2 | 3/2021 | Dewey et al. |
| 10,940,014 B2 | 3/2021 | Greenhalgh |
| 10,945,858 B2 | 3/2021 | Bechtel et al. |
| 10,952,866 B2 | 3/2021 | Warren et al. |
| 10,959,855 B2 | 3/2021 | Miller et al. |
| 10,959,856 B2 | 3/2021 | Seifert et al. |
| 10,973,649 B2 | 4/2021 | Weiman et al. |
| 10,973,650 B2 | 4/2021 | Stein |
| 10,980,642 B2 | 4/2021 | Glerum et al. |
| 10,980,644 B2 | 4/2021 | Purcell et al. |
| 10,993,814 B2 | 5/2021 | Wolters |
| 11,007,067 B2 | 5/2021 | Masson et al. |
| 11,013,617 B2 | 5/2021 | Weiman et al. |
| 11,020,238 B2 | 6/2021 | Nichols et al. |
| 11,020,239 B2 | 6/2021 | Miller et al. |
| 11,026,804 B2 | 6/2021 | Jimenez et al. |
| 11,026,812 B2 | 6/2021 | Daffinson et al. |
| 11,033,401 B2 | 6/2021 | Shoshtaev |
| 11,033,402 B2 | 6/2021 | Melkent et al. |
| 11,033,404 B2 | 6/2021 | Faulhaber |
| 11,039,935 B2 | 6/2021 | McAfee |
| 11,045,326 B2 | 6/2021 | Seifert et al. |
| 11,045,327 B2 | 6/2021 | Nichols et al. |
| 11,051,949 B2 | 7/2021 | Walker et al. |
| 11,051,951 B2 | 7/2021 | Robinson et al. |
| 11,058,469 B2 | 7/2021 | Mahajan et al. |
| 11,065,127 B1 | 7/2021 | Lentner et al. |
| 11,065,129 B2 | 7/2021 | Sandul |
| 11,065,130 B2 | 7/2021 | Branch et al. |
| 11,076,966 B2 | 8/2021 | Faulhaber |
| 11,083,584 B2 | 8/2021 | Lauf et al. |
| 11,083,595 B2 | 8/2021 | Robinson |
| 11,090,167 B2 | 8/2021 | Emerick et al. |
| 11,096,795 B2 | 8/2021 | Padovani et al. |
| 11,096,797 B2 | 8/2021 | Moskowitz et al. |
| 11,103,366 B2 | 8/2021 | Glerum et al. |
| RE48,719 E | 9/2021 | Suddaby et al. |
| 11,109,980 B2 | 9/2021 | Seifert et al. |
| 11,116,644 B2 | 9/2021 | Marrocco et al. |
| 11,123,198 B2 | 9/2021 | Black et al. |
| 11,123,200 B2 | 9/2021 | Faulhaber |
| 11,129,731 B2 | 9/2021 | Miller et al. |
| 11,135,071 B2 | 10/2021 | Dewey et al. |
| 11,147,680 B2 | 10/2021 | Tyber et al. |
| 11,154,404 B2 | 10/2021 | Freedman et al. |
| 11,160,666 B2 | 11/2021 | Burkhardt et al. |
| 11,160,669 B2 | 11/2021 | Rogers et al. |
| 11,166,826 B2 | 11/2021 | Huang |
| 11,173,044 B1 | 11/2021 | Jones et al. |
| 11,179,234 B2 | 11/2021 | Dacosta et al. |
| 11,285,014 B1 | 3/2022 | Josse et al. |
| 11,376,134 B1 | 7/2022 | Dewey et al. |
| 11,617,658 B2 | 4/2023 | Josse et al. |
| 11,723,780 B2 | 8/2023 | Seifert et al. |
| 11,737,892 B1* | 8/2023 | Kadaba ............... A61F 2/4455 623/17.16 |
| 12,064,354 B2* | 8/2024 | Robinson ............... A61F 2/447 |
| 2002/0045943 A1 | 4/2002 | Uk |
| 2002/0045945 A1 | 4/2002 | Liu et al. |
| 2002/0055741 A1 | 5/2002 | Schlapfer et al. |
| 2002/0116066 A1 | 8/2002 | Chauvin et al. |
| 2002/0128713 A1 | 9/2002 | Ferree |
| 2002/0151976 A1 | 10/2002 | Foley et al. |
| 2002/0183762 A1 | 12/2002 | Anderson et al. |
| 2003/0050701 A1 | 3/2003 | Michelson |
| 2003/0130739 A1 | 7/2003 | Gerbec et al. |
| 2003/0163132 A1 | 8/2003 | Chin |
| 2004/0102778 A1 | 5/2004 | Huebner et al. |
| 2004/0172134 A1 | 9/2004 | Berry |
| 2004/0186570 A1 | 9/2004 | Rapp |
| 2004/0193158 A1 | 9/2004 | Lim et al. |
| 2004/0204713 A1 | 10/2004 | Abdou |
| 2004/0249461 A1 | 12/2004 | Ferree |
| 2004/0254643 A1 | 12/2004 | Jackson |
| 2004/0254644 A1 | 12/2004 | Taylor |
| 2005/0015149 A1 | 1/2005 | Michelson |
| 2005/0033429 A1 | 2/2005 | Kuo |
| 2005/0033439 A1 | 2/2005 | Gordon et al. |
| 2005/0147478 A1 | 7/2005 | Greenberg |
| 2005/0154459 A1 | 7/2005 | Wolek et al. |
| 2005/0209698 A1 | 9/2005 | Gordon et al. |
| 2005/0228398 A1 | 10/2005 | Rathbun et al. |
| 2006/0122701 A1 | 6/2006 | Kiester |
| 2006/0129244 A1 | 6/2006 | Ensign |
| 2006/0260446 A1 | 11/2006 | Chang |
| 2006/0276901 A1 | 12/2006 | Zipnick et al. |
| 2007/0173840 A1 | 7/2007 | Huebner |
| 2007/0218750 A1 | 9/2007 | Corrao et al. |
| 2007/0233150 A1 | 10/2007 | Blain et al. |
| 2007/0270859 A1 | 11/2007 | Companioni et al. |
| 2008/0058804 A1 | 3/2008 | Lechot et al. |
| 2008/0132959 A1 | 6/2008 | Mikkonen et al. |
| 2008/0140207 A1 | 6/2008 | Olmos et al. |
| 2009/0024158 A1 | 1/2009 | Viker |
| 2009/0036746 A1 | 2/2009 | Blackwell et al. |
| 2009/0093830 A1 | 4/2009 | Miller |
| 2009/0105834 A1 | 4/2009 | Hovda et al. |
| 2009/0292361 A1 | 11/2009 | Lopez |
| 2010/0070035 A1* | 3/2010 | Mayer ............... A61F 2/447 623/17.11 |
| 2010/0076440 A1 | 3/2010 | Pamichev et al. |
| 2010/0082109 A1 | 4/2010 | Greenhalgh et al. |
| 2010/0152853 A1 | 6/2010 | Kirschman |
| 2010/0191336 A1 | 7/2010 | Greenhalgh |
| 2010/0211176 A1 | 8/2010 | Greenhalgh |
| 2010/0280617 A1* | 11/2010 | Coppes ............... A61F 2/4425 623/17.16 |
| 2010/0286777 A1 | 11/2010 | Errico et al. |
| 2011/0118843 A1 | 5/2011 | Mathieu et al. |
| 2011/0130838 A1 | 6/2011 | Morgenstern Lopez |
| 2011/0144755 A1 | 6/2011 | Baynham et al. |
| 2011/0153020 A1 | 6/2011 | Abdelgany et al. |
| 2011/0218572 A1 | 9/2011 | Lechmann et al. |
| 2011/0218631 A1* | 9/2011 | Woodburn, Sr. ....... A61F 2/4611 623/17.16 |
| 2011/0237898 A1 | 9/2011 | Stone et al. |
| 2011/0301577 A1 | 12/2011 | Simmen et al. |
| 2012/0004732 A1 | 1/2012 | Goel et al. |
| 2012/0095515 A1 | 4/2012 | Hamilton |
| 2012/0101581 A1 | 4/2012 | Mathieu et al. |
| 2012/0109142 A1 | 5/2012 | Dayan |
| 2012/0109309 A1 | 5/2012 | Mathieu et al. |
| 2012/0109310 A1 | 5/2012 | Mathieu et al. |
| 2012/0109312 A1 | 5/2012 | Mathieu et al. |
| 2012/0109313 A1 | 5/2012 | Mathieu et al. |
| 2012/0123546 A1 | 5/2012 | Medina |
| 2012/0143195 A1 | 6/2012 | Sander |
| 2012/0150237 A1 | 6/2012 | Combrowski |
| 2012/0197401 A1 | 8/2012 | Duncan et al. |
| 2012/0209385 A1 | 8/2012 | Aferzon |
| 2012/0215313 A1 | 8/2012 | Saidha et al. |
| 2012/0215316 A1 | 8/2012 | Mohr et al. |
| 2012/0232349 A1 | 9/2012 | Perrow |
| 2013/0103095 A1 | 4/2013 | Brumfield et al. |
| 2013/0158664 A1 | 6/2013 | Palmatier et al. |
| 2013/0184823 A1 | 7/2013 | Malberg |
| 2013/0190876 A1 | 7/2013 | Drochner et al. |
| 2013/0211526 A1 | 8/2013 | Alheidt et al. |
| 2013/0226191 A1 | 8/2013 | Thoren et al. |
| 2013/0231747 A1 | 9/2013 | Olmos et al. |
| 2013/0274557 A1 | 10/2013 | Bowman et al. |
| 2013/0304136 A1 | 11/2013 | Gourlaouen-Preissler et al. |
| 2013/0317312 A1 | 11/2013 | Eastlack et al. |
| 2014/0018816 A1 | 1/2014 | Fenn et al. |
| 2014/0039622 A1 | 2/2014 | Glerum et al. |
| 2014/0107790 A1 | 4/2014 | Combrowski |
| 2014/0114321 A1 | 4/2014 | Davenport et al. |
| 2014/0114420 A1 | 4/2014 | Robinson |
| 2014/0148904 A1 | 5/2014 | Robinson |
| 2014/0163682 A1 | 6/2014 | Iott et al. |
| 2014/0180419 A1 | 6/2014 | Dmuschewsky |
| 2014/0194992 A1 | 7/2014 | Medina |

(56) References Cited

U.S. PATENT DOCUMENTS

| | | |
|---|---|---|
| 2014/0249629 A1 | 9/2014 | Moskowitz et al. |
| 2014/0249631 A1 | 9/2014 | Weiman |
| 2014/0277471 A1 | 9/2014 | Gray et al. |
| 2014/0277473 A1 | 9/2014 | Perrow |
| 2014/0277487 A1 | 9/2014 | Davenport et al. |
| 2014/0277500 A1 | 9/2014 | Logan et al. |
| 2014/0303674 A1 | 10/2014 | Sasing |
| 2014/0364855 A1 | 12/2014 | Stoll et al. |
| 2014/0379085 A1 | 12/2014 | Duffield et al. |
| 2015/0173915 A1* | 6/2015 | Laubert ............ A61F 2/4611 |
| | | 623/17.16 |
| 2015/0223945 A1 | 8/2015 | Weiman et al. |
| 2015/0230931 A1 | 8/2015 | Greenhalgh |
| 2015/0238236 A1 | 8/2015 | Sasing |
| 2015/0354635 A1 | 12/2015 | McClymont et al. |
| 2015/0374507 A1 | 12/2015 | Wolters et al. |
| 2016/0008924 A1 | 1/2016 | Canourgues et al. |
| 2016/0022434 A1 | 1/2016 | Robinson |
| 2016/0051373 A1 | 2/2016 | Faulhaber |
| 2016/0058571 A1 | 3/2016 | McLaughlin et al. |
| 2016/0081681 A1 | 3/2016 | Waugh et al. |
| 2016/0089247 A1 | 3/2016 | Nichols et al. |
| 2016/0095710 A1 | 4/2016 | Juszczyk et al. |
| 2016/0095718 A1 | 4/2016 | Burkhardt et al. |
| 2016/0100951 A1* | 4/2016 | Suddaby ............ A61F 2/442 |
| | | 623/17.16 |
| 2016/0128847 A1* | 5/2016 | Kurtaliaj ........... A61B 17/7086 |
| | | 623/17.16 |
| 2016/0199073 A1 | 7/2016 | Nino et al. |
| 2016/0242930 A1 | 8/2016 | Duffield et al. |
| 2016/0256291 A1 | 9/2016 | Miller |
| 2016/0278830 A1 | 9/2016 | Arrington |
| 2016/0296340 A1 | 10/2016 | Gordon et al. |
| 2016/0310291 A1 | 10/2016 | Greenhalgh |
| 2016/0345952 A1 | 12/2016 | Kucharzyk et al. |
| 2016/0367377 A1 | 12/2016 | Faulhaber |
| 2017/0010025 A1 | 1/2017 | Mayershofer |
| 2017/0029635 A1 | 2/2017 | Doll et al. |
| 2017/0035406 A1 | 2/2017 | Abidin et al. |
| 2017/0049651 A1 | 2/2017 | Lim et al. |
| 2017/0049653 A1 | 2/2017 | Lim et al. |
| 2017/0095345 A1 | 4/2017 | Davenport et al. |
| 2017/0100255 A1 | 4/2017 | Hleihil et al. |
| 2017/0100257 A1 | 4/2017 | Weiman et al. |
| 2017/0105844 A1 | 4/2017 | Kuyler et al. |
| 2017/0112630 A1 | 4/2017 | Kuyler et al. |
| 2017/0151065 A1 | 6/2017 | Warren et al. |
| 2017/0156882 A1 | 6/2017 | Rathbun et al. |
| 2017/0156884 A1 | 6/2017 | Rathbun et al. |
| 2017/0189200 A1 | 7/2017 | Miller et al. |
| 2017/0189204 A1 | 7/2017 | Riemhofer et al. |
| 2017/0202678 A1 | 7/2017 | Duffield et al. |
| 2017/0215856 A1 | 8/2017 | Martinelli et al. |
| 2017/0224502 A1 | 8/2017 | Wolters et al. |
| 2017/0224504 A1 | 8/2017 | Butler et al. |
| 2017/0231675 A1 | 8/2017 | Combrowski |
| 2017/0231780 A1* | 8/2017 | D'Urso ............ A61F 2/4455 |
| | | 623/17.16 |
| 2017/0246006 A1 | 8/2017 | Carnes et al. |
| 2017/0290677 A1 | 10/2017 | Olmos et al. |
| 2017/0296352 A1 | 10/2017 | Richerme et al. |
| 2017/0333200 A1 | 11/2017 | Arnin |
| 2017/0367842 A1 | 12/2017 | Predick et al. |
| 2017/0367843 A1 | 12/2017 | Eisen et al. |
| 2017/0367844 A1 | 12/2017 | Eisen et al. |
| 2017/0367845 A1 | 12/2017 | Eisen et al. |
| 2018/0000606 A1 | 1/2018 | Hessler et al. |
| 2018/0030362 A1 | 2/2018 | Kosler et al. |
| 2018/0031810 A1 | 2/2018 | Hsu et al. |
| 2018/0036136 A1 | 2/2018 | Duffield et al. |
| 2018/0036138 A1 | 2/2018 | Robinson |
| 2018/0104066 A1 | 4/2018 | Bae et al. |
| 2018/0116819 A1 | 5/2018 | Maguire et al. |
| 2018/0116891 A1 | 5/2018 | Beale et al. |
| 2018/0193160 A1 | 7/2018 | Hsu et al. |
| 2018/0193164 A1 | 7/2018 | Shoshtaev |
| 2018/0206999 A1 | 7/2018 | Suddaby |
| 2018/0256356 A1 | 9/2018 | Robinson et al. |
| 2018/0256359 A1 | 9/2018 | Greenhalgh |
| 2018/0256360 A1 | 9/2018 | Cain |
| 2018/0256362 A1 | 9/2018 | Slivka et al. |
| 2018/0263784 A1 | 9/2018 | Bechtel et al. |
| 2018/0271513 A1 | 9/2018 | Perrow et al. |
| 2018/0280142 A1 | 10/2018 | Schultz et al. |
| 2018/0303473 A1 | 10/2018 | Spann et al. |
| 2018/0303621 A1 | 10/2018 | Brotman et al. |
| 2018/0303625 A1 | 10/2018 | Alheidt et al. |
| 2018/0311048 A1 | 11/2018 | Glerum et al. |
| 2018/0318101 A1 | 11/2018 | Engstrom |
| 2018/0318102 A1 | 11/2018 | Seifert et al. |
| 2018/0325574 A1 | 11/2018 | Bjork et al. |
| 2018/0338838 A1 | 11/2018 | Cryder et al. |
| 2018/0338841 A1 | 11/2018 | Miller et al. |
| 2018/0344307 A1 | 12/2018 | Hynes et al. |
| 2018/0360616 A1 | 12/2018 | Luu |
| 2019/0000640 A1 | 1/2019 | Weiman |
| 2019/0000702 A1 | 1/2019 | Lim et al. |
| 2019/0000707 A1 | 1/2019 | Lim et al. |
| 2019/0020121 A1 | 1/2019 | Paulotto et al. |
| 2019/0021716 A1 | 1/2019 | Waugh et al. |
| 2019/0021873 A1 | 1/2019 | Dmuschewsky |
| 2019/0046329 A1 | 2/2019 | Padovani et al. |
| 2019/0046381 A1 | 2/2019 | Lim et al. |
| 2019/0046383 A1 | 2/2019 | Lim et al. |
| 2019/0060083 A1 | 2/2019 | Weiman et al. |
| 2019/0082949 A1 | 3/2019 | Weiman |
| 2019/0083081 A1 | 3/2019 | Ortiz et al. |
| 2019/0091033 A1 | 3/2019 | Dewey et al. |
| 2019/0105175 A1 | 4/2019 | Zappacosta et al. |
| 2019/0125328 A1 | 5/2019 | Blain |
| 2019/0133434 A1 | 5/2019 | Lee et al. |
| 2019/0133645 A1 | 5/2019 | Gordon et al. |
| 2019/0133779 A1 | 5/2019 | McLaughlin et al. |
| 2019/0133780 A1 | 5/2019 | Matthews et al. |
| 2019/0133784 A1 | 5/2019 | Gunn et al. |
| 2019/0133788 A1 | 5/2019 | Weiman et al. |
| 2019/0142480 A1 | 5/2019 | Woolley et al. |
| 2019/0151115 A1 | 5/2019 | Nichols et al. |
| 2019/0183656 A1 | 6/2019 | Stein |
| 2019/0201209 A1 | 7/2019 | Branch et al. |
| 2019/0201210 A1 | 7/2019 | Besaw et al. |
| 2019/0209155 A1 | 7/2019 | Mast et al. |
| 2019/0216453 A1 | 7/2019 | Predick et al. |
| 2019/0231552 A1 | 8/2019 | Sandul |
| 2019/0240039 A1 | 8/2019 | Walker et al. |
| 2019/0240043 A1 | 8/2019 | Greenhalgh |
| 2019/0247098 A1 | 8/2019 | Brumfield et al. |
| 2019/0254650 A1 | 8/2019 | Martinelli et al. |
| 2019/0254838 A1 | 8/2019 | Miller et al. |
| 2019/0254839 A1 | 8/2019 | Nichols et al. |
| 2019/0262009 A1 | 8/2019 | Cheng |
| 2019/0262139 A1 | 8/2019 | Wolters |
| 2019/0269521 A1 | 9/2019 | Shoshtaev |
| 2019/0274670 A1 | 9/2019 | O'Connell et al. |
| 2019/0274671 A1 | 9/2019 | Lauf et al. |
| 2019/0274836 A1 | 9/2019 | Eisen et al. |
| 2019/0282373 A1 | 9/2019 | Alheidt |
| 2019/0290446 A1 | 9/2019 | Masson et al. |
| 2019/0290447 A1 | 9/2019 | Stein |
| 2019/0298416 A1 | 10/2019 | Rezach |
| 2019/0298524 A1 | 10/2019 | Lauf et al. |
| 2019/0298540 A1 | 10/2019 | Aghayev et al. |
| 2019/0321022 A1 | 10/2019 | Karpowicz et al. |
| 2019/0321190 A1 | 10/2019 | Wagner et al. |
| 2019/0328539 A1 | 10/2019 | Suh et al. |
| 2019/0328540 A1 | 10/2019 | Seifert et al. |
| 2019/0329388 A1 | 10/2019 | Erickson et al. |
| 2019/0336301 A1 | 11/2019 | Engstrom |
| 2019/0336304 A1 | 11/2019 | Burkhardt et al. |
| 2019/0350573 A1 | 11/2019 | Vogel et al. |
| 2019/0358049 A1 | 11/2019 | Faulhaber |
| 2019/0358050 A1 | 11/2019 | Fessler |
| 2019/0358051 A1 | 11/2019 | Flower et al. |
| 2019/0380840 A1 | 12/2019 | Tyber et al. |

(56) References Cited

U.S. PATENT DOCUMENTS

| | | |
|---|---|---|
| 2019/0388232 A1 | 12/2019 | Purcell et al. |
| 2020/0008951 A1 | 1/2020 | McClintock et al. |
| 2020/0030114 A1 | 1/2020 | Cain |
| 2020/0030116 A1 | 1/2020 | Jimenez et al. |
| 2020/0038200 A1 | 2/2020 | Foley et al. |
| 2020/0054461 A1 | 2/2020 | Marrocco et al. |
| 2020/0060844 A1 | 2/2020 | Mathieu et al. |
| 2020/0069316 A1 | 3/2020 | DeSoutter et al. |
| 2020/0078190 A1 | 3/2020 | Rogers et al. |
| 2020/0093526 A1 | 3/2020 | Daly et al. |
| 2020/0093607 A1 | 3/2020 | Davenport et al. |
| 2020/0093609 A1 | 3/2020 | Shoshtaev |
| 2020/0100904 A1 | 4/2020 | Stein et al. |
| 2020/0107824 A1 | 4/2020 | Fleischer |
| 2020/0129306 A1 | 4/2020 | Miller et al. |
| 2020/0129307 A1 | 4/2020 | Hunziker et al. |
| 2020/0138591 A1 | 5/2020 | Moskowitz et al. |
| 2020/0138593 A1 | 5/2020 | Martynova et al. |
| 2020/0146840 A1 | 5/2020 | Black et al. |
| 2020/0179120 A1 | 6/2020 | Bielenstein et al. |
| 2020/0205993 A1 | 7/2020 | Davenport et al. |
| 2020/0214754 A1 | 7/2020 | Bowen et al. |
| 2020/0222202 A1 | 7/2020 | Kuyler et al. |
| 2020/0229944 A1 | 7/2020 | Suh et al. |
| 2020/0246159 A1 | 8/2020 | Suh et al. |
| 2020/0246162 A1 | 8/2020 | Schultz et al. |
| 2020/0261242 A1 | 8/2020 | Bost et al. |
| 2020/0268524 A1 | 8/2020 | Glerum et al. |
| 2020/0276028 A1 | 9/2020 | Blain et al. |
| 2020/0281741 A1 | 9/2020 | Grotz |
| 2020/0289287 A1 | 9/2020 | Emerick et al. |
| 2020/0297507 A1 | 9/2020 | Iott et al. |
| 2020/0330239 A1 | 10/2020 | Davenport et al. |
| 2020/0330245 A1 | 10/2020 | Glerum |
| 2020/0345511 A1 | 11/2020 | Daffinson et al. |
| 2020/0352731 A1 | 11/2020 | Berry |
| 2020/0352738 A1 | 11/2020 | Berry |
| 2020/0360153 A1 | 11/2020 | Weiman et al. |
| 2020/0375753 A1 | 12/2020 | McLaughlin et al. |
| 2020/0375755 A1 | 12/2020 | Cain |
| 2020/0383797 A1 | 12/2020 | Predick et al. |
| 2020/0383799 A1 | 12/2020 | Cain |
| 2020/0390433 A1 | 12/2020 | Yu et al. |
| 2020/0390565 A1 | 12/2020 | Jimenez et al. |
| 2020/0397593 A1 | 12/2020 | Davenport et al. |
| 2020/0405497 A1 | 12/2020 | Olmos et al. |
| 2020/0405498 A1 | 12/2020 | Gray et al. |
| 2020/0405499 A1 | 12/2020 | Gerbec et al. |
| 2020/0405500 A1 | 12/2020 | Cain |
| 2021/0007860 A1 | 1/2021 | Glerum et al. |
| 2021/0015626 A1 | 1/2021 | Suddaby |
| 2021/0030555 A1 | 2/2021 | Weiman et al. |
| 2021/0030561 A1 | 2/2021 | Gleason |
| 2021/0045891 A1 | 2/2021 | Rogers et al. |
| 2021/0045892 A1 | 2/2021 | Rogers et al. |
| 2021/0052395 A1 | 2/2021 | Iott et al. |
| 2021/0068959 A1 | 3/2021 | McLuen et al. |
| 2021/0068974 A1 | 3/2021 | Cowan et al. |
| 2021/0068982 A1 | 3/2021 | Carnes et al. |
| 2021/0077271 A1 | 3/2021 | Sharabani |
| 2021/0077272 A1 | 3/2021 | Eisen et al. |
| 2021/0085479 A1 | 3/2021 | Weiman et al. |
| 2021/0093462 A1 | 4/2021 | Lucasiewicz et al. |
| 2021/0106434 A1 | 4/2021 | Alheidt et al. |
| 2021/0113349 A1 | 4/2021 | Weiman et al. |
| 2021/0121299 A1 | 4/2021 | Hyder |
| 2021/0121300 A1 | 4/2021 | Weiman et al. |
| 2021/0137697 A1 | 5/2021 | Weiman |
| 2021/0137699 A1 | 5/2021 | Jang et al. |
| 2021/0137701 A1 | 5/2021 | Miller et al. |
| 2021/0154811 A1 | 5/2021 | Spreiter et al. |
| 2021/0161678 A1 | 6/2021 | Dewey et al. |
| 2021/0177618 A1 | 6/2021 | Branch et al. |
| 2021/0186706 A1 | 6/2021 | Spitler et al. |
| 2021/0186709 A1 | 6/2021 | Weiman et al. |
| 2021/0196470 A1 | 7/2021 | Shoshtaev |
| 2021/0205092 A1 | 7/2021 | Glerum et al. |
| 2021/0205094 A1 | 7/2021 | Weiman et al. |
| 2021/0220145 A1 | 7/2021 | Stein |
| 2021/0220147 A1 | 7/2021 | Berry |
| 2021/0236298 A1 | 8/2021 | Weiman et al. |
| 2021/0251770 A1 | 8/2021 | Purcell et al. |
| 2021/0251776 A1 | 8/2021 | Daffinson et al. |
| 2021/0259848 A1 | 8/2021 | Kang et al. |
| 2021/0259849 A1 | 8/2021 | Robinson et al. |
| 2021/0259850 A1 | 8/2021 | Eisen et al. |
| 2021/0267767 A1 | 9/2021 | Stein |
| 2021/0275317 A1 | 9/2021 | Spetzger |
| 2021/0275318 A1 | 9/2021 | Reimels |
| 2021/0275319 A1 | 9/2021 | Reimels |
| 2021/0275321 A1 | 9/2021 | Seifert et al. |
| 2021/0282938 A1 | 9/2021 | Nichols et al. |
| 2021/0298915 A1 | 9/2021 | Faulhaber |
| 2021/0298916 A1 | 9/2021 | Melkent et al. |
| 2021/0307920 A1 | 10/2021 | Walker et al. |
| 2021/0315705 A1 | 10/2021 | Altarac et al. |
| 2021/0322179 A1 | 10/2021 | Miller et al. |
| 2021/0322181 A1 | 10/2021 | Predick |
| 2021/0322182 A1 | 10/2021 | Faulhaber |
| 2021/0330472 A1 | 10/2021 | Shoshtaev |
| 2021/0346174 A1 | 11/2021 | Flint et al. |
| 2021/0353277 A1 | 11/2021 | Gregersen et al. |
| 2021/0401586 A1 | 12/2021 | Zakelj |
| 2022/0015924 A1 | 1/2022 | Freedman et al. |
| 2022/0047312 A1 | 2/2022 | Seykora et al. |
| 2022/0087819 A1* | 3/2022 | Robinson .............. A61F 2/4455 |
| 2022/0133336 A1 | 5/2022 | Tsai et al. |
| 2022/0133497 A1 | 5/2022 | Dewey et al. |
| 2022/0133498 A1 | 5/2022 | Josse et al. |
| 2022/0133499 A1 | 5/2022 | Josse et al. |
| 2022/0218325 A1 | 7/2022 | Josse |
| 2022/0265256 A1 | 8/2022 | Villamil et al. |
| 2022/0313450 A1 | 10/2022 | Donohoe et al. |
| 2022/0387184 A1 | 12/2022 | Josse et al. |
| 2022/0409397 A1 | 12/2022 | Hayes et al. |
| 2023/0015512 A1 | 1/2023 | Eisen et al. |
| 2023/0027836 A1 | 1/2023 | Predick et al. |
| 2023/0137358 A1* | 5/2023 | Hayes ................... A61F 2/4611 |
| | | 623/17.15 |

FOREIGN PATENT DOCUMENTS

| | | |
|---|---|---|
| EP | 0 767 636 A1 | 4/1997 |
| EP | 0 880 950 A1 | 12/1998 |
| EP | 0 857 042 B1 | 11/2001 |
| EP | 1 442 732 A1 | 8/2004 |
| EP | 1 124 512 B1 | 9/2004 |
| EP | 1 107 711 B1 | 10/2004 |
| EP | 1 506 753 A1 | 2/2005 |
| EP | 1 459 711 B1 | 7/2007 |
| EP | 2954860 A2 | 12/2015 |
| EP | 3031424 A1 | 6/2016 |
| EP | 3 069 694 A1 | 9/2016 |
| EP | 3213720 A1 | 9/2017 |
| FR | 2781998 A1 | 2/2000 |
| FR | 3082115 A1 | 12/2019 |
| GB | 2 377 387 A | 1/2003 |
| KR | 102117224 B1 | 6/2020 |
| KR | 102192022 B1 | 12/2020 |
| WO | 92/14423 A1 | 9/1992 |
| WO | 97/00054 A1 | 1/1997 |
| WO | 99/26562 A1 | 6/1999 |
| WO | 99/66867 A1 | 12/1999 |
| WO | 00/12033 A1 | 3/2000 |
| WO | 00/25706 A1 | 5/2000 |
| WO | 00/49977 A1 | 8/2000 |
| WO | 02/19952 A1 | 3/2002 |
| WO | 03/105673 A2 | 12/2003 |
| WO | 2006116850 A1 | 11/2006 |
| WO | 2012139022 A2 | 10/2012 |
| WO | 2014/133755 A1 | 9/2014 |
| WO | 2015063721 A1 | 5/2015 |
| WO | 2015198335 A1 | 12/2015 |
| WO | 2016057940 A1 | 4/2016 |

(56) References Cited

FOREIGN PATENT DOCUMENTS

| WO | 2016/205607 | A1 | 12/2016 |
|----|-------------|-----|---------|
| WO | 2017/168208 | A1 | 10/2017 |
| WO | 2018049227 | A1 | 3/2018 |
| WO | 2021055323 | A1 | 3/2021 |

OTHER PUBLICATIONS

International Search Report and Written Opinion in Application No. PCT/IB2023/057720 dated Nov. 8, 2023.
International Search Report and Written Opinion, PCT/IB2020/000932, Dated Jul. 29, 2021.
International Search Report and Written Opinion, PCT/IB2020/000942, Dated Aug. 10, 2021.
International Search Report and Written Opinion in Application No. PCT/IB2023/058417 dated Dec. 7, 2023.
International Search Report and Written Opinion in Application No. PCT/US2022/016831 dated Sep. 29, 2022.
Chinese Office Action in Application No. 201980010758.4 dated Jun. 16, 2023.
International Search Report, and Written Opinion for Application. No. PCT/US2019/019067, dated Jun. 3, 2019.
International Search Report and Written Opinion for Application No. PCT/US2019/019060, dated Jun. 5, 2019.
International Search Report and Written Opinion in Application No. PCT/US2022/027200 dated Aug. 19, 2022.
Chinese Office Action in Application No. 201980010758.4 dated Sep. 16, 2023.
International Search Report and Written Opinion in Application No. PCT/US2022/016809 dated Jul. 27, 2022.
International Search Report and Written Opinion in Application No. PCT/US2022/027695 dated Jul. 27, 2022.
International Search Report and Written Opinion in Application No. PCT/IB2024/054985 dated Sep. 10, 2024.
European Search Report in Application No. 22828961.7 dated Mar. 14, 2025.

* cited by examiner

100

100

100

100

EXPANDABLE INTERBODY IMPLANT AND CORRESPONDING INSERTER

CROSS-REFERENCE TO RELATED APPLICATIONS

This application is a continuation in part of U.S. patent application Ser. No. 17/356,950, titled EXPANDABLE INTERBODY IMPLANT, and filed Jun. 24, 2021. The entire disclosure of which is incorporated herein by reference. This application also incorporates by reference the entire contents of U.S. application Ser. No. 17/307,578, titled EXTERNALLY DRIVEN EXPANDABLE INTERBODY AND RELATED METHODS, and filed May 5, 2021.

FIELD

The present technology is generally related to an externally driven expandable interbody implant for use in a medical procedure related to the spine. In some embodiments, disclosed implants may be used in an anterior cervical discectomy and fusion (ACDF) procedure although other uses in other areas of the spine or between two bones are also contemplated.

BACKGROUND

Mechanically operated interbody implants may be used to align and/or realign a patient's spine during a medical procedure and/or for purposes of fusion, degenerative tissue and/or trauma/repair procedures. Conventional implants designed for the Thoracic and Lumbar region of the spine often include top and bottom endplates and a mechanical means to separate the top and bottom endplates. The mechanical mechanisms to separate the top and bottom endplates are often cumbersome and require a large footprint that is often unsuitable, for example, for ACDF type surgeries of the cervical portion of the spine.

SUMMARY

The techniques of this disclosure generally relate to an expandable interbody implant including a superior endplate and an inferior endplate hingedly coupled and which may further include a locking element to secure the inferior endplate and superior endplate in a particular configuration, for example. The superior and inferior endplates may be moved in a multitude of expanded and/or lordosed or kyphosed or otherwise angled configurations via an external inserter for example. In various embodiments, a locking screw may be a break-off type screw. In various embodiments at least one break-off tang on the implant may be used to for gripping of the implant to insert it into a disc space and afterwards the break-off tang may be broken off and removed. Additionally, in various embodiments the locking screw may be used to grip the implant and insert it into a disc space. Additionally, in various embodiments female recesses, rather than tangs, may be used for gripping of the implant and inserting the implant into a disc space.

In one aspect, the present disclosure provides for an expandable implant movable between a contracted position and an expanded position, for example. The expandable implant may include an expandable body extending from a proximal end to a distal end in a proximal-to-distal direction and extending from a first lateral side to a second lateral side in a widthwise direction, for example. The expandable body may be defined by a superior endplate and an inferior endplate opposite the superior endplate for example. In various embodiments, the superior endplate may include a channel located adjacent the distal end and extending in the widthwise direction, and a first core having a distal engagement surface, for example. In various embodiments, the inferior endplate may include a rail located adjacent the distal end and extending in the widthwise direction, the rail having a size and shape generally corresponding to a size and shape of the channel and being located within the channel, for example. In various embodiments, the inferior endplate may also include a second core having a proximal engagement surface and a threaded screw aperture, for example. In various embodiments, the implant may include a threaded locking screw disposed in the threaded screw aperture and movable between a locked position and an unlocked position, for example. Additionally, in various embodiments, in the locked position, the threaded locking screw may urge the distal engagement surface of the first core into direct contact with the proximal engagement surface of the second core, for example.

In another aspect, the disclosure provides for an expandable implant system. The system may include an inserter tool extending in a lengthwise direction from a proximal end thereof to a distal end thereof, the inserter tool may include a drive shaft supporting a drive end adjacent the distal end thereof and a pair of mounting arms adjacent the distal end thereof, for example. The system may also include an expandable implant movable between a contracted position and an expanded position, the expandable implant may include an expandable body extending from a proximal end to a distal end in a proximal-to-distal direction and extending from a first lateral side to a second lateral side in a widthwise direction, for example. In various embodiments, the expandable body may be defined by a superior endplate and an inferior endplate opposite the superior endplate, for example. In various embodiments, the superior endplate may include a channel located adjacent the distal end and extending in the widthwise direction, a first mounting tang and a first core having a distal engagement surface, for example. In various embodiments, the inferior endplate may include a rail located adjacent the distal end and extending in the widthwise direction, the rail may have a size and shape corresponding to a size and shape of the channel and be located within the channel, for example. The inferior endplate may also include a second mounting tang, and a second core having a proximal engagement surface and a threaded screw aperture, for example. In various embodiments, the system may further include a threaded locking screw disposed in the threaded screw aperture and movable between a locked position and an unlocked position, for example. In various embodiments, in the locked position, the threaded locking screw may urge the distal engagement surface of the first core into direct contact with the proximal engagement surface of the second core, for example. Additionally, in an insertion configuration, the first and second mounting tangs of the expandable implant may be disposed within the first and second mounting arms of the inserter tool, for example. Furthermore, in various embodiments, the drive end of the inserter tool may have a size and shape generally corresponding to a size and shape of a drive end of the threaded locking screw, for example.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 29 is a reference drawing showing the human spine of which various disclosed implant embodiments may be installed in.

DETAILED DESCRIPTION

Figure 1:
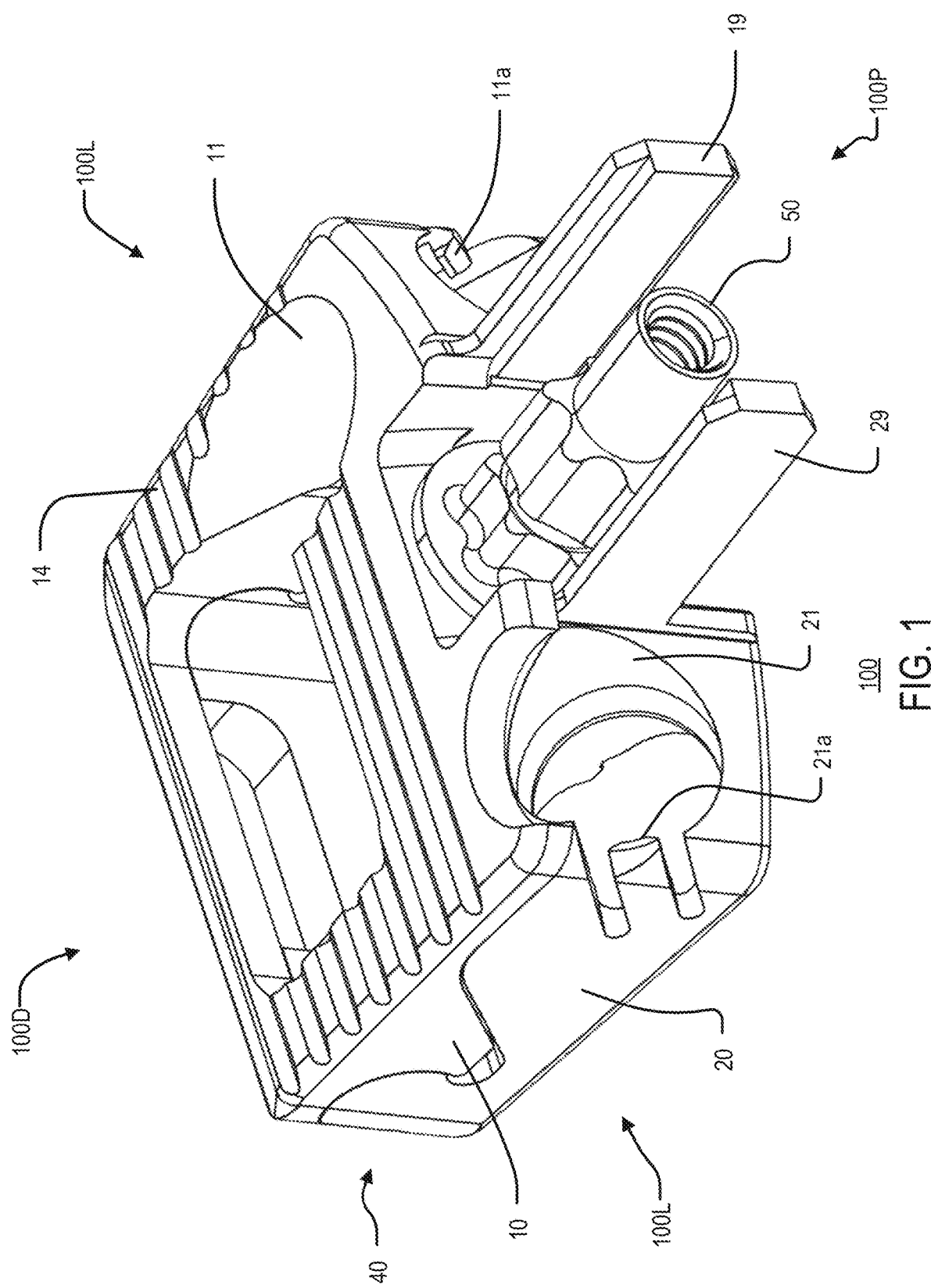
FIG. 1 is a perspective view of an expandable implant.

Embodiments of the present disclosure relate generally, for example, to spinal stabilization systems, and more particularly, to surgical instruments for use with spinal stabilization systems. Embodiments of the devices and methods are described below with reference to the Figures.

The following discussion omits or only briefly describes certain components, features and functionality related to medical implants, installation tools, and associated surgical techniques, which are apparent to those of ordinary skill in the art. It is noted that various embodiments are described in detail with reference to the drawings, in which like reference numerals represent like parts and assemblies throughout the several views, where possible. Reference to various embodiments does not limit the scope of the claims appended hereto because the embodiments are examples of the inventive concepts described herein. Additionally, any example(s) set forth in this specification are intended to be non-limiting and set forth some of the many possible embodiments applicable to the appended claims. Further, particular features described herein can be used in combination with other described features in each of the various possible combinations and permutations unless the context or other statements clearly indicate otherwise.

Terms such as "same," "equal," "planar," "coplanar," "parallel," "perpendicular," etc. as used herein are intended to encompass a meaning of exactly the same while also including variations that may occur, for example, due to manufacturing processes. The term "substantially" may be used herein to emphasize this meaning, particularly when the described embodiment has the same or nearly the same functionality or characteristic, unless the context or other statements clearly indicate otherwise.

Figure 25:
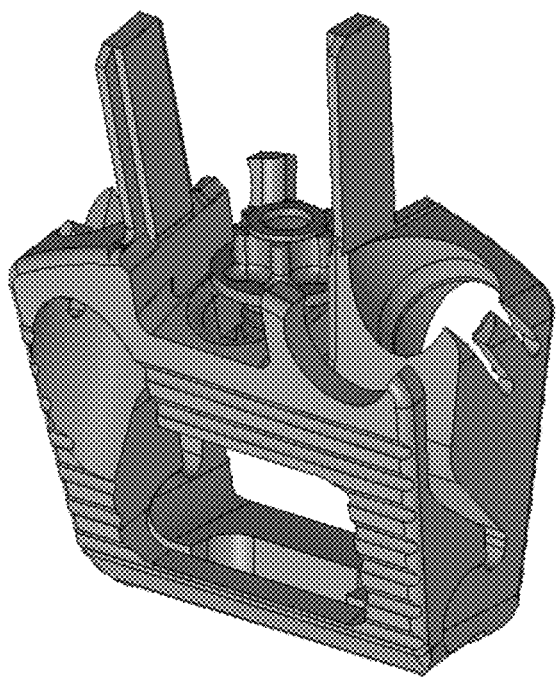
FIG. 25 is a perspective view of an expandable implant in an expanded configuration after a break-off portion of a locking screw has been broken off.
Figure 26:
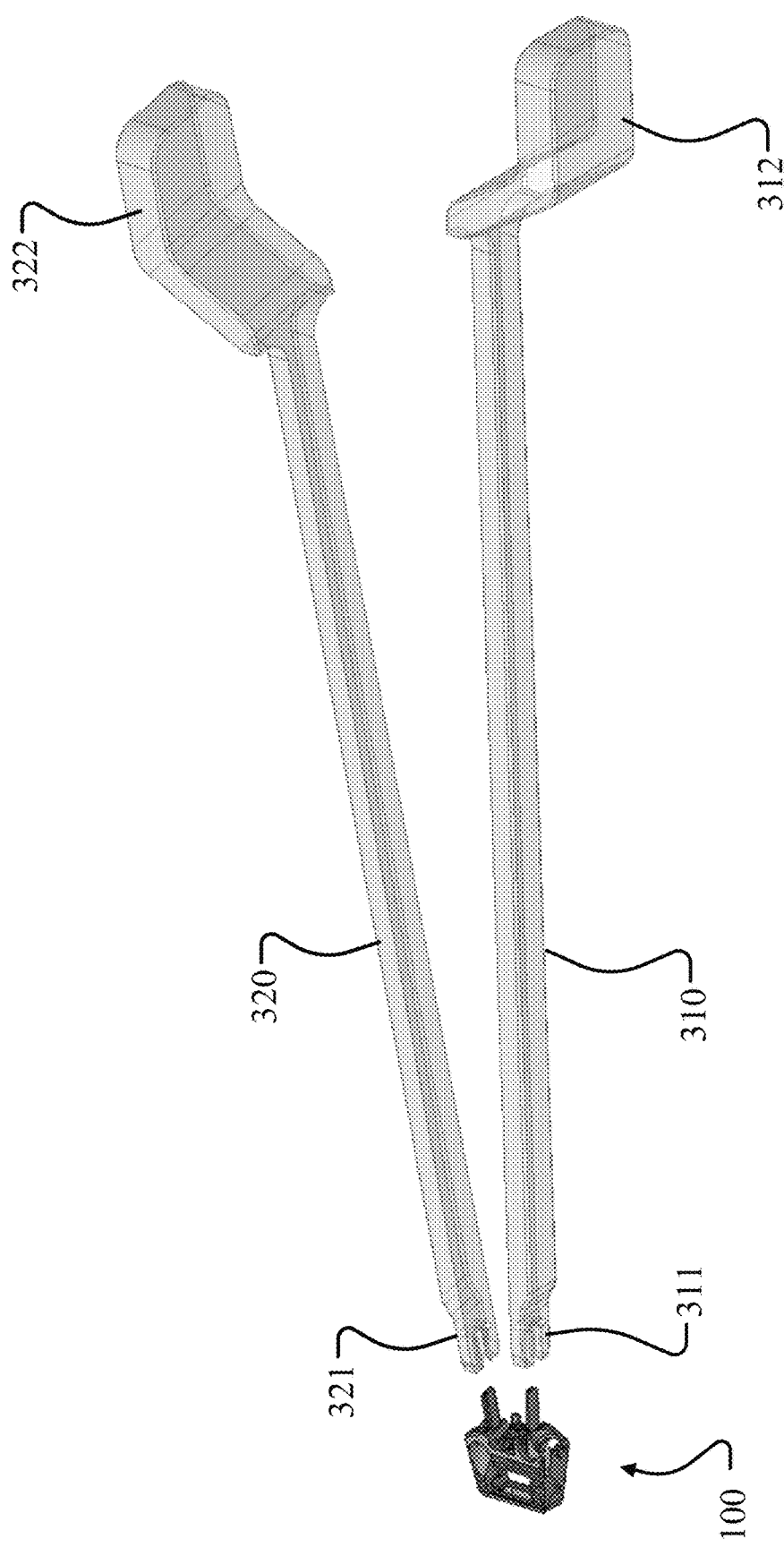
FIG. 26 is a perspective view of a surgical instrument for use with disclosed expandable implants.
Figure 27:
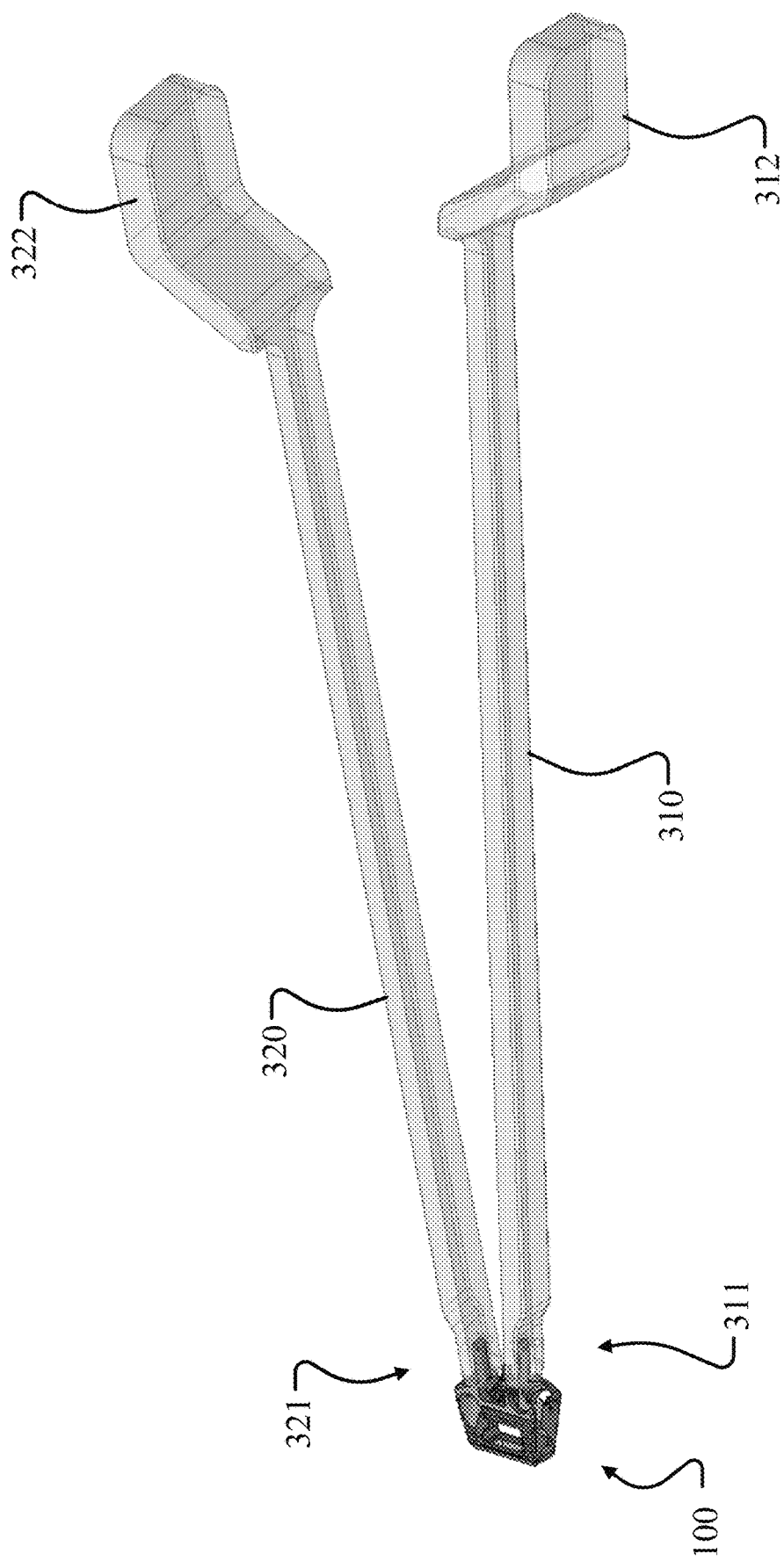
FIG. 27 is a perspective view of a surgical instrument for use with disclosed expandable implants.
Figure 28:
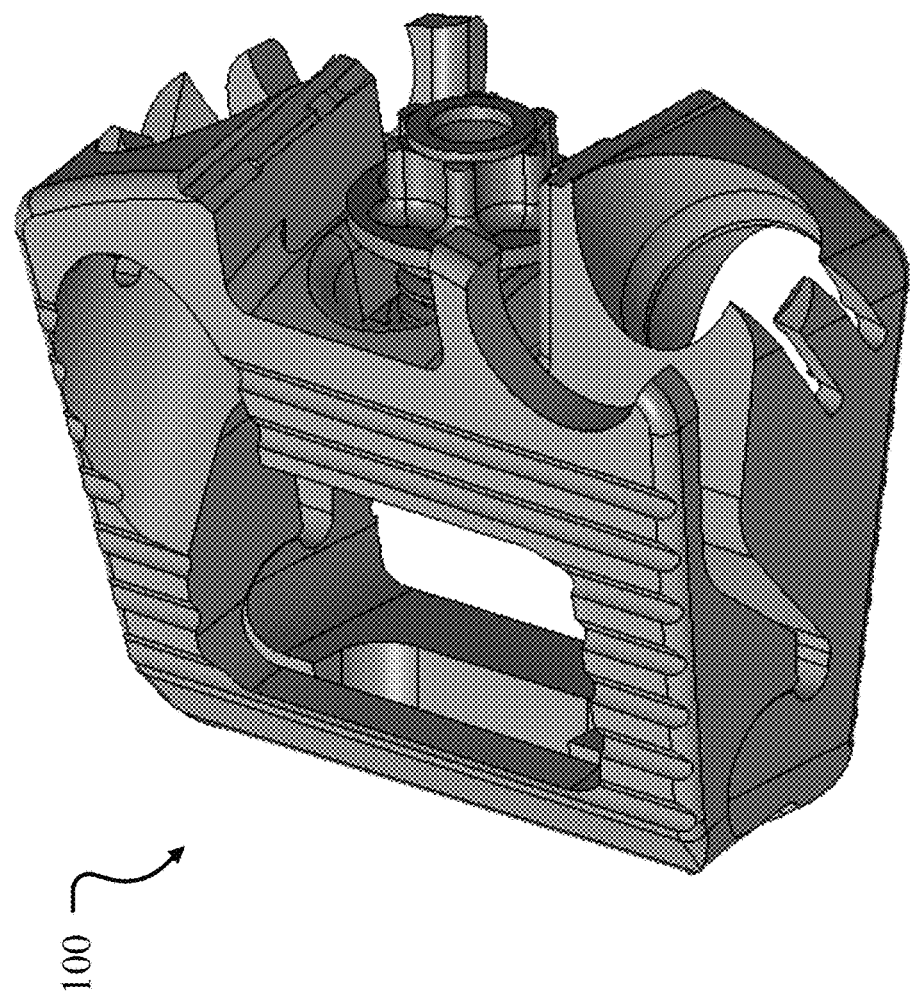
FIG. 28 is a perspective view of an expandable implant after the mounting tangs have been broken off.

Referring to FIGS. 1-19 generally, various embodiments and views of an expandable implant 100 are disclosed. Referring generally to FIGS. 20-25 various views of an inserter tool 200 for use with various expandable implant 100 embodiments are disclosed. Referring generally to FIGS. 26-28 various views of a break-off tool 300 for breaking off mounting tangs 19, 29 of various expandable implants 100 is disclosed. The components of expandable implant 100, inserter tool 200, and/or break-off tool 300 can be fabricated from biologically acceptable materials suitable for medical applications, including metals, synthetic polymers, ceramics and bone material and/or their composites. For example, the components, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe, polylactic acid or polylactide and their combinations.

Figure 2:
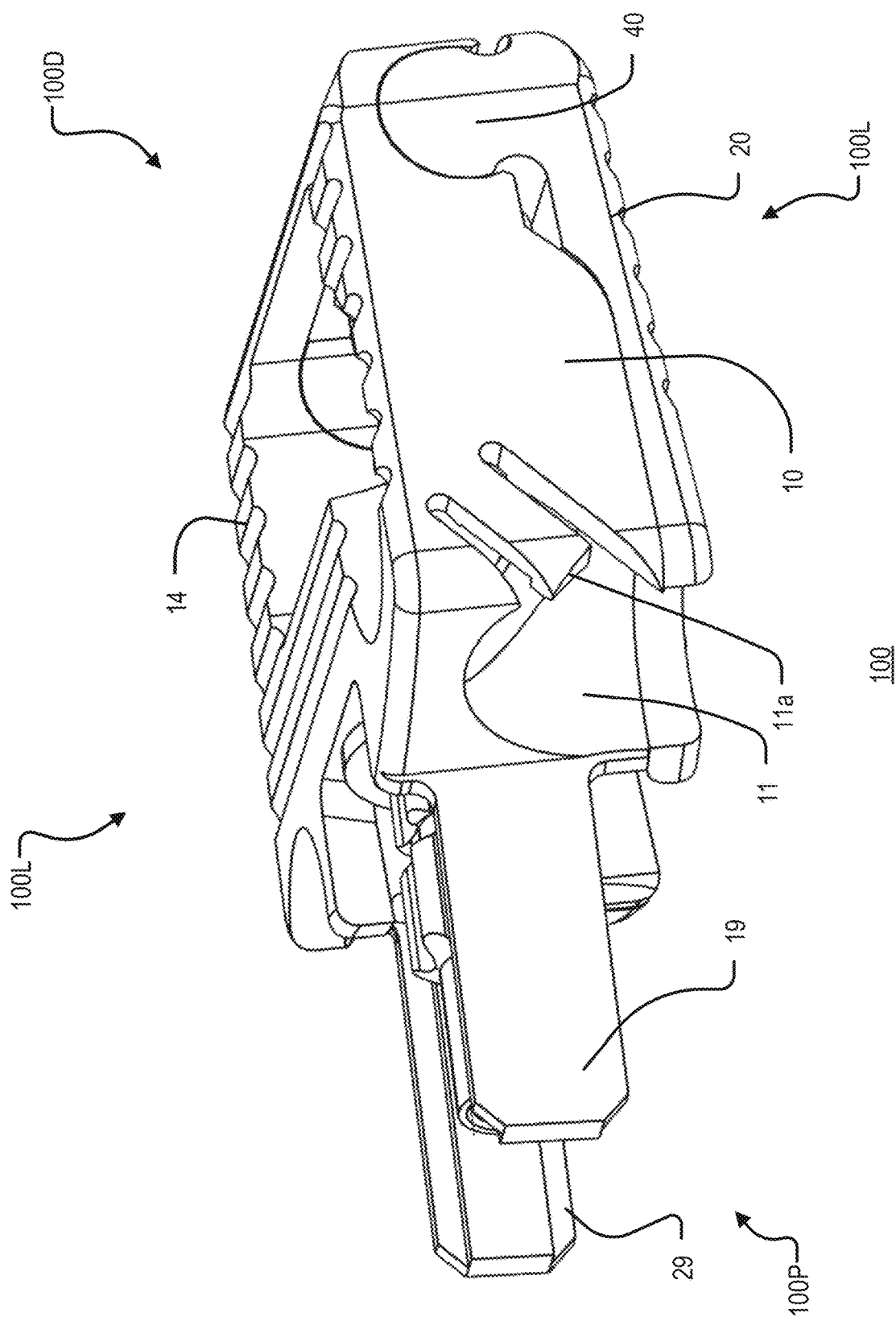
FIG. 2 is an alternate perspective view of an expandable implant.
Figure 3:
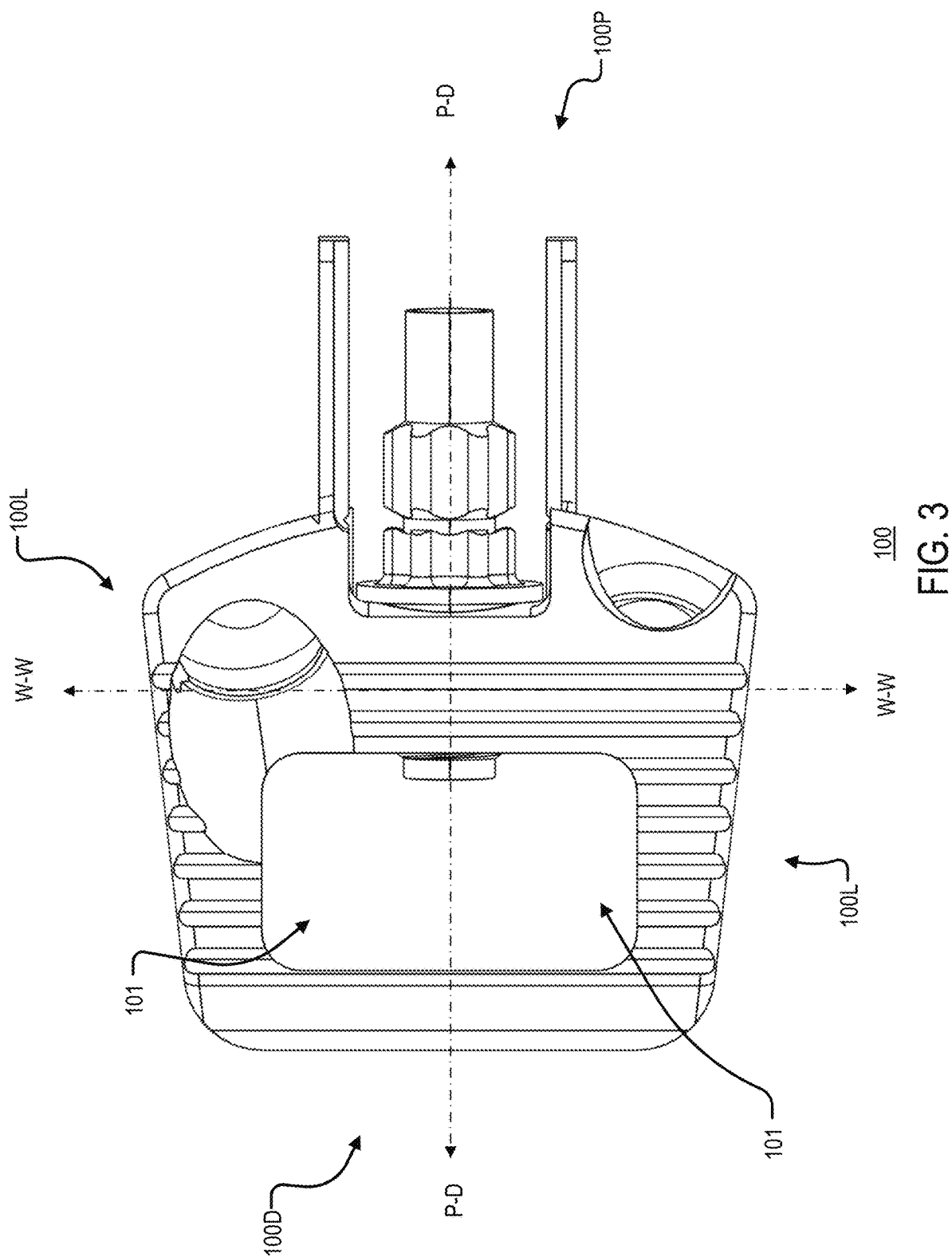
FIG. 3 is a top down view of an expandable implant.

Referring generally to FIGS. 1-5 various views of an expandable implant 100 in a collapsed position are illustrated. FIGS. 1-2 are various perspective views of an expandable implant 100. FIGS. 1-2 illustrate example perspective views of an expandable implant 100 in a partially expanded position and FIG. 3 is a top down view of an expandable implant 100. In the example embodiment, expandable implant 100 may include a proximal end 100P, a distal end 100D, and first and second lateral sides 100L. Additionally, a pair of bone screw apertures 11, 21 may be positioned on the proximal end 100P, for example. In various embodiments, bone screw apertures 11, 21 may comprise a corresponding bone screw retention mechanism 11a, 21a (may also be referred to as an anti-backout locking mechanism). In the example embodiment, the bone screw retention mechanisms 11a, 21a, comprise a flexible tang member having a hook portion at an end thereof that allows the flexible tang member to flex outward in a lateral direction away from the corresponding bone screw aperture 11, 21 during initial installation of the bone screw and to flex back inward towards the corresponding bone screw aperture 11, 21 to prevent a corresponding bone screw from backing out. For example, as the bone is installed in bone screw aperture 11, 21, the bone screw retention mechanism 11a, 21a, may flex outward as the underside of the head portion contacts inclined surface 11c (see FIG. 19).

In various embodiments, and as illustrated in FIGS. 1-2, mounting tangs 19, 29 may extend in a proximal direction, for example. In various embodiments, implant 100 may be referred to as an externally driven expandable implant because an end user or surgeon may use a surgical tool to open and close implant 100, e.g. expand implant 100. For example, an external tool may adjust the lordotic angle of implant 100 as will be explained in detail with respect to FIGS. 20-25. Once implant 100 is expanded to an appropriate lordotic angle (also referred to as angle of inclination), an end user may fix the relative angle of the superior endplate 10 relative to the inferior endplate 20 by tightening locking screw 50, for example. In some embodiments, superior endplate 10 may be referred to as a "cephalad" endplate and inferior endplate 20 may be referred to as a "caudal" endplate.

Locking screw 50 may also be used in other embodiments, such as fixation of posterior rods, fixation of pedicle screws, and other set screw constructs. Additionally, locking screw 50 may be referred to as a "break-off screw" in some embodiments.

At least one advantage of relying on an external tool to adjust a lordotic angle of implant 100 may be the reduction of internal components within implant 100 relative to other forms of implants relying on various moving mechanisms and/or expansion mechanisms, for example. Accordingly, in various embodiments, implant 100 may have a relatively large void space in the interior thereof, which may facilitate a fusion process during an ACDF procedure. For example, implant 100 may have a relatively large internal volume 101 that is open through the superior endplate 10 and inferior endplate 20 which may be packed with bone graft material, for example.

As illustrated in FIG. 3, implant 100 may extend in a proximal-to-distal direction (also referred to as a longitudinal direction) from the proximal end 100P to the distal end 100D though axis P-D through the center of the implant 100, for example. Implant 100 may extend in a widthwise direction (also referred to as lateral direction) from the first lateral side 100L to the second lateral side 100L through axis W-W through the center of the implant 100 and the center of locking screw 50, for example. The axis P-D may be perpendicular and/or substantially perpendicular to the axis W-W. For example, the proximal-to-distal direction may be perpendicular to the widthwise direction. Additionally, a width of the implant may taper from a proximal end 100P where it is widest towards a distal end 100D where it is narrowest.

Figure 4:
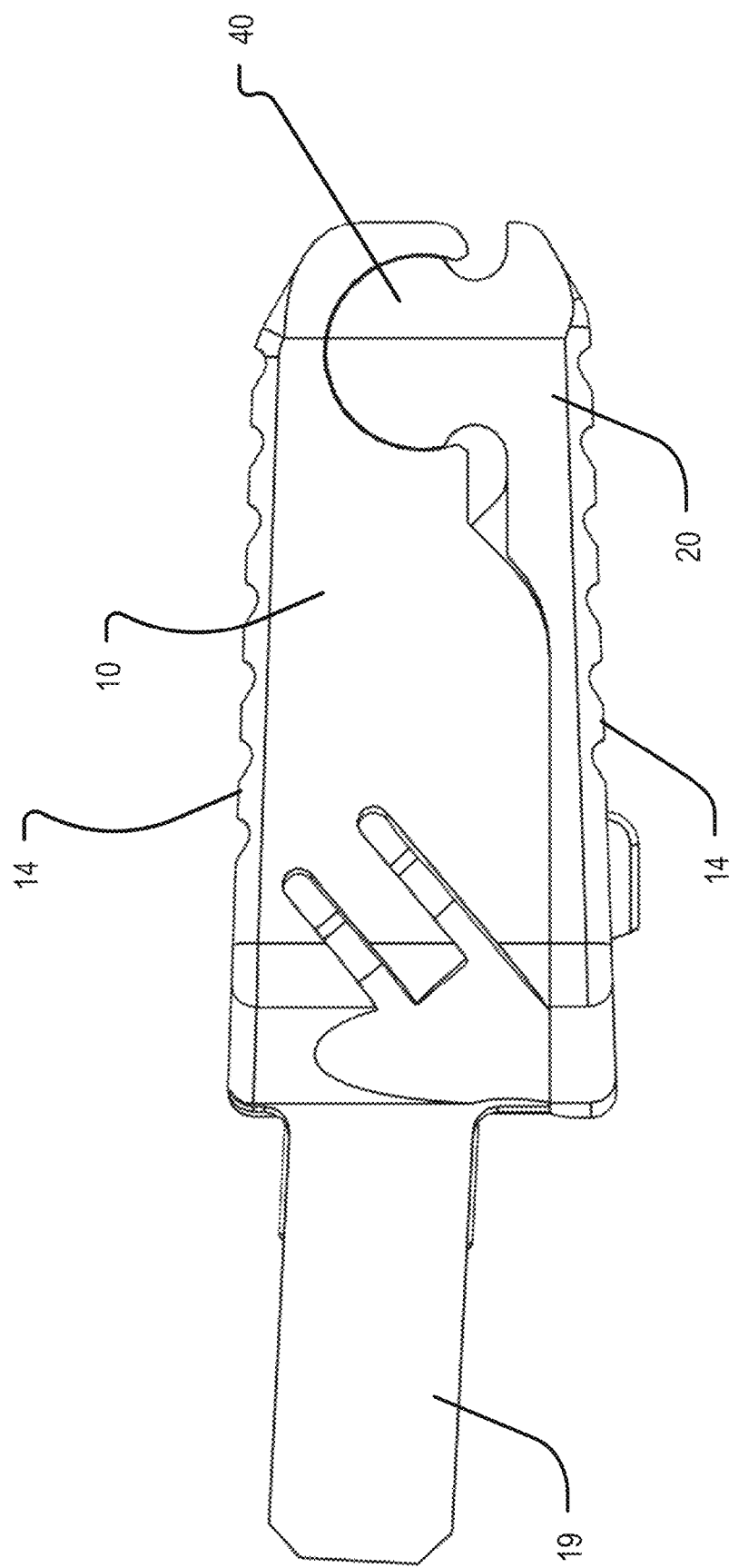
FIG. 4 is a side view of an expandable implant.

FIG. 4 is a side view of an expandable implant 100. In the example illustration, it is shown that a superior endplate 10 is connected to an inferior endplate 20 such that the superior endplate may pivot about a hinge member 40. In the example embodiment, hinge member 40 comprises an arcuate rail portion of inferior endplate 20 that extends in the widthwise direction, for example. In the example embodiment, hinge member 40 may be nested into a corresponding arcuate cavity of the superior endplate 10 such that superior endplate 10 may expand and/or otherwise rotate about hinge member 40. Additionally, in various embodiments the superior endplate 10 and/or inferior endplate 20 may include various engagement elements 14 for engaging with an adjacent boney structure such as a vertebrae, for example. In the example embodiment, the engagement elements comprise a series of alternating rails and valleys therebetween that extend in the widthwise direction. However, claws, hooks, dimples, spikes, etc. are also contemplated as example engagement elements 14. In some embodiments, an acid etching process may be utilized to form a roughened or textured surface to facilitate securing the implant between boney portions and/or suppressing expulsion of implant 100.

Figure 5:
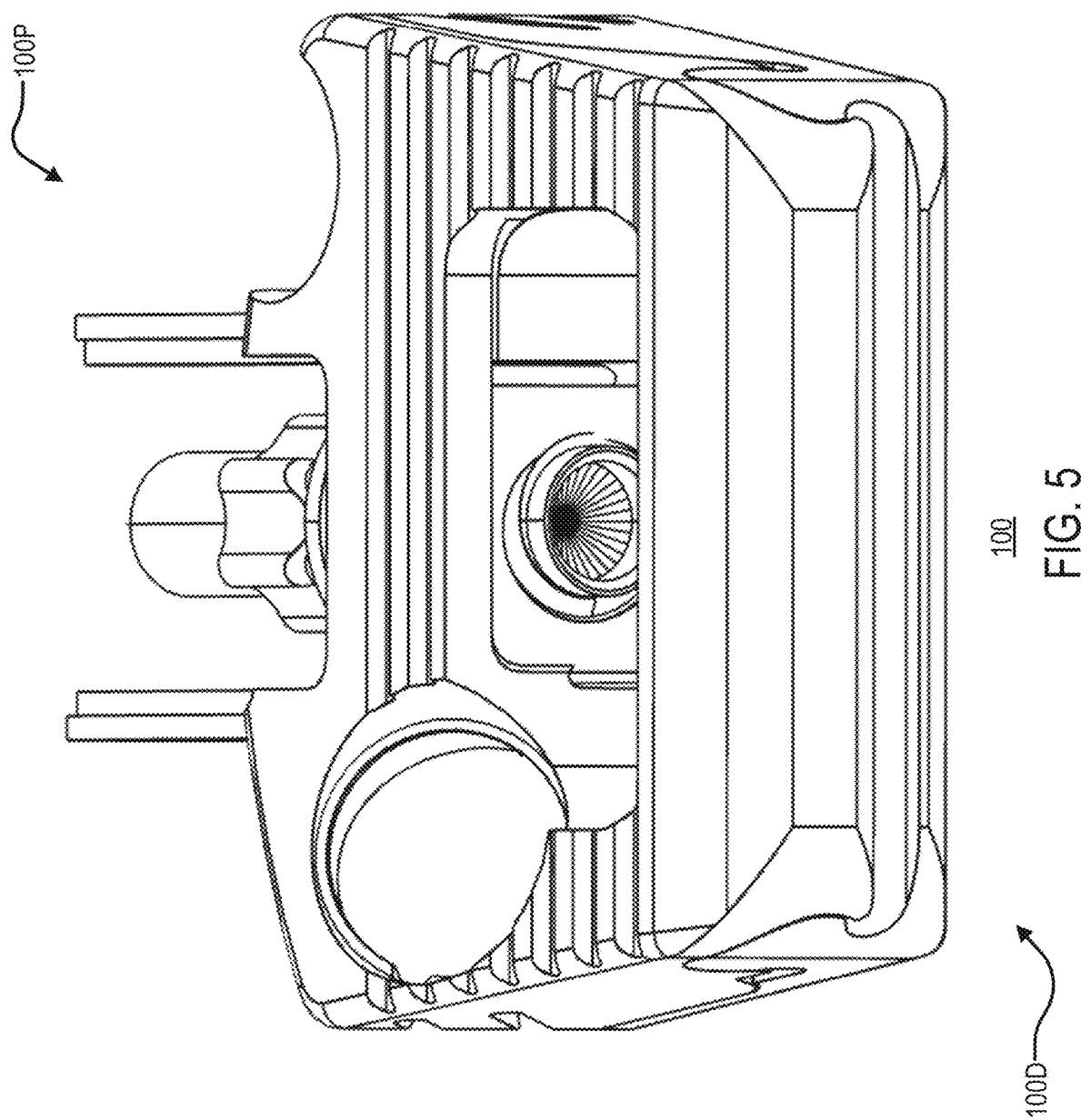
FIG. 5 is a rear view of an expandable implant.
Figure 6:
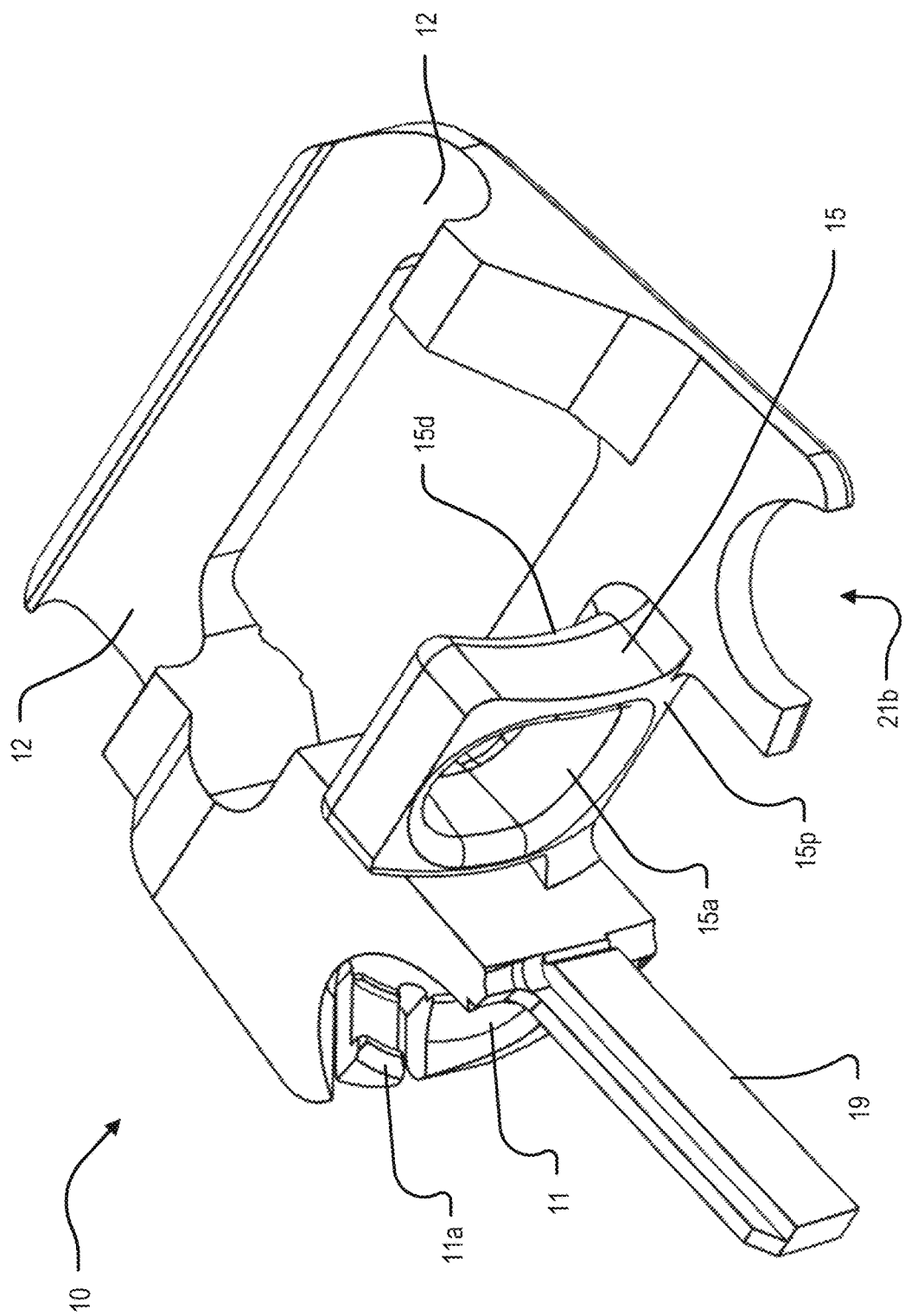
FIG. 6 is a perspective view of the interior of a superior endplate of an expandable implant.
Figure 7:
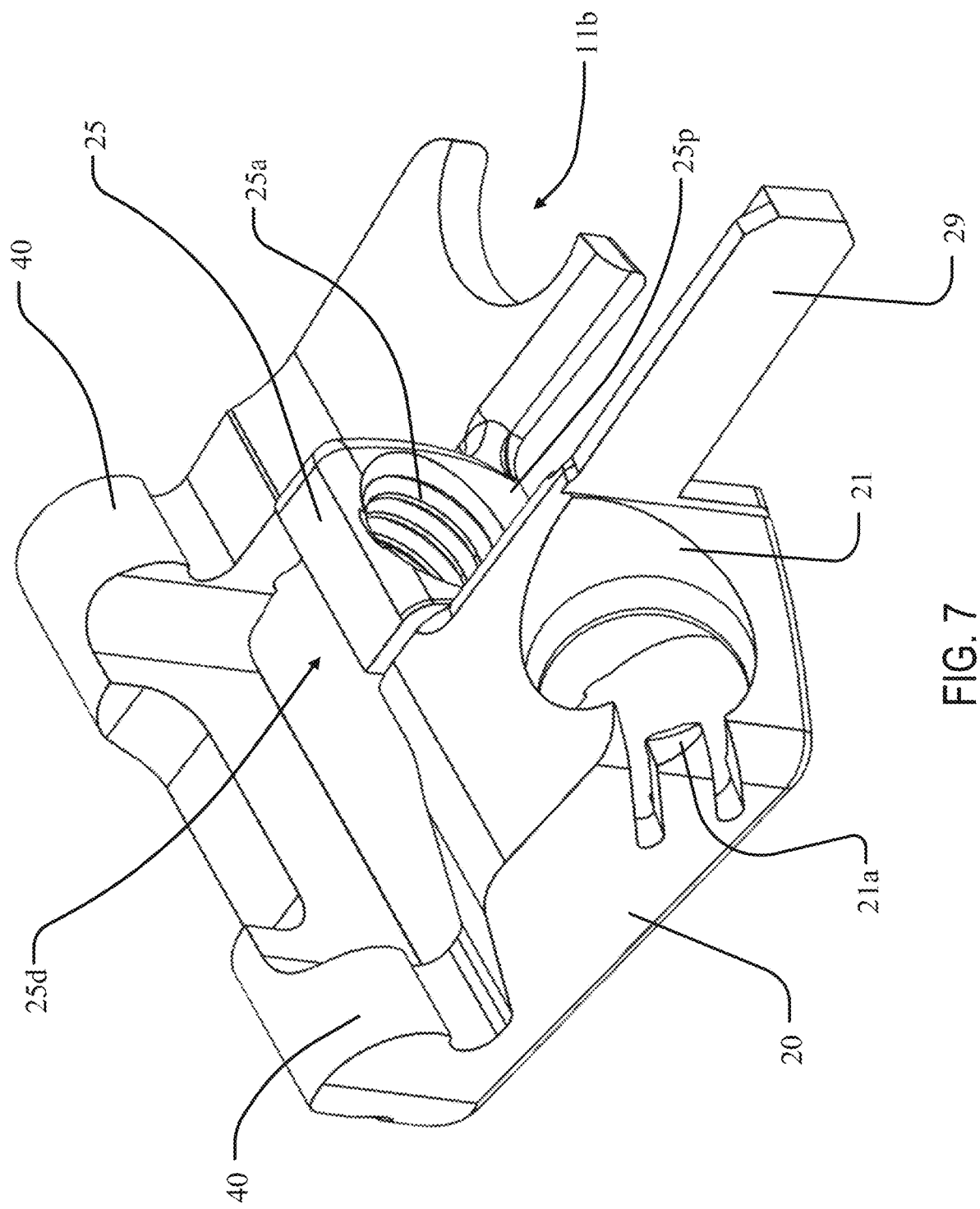
FIG. 7 is a perspective view of the interior of an inferior endplate of an expandable implant.

FIG. 5 is a rear perspective view of an expandable implant 100. In the example illustration it is shown that the distal end 100D is narrower than the proximal end 100P. FIG. 6 is a perspective view of the interior of a superior endplate 10. In the example illustration, it is shown that the distal end of superior endplate 10 includes an arcuate channel 12 of which the hinge member 40 may be disposed inside of. The proximal end of superior endplate 10 may include a bone screw aperture cutout 21b to allow a relief area for a corresponding bone screw to be insert through bone screw aperture 21 of inferior endplate 20, for example. Superior endplate 10 may also include a core 15 comprising an aperture 15a that extends from a proximal surface 15p thereof to a distal surface 15d thereof, for example. In some embodiments, core 15 may be referred to as a support frame and take a generally rectangular shape. In various embodiments, the distal surface 15d may be curved and generally face the distal end 100D of implant 100. FIG. 7 is a perspective view of the interior of an inferior endplate 20. In the example illustration, it is shown that the distal end of inferior endplate 20 includes a hinge member 40 in the form of an arcuate rail that may be disposed inside of the arcuate channel 12 of the superior endplate 10, for example. The proximal end of inferior endplate 20 may include a bone screw aperture cutout 11b to allow a relief area for a corresponding bone screw to be insert through bone screw aperture 11 of superior endplate 10, for example. Inferior endplate 20 may also include a core 25 comprising a threaded aperture 25a that extends from a proximal surface 25p thereof to a distal surface 25d thereof, for example. In some embodiments, core 25 may be referred to as a support frame and take a generally rectangular shape. In various embodiments, the superior endplate 10 and inferior endplate 20 may each be formed a unitary single piece, respectively.

Figure 8:
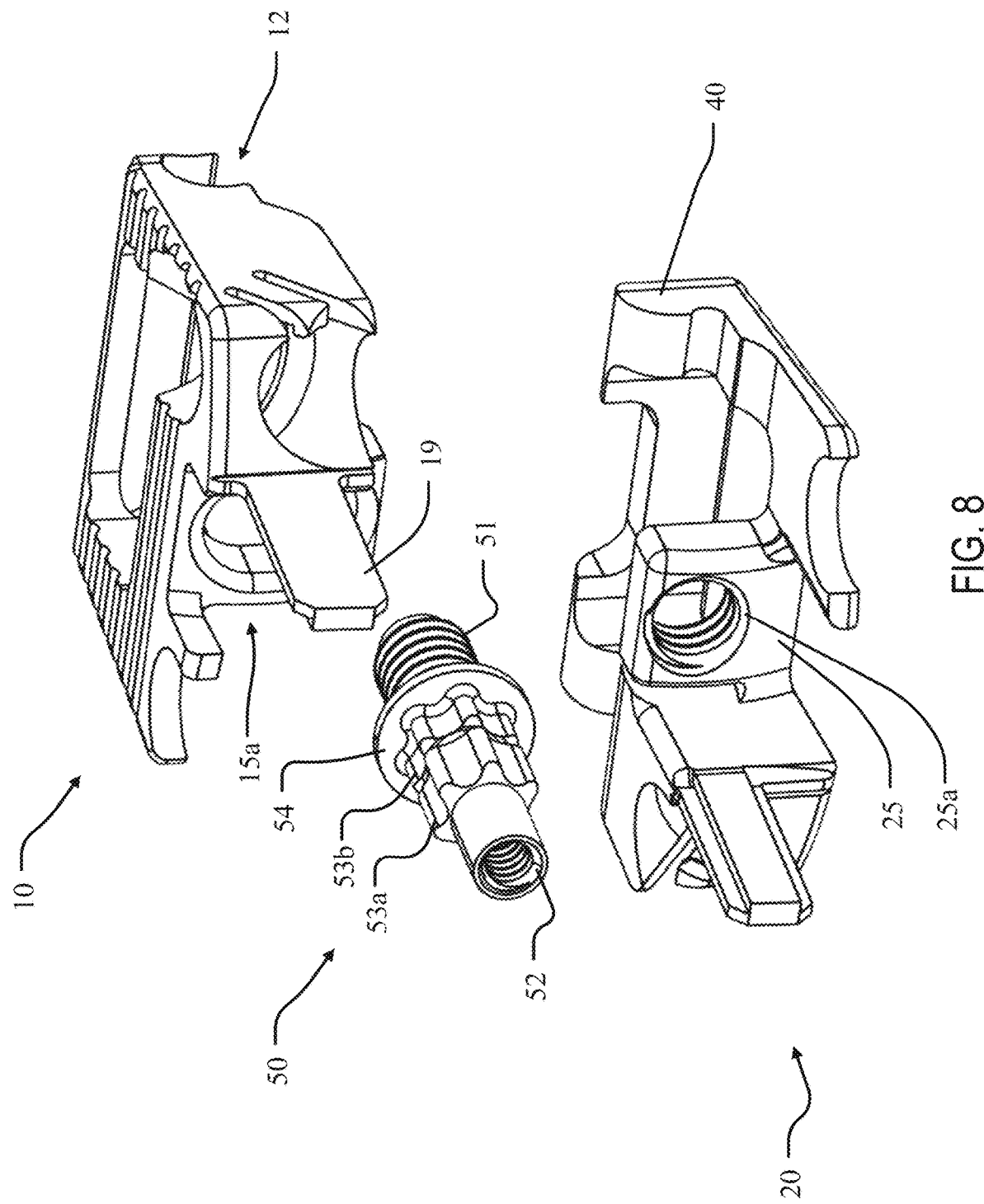
FIG. 8 is a perspective exploded parts view of an expandable implant.
Figure 9:
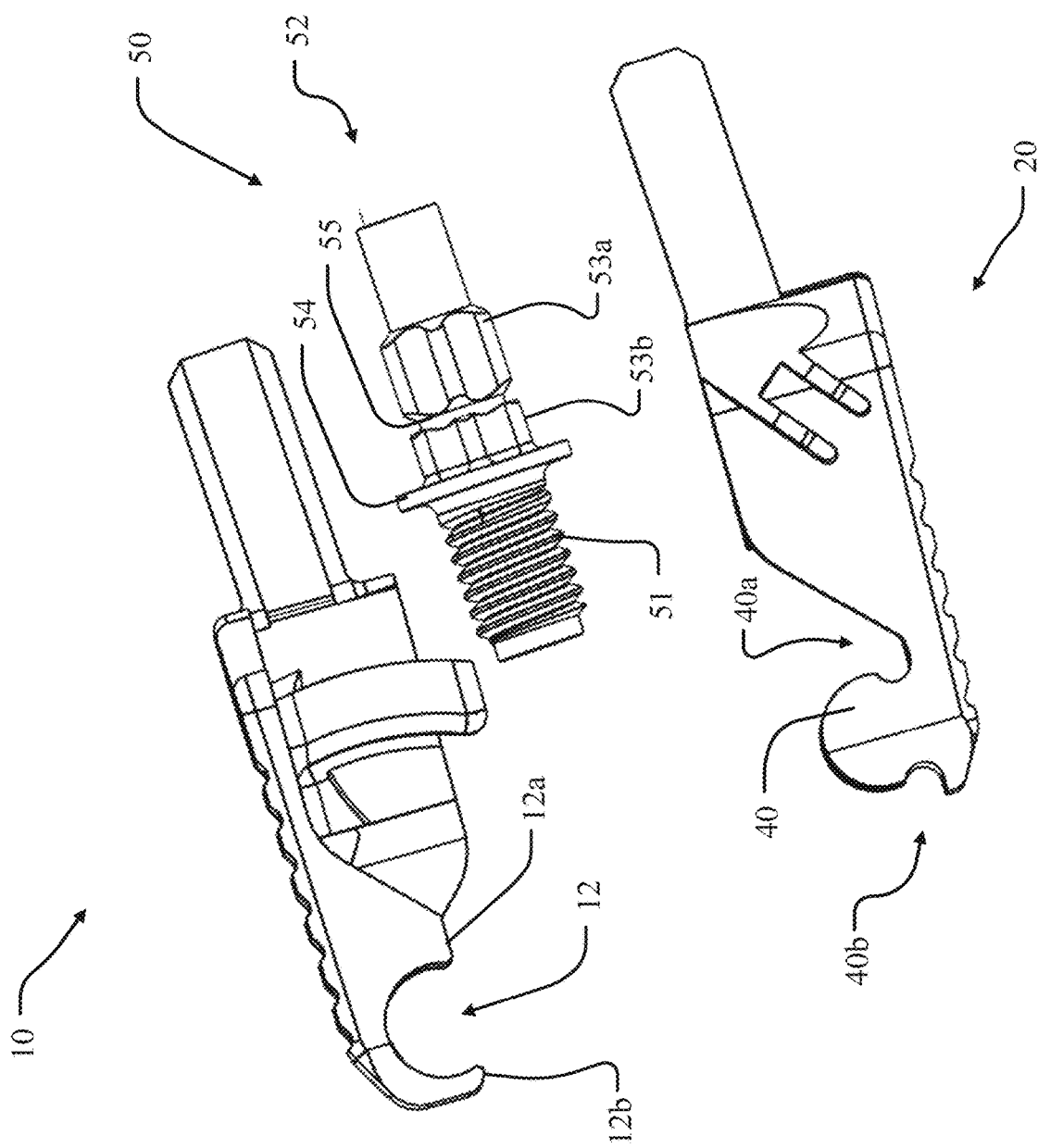
FIG. 9 an exploded parts view of an expandable implant from a side view perspective.

FIG. 8 is a perspective exploded parts view and FIG. 9 is an exploded parts view from a side view perspective of an expandable implant 100. In the example embodiment, a locking screw 50 is illustrated. Locking screw 50 may include an external thread pattern 51 on an outside circumferential surface thereof, for example. The external thread pattern 51 of locking screw 50 may have a size and shape generally corresponding to the threaded aperture 25a of core 25 of inferior endplate 20, for example. In various embodiments, an engagement surface 54 may be disposed adjacent and proximal of external thread pattern 51. In the example embodiment, engagement surface 54 is shaped like a washer and is directly connected to locking screw 50. However, in other embodiments, engagement surface 54 may be a washer or separated element, for example. In some embodiments, engagement surface 54 may be conically shaped. Engagement surface 54 may include a relatively planar and/or flat distal surface and/or proximal surface. In various embodiments, a proximal end of set screw 50 may include an aperture having an internal threaded surface 52. For example, a cylindrical shaped proximal end may include an aperture having a thread pattern disposed on an internal circumferential surface of the cylindrical shaped proximal end. In the example embodiment, a first drive feature 53a and a second drive feature 53b may be disposed adjacent to and distally with respect to a proximal most end of set screw 50. Additionally, first and second drive features 53a, 53b may be disposed proximally with respect to engagement surface 54. In the example embodiment, drive features 53a, 53b take a hexalobular shape, although various other shapes such as hexaganol, polygonal, torx, etc. are also contemplated. In some embodiments, a surgical drive tool having a corresponding socket may be coupled to drive features 53a, 53b to cause rotation of locking screw 50. Similarly, in some alternative embodiments, a drive tool with a protruding threaded member having a thread pattern with a corresponding size and shape to internal threaded surface 52 may also cause rotation of set screw 50.

As seen best in FIG. 9, set screw 50 may also include a break-off location 55, for example. In the example embodiment, break-off location 55 is disposed directly between drive features 53a, 53b and is designed to shear off when a sufficient rotational force is applied to a proximal end of set screw 50 while a distal end of set screw 50 is stationary, e.g., when set screw 50 is secured in a locked position and a continued rotational force (torque) is applied to the proximal end of set screw 50 the drive feature 53a and cylindrical end having the internal threaded surface 52 may break-off. As also seen best in FIG. 9, the inferior endplate 20 may include a first relief 40a and a second relief 40b on opposite sides of hinge member 40. The first relief 40a may have a size and shape corresponding to a size and shape of a first portion 12a of superior endplate 10 and the second relief 40b may have a size and shape corresponding to a size and shape of a second portion 12b of superior endplate 10, for example. In various embodiments, portions 12a, 12b may comprise a hook shape, outdent, and/or protrusion, for example. In the example embodiment, portions 12a, 12b may be disposed on opposite sides of channel 12 and cup hinge member 40 such that the superior endplate 10 and inferior endplate 20 may rotate relative to one another without becoming uncoupled.

Figure 10:
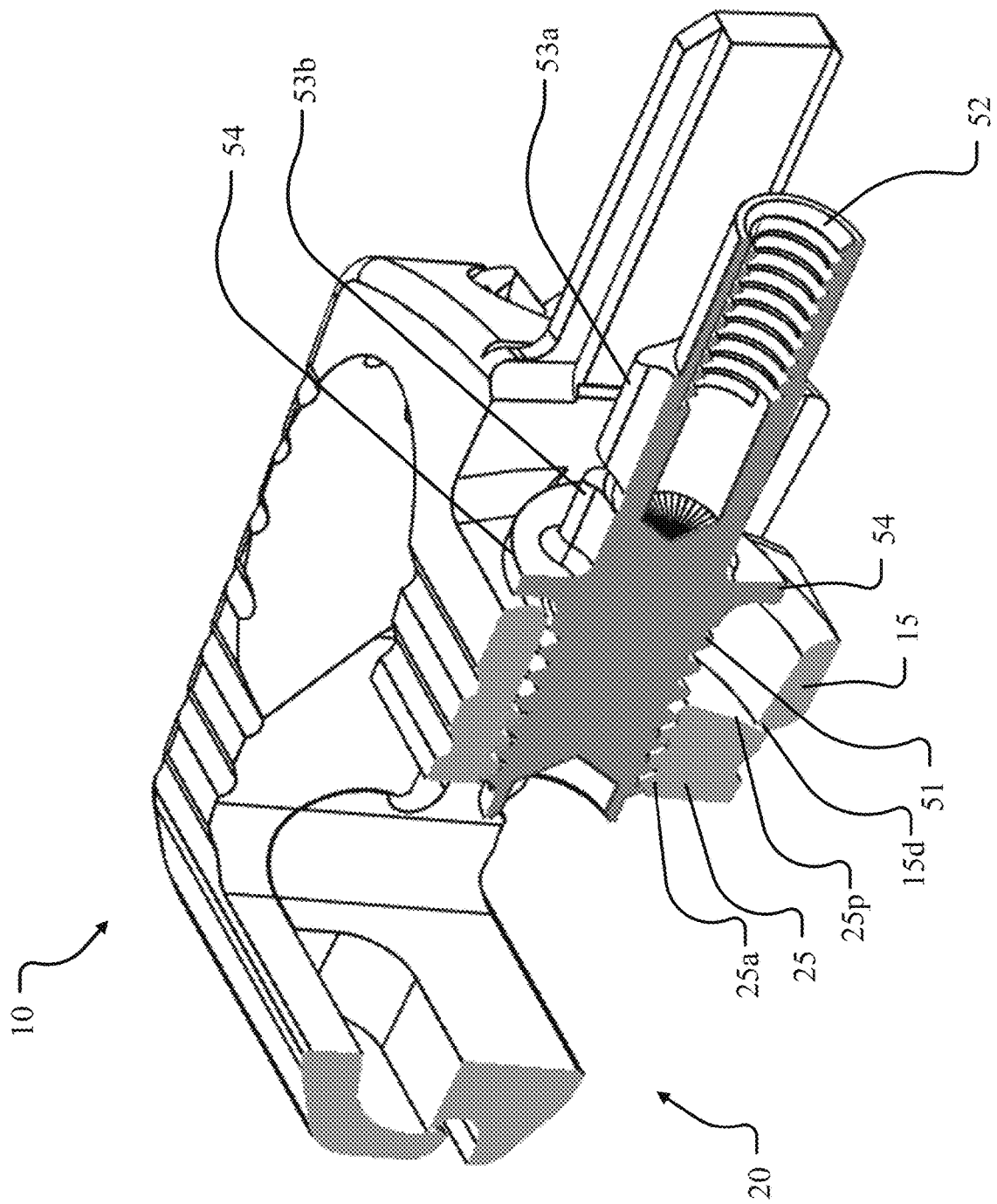
FIG. 10 is a perspective cross section view of an expandable implant.
Figure 11:
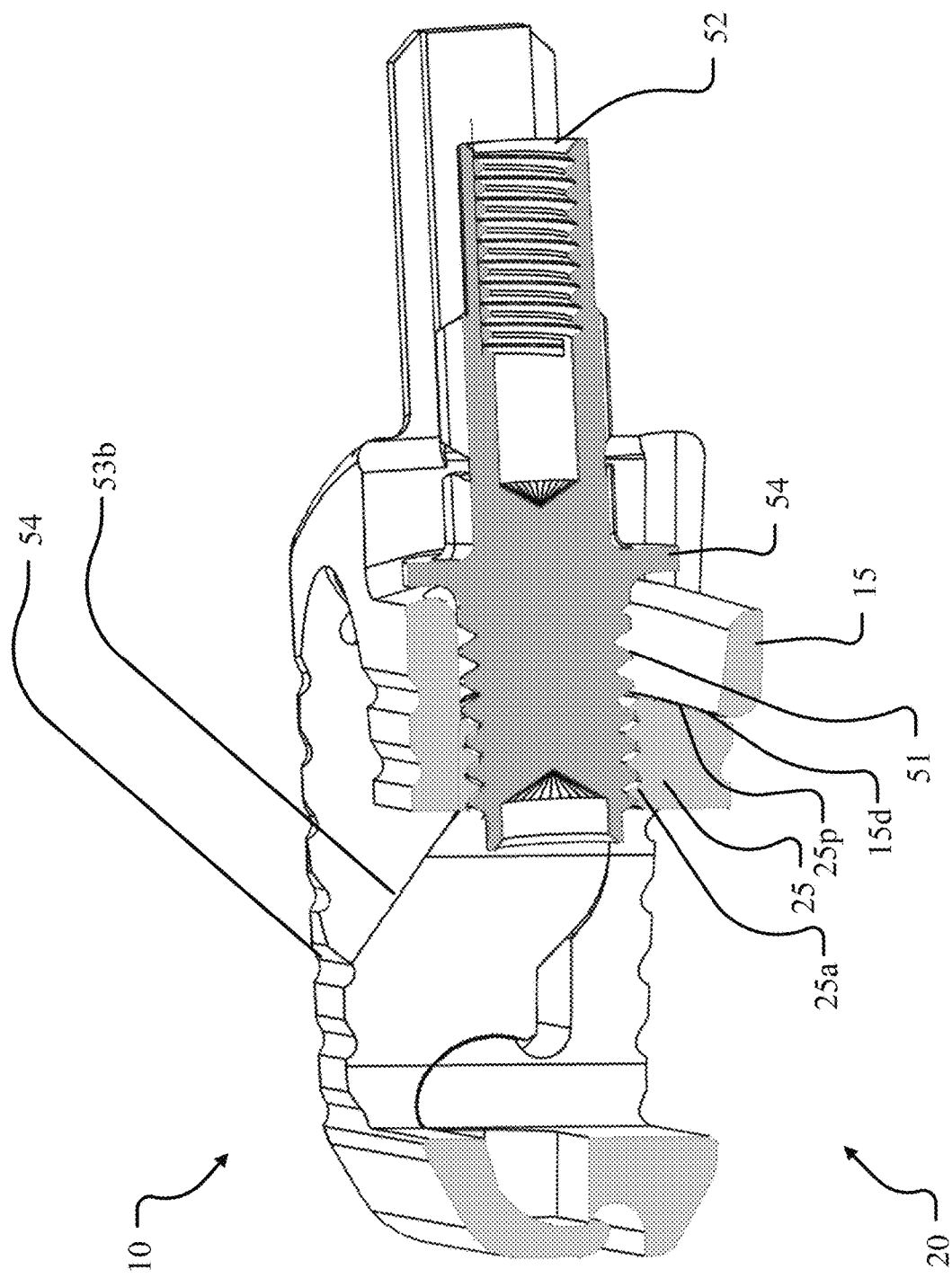
FIG. 11 is a cross section view of an expandable implant.

FIG. 10 is a perspective cross section view and FIG. 11 is a cross section view of expandable implant 100. In the example embodiment, the superior endplate 10 and inferior endplate 20 are coupled together by hinge member 40, and core 25 may be positioned behind of core 15, e.g., core 25 may be positioned distally with respect to core 15. Additionally, the outside external thread pattern 51 of locking screw 50 may engage with the threaded aperture 25a of the core 25 and extend through aperture 15a of core 15. In this way, when locking screw 50 is rotated, the distal surface 15d of core 15 may engage with the proximal surface 25p of core 25. For example, by tightening locking screw 50 the engagement surface 54 of locking screw 50 pushes against the proximal surface 15p of core 15 thereby bringing the superior endplate 10 and inferior endplate 20 into frictional engagement.

Figure 12:
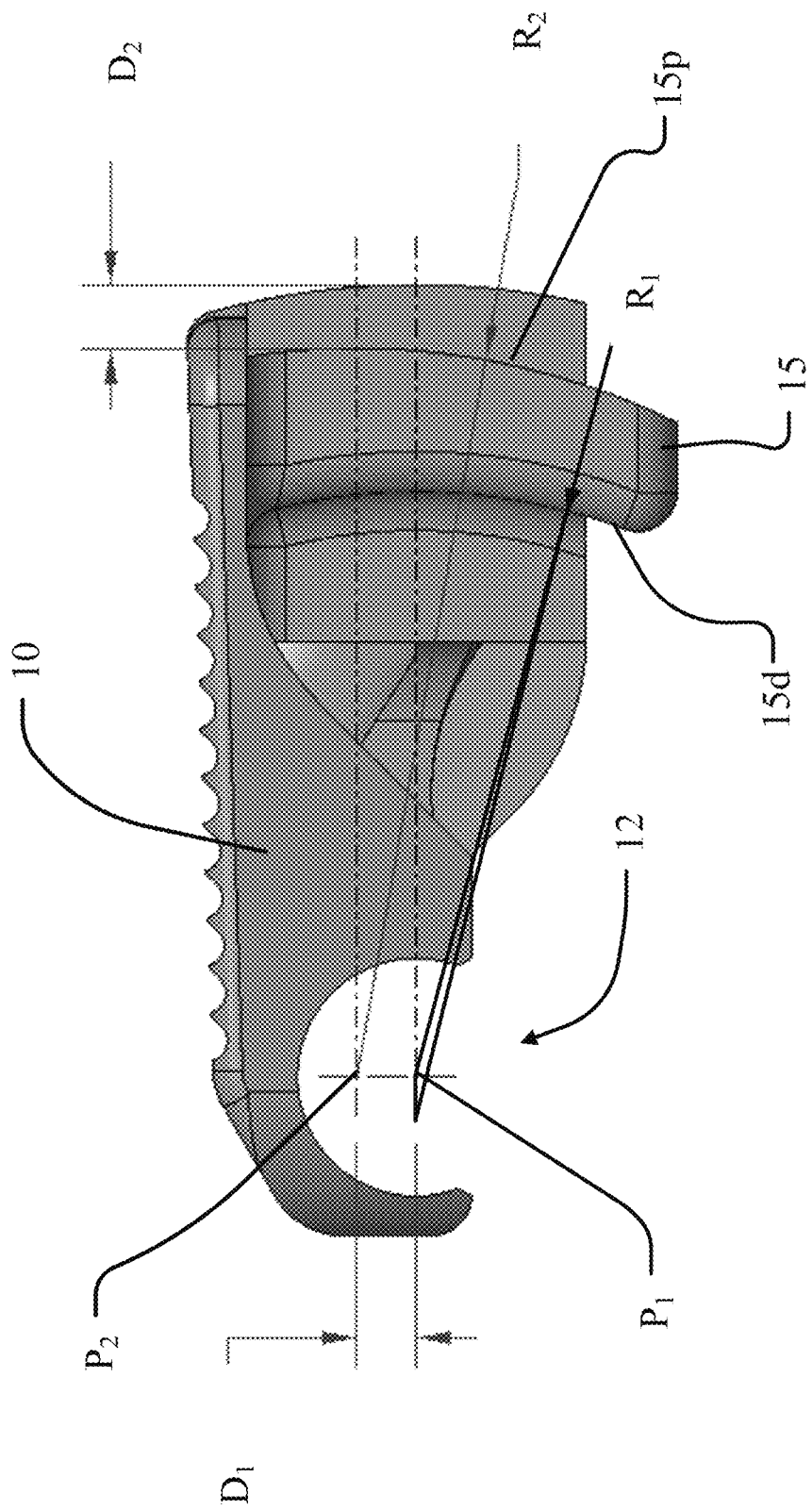
FIG. 12 is a side view of a superior endplate for use with at least some expandable implant embodiments.

FIG. 12 is a side view of a superior endplate 10 for use with at least some expandable implant 100 embodiments. In the example embodiment, superior endplate 10 may include an arcuate channel 12 of which the hinge member 40 may be disposed inside of. In various embodiments, arcuate channel 12 may be defined by a first circle having a center point at $P_1$ and/or a segment of the circle having the center point at $P_1$. The center point $P_1$ may define an axis of rotation that superior endplate 10 may rotate and/or pivot with respect to inferior endplate 20. For example, superior endplate 10 may be hingedly coupled to hinge member 40 as explained above and rotatable about an axis of rotation defined by center point $P_1$, for example. Additionally, in various embodiments a distal surface 15d of core 15 may be a curved surface defined (in part or in total) by a second circle having a center point at $P_1$ and a radius $R_1$. The proximal surface 15p of core 15 may also be a curved surface defined (in part or in total) by a segment of a circle having a radius $R_2$ and a center point $P_2$. In the example embodiment, $P_2$ is located a distance $D_1$ above point $P_1$ and radius $R_2$ is greater than radius $R_1$. Additionally, the proximal surface 15p of core 15 is offset a distance $D_2$ from the proximal most face of the superior endplate 10. In the example embodiment, center point $P_2$ is vertically above center point $P_1$ however, in other embodiments, center point $P_2$ may be offset by a greater amount or even a lesser amount than illustrated. In some examples, $P_2$ may not be aligned vertically above $P_1$. In various embodiments, $R_1$ may be about 7-9 mm+/− about 1 mm and $R_2$ may be about 8-10 mm+/− about 1 mm although these numbers may be modified in some embodiments having a larger or smaller footprint. In various embodiments $D_1$ is about 0.25 mm to about 1.0 mm and $D_2$ is about 0.25 mm to about 1.25 mm. In at least one embodiment, $D_1$ is about 0.75 mm and $D_2$ is about 0.8 mm and $R_2$ is about 9.2 mm.

The above explained geometrical relationship between the offset center points $P_1$ and $P_2$ and $R_1$ and $R_2$ may have several advantages in terms of operability and functionality. At least one advantage is that the superior endplate 10 may have a natural tendency to apply a force against the engagement surface 54 of locking screw 50 such that locking screw 50 may function similar to a wedge preventing implant 100 from fully collapsing. Another advantage is that a biasing force may be applied that naturally urges the superior endplate 10 and inferior endplate 20 into an expanded position which may assist with expanding the implant 100 when positioned between a superior vertebrae and an inferior vertebrae, for example. For example still, an end user such as a surgeon may expand implant 100 and the offset arrangement explained above may facilitate the function of keeping implant 100 lordosed at the chosen angle.

Figure 13B:
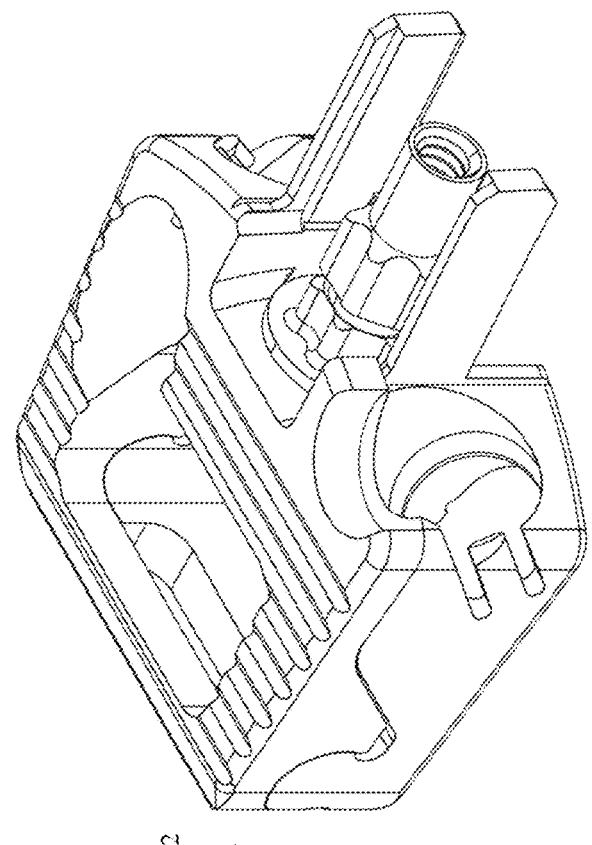
FIG. 13B is a perspective view of a second expandable implant.
Figure 13A:
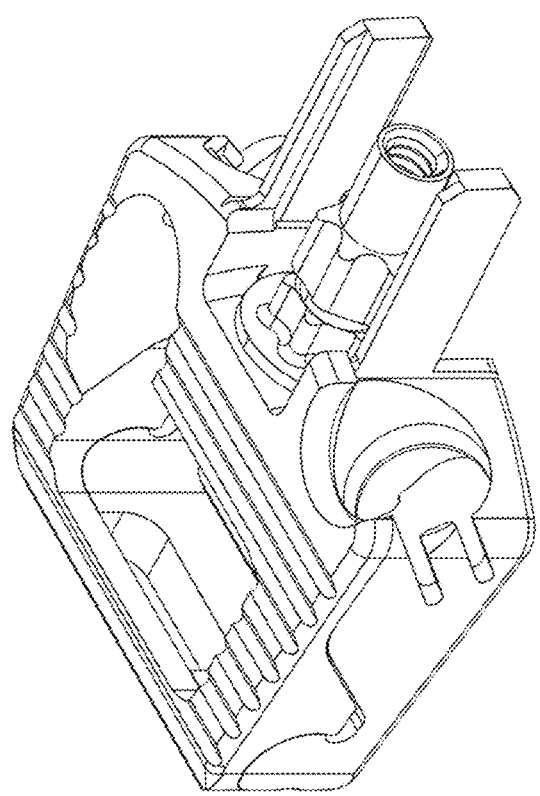
FIG. 13A is a perspective view of a first expandable implant.
Figure 14B:
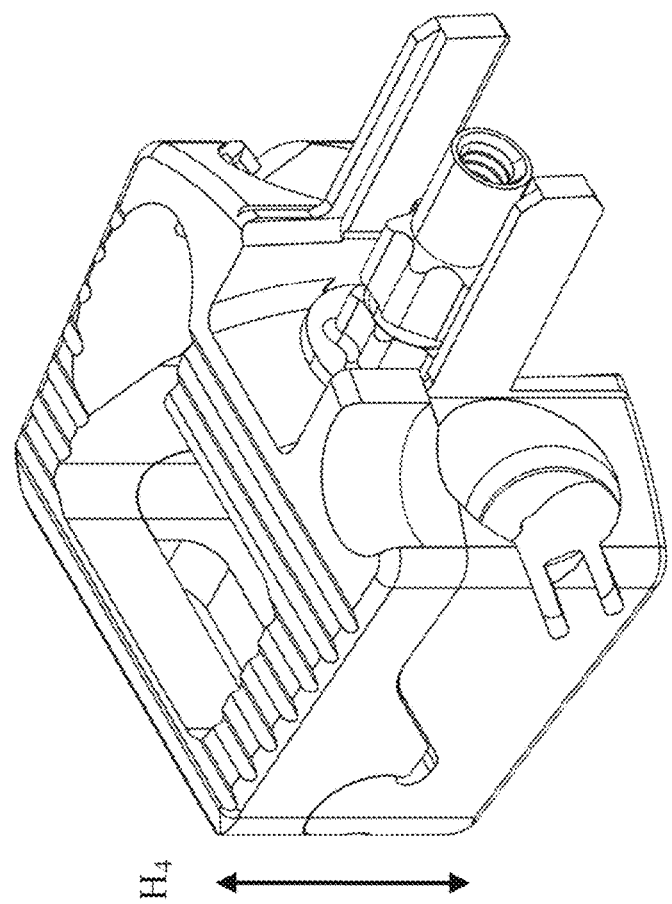
FIG. 14B is a perspective view of a fourth expandable implant.
Figure 14A:
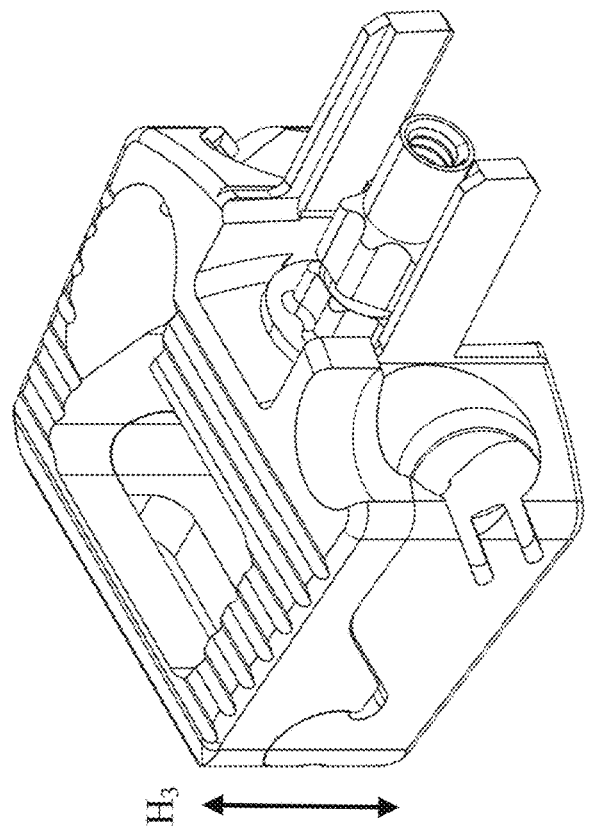
FIG. 14A is a perspective view of a third expandable implant.
Figure 15:
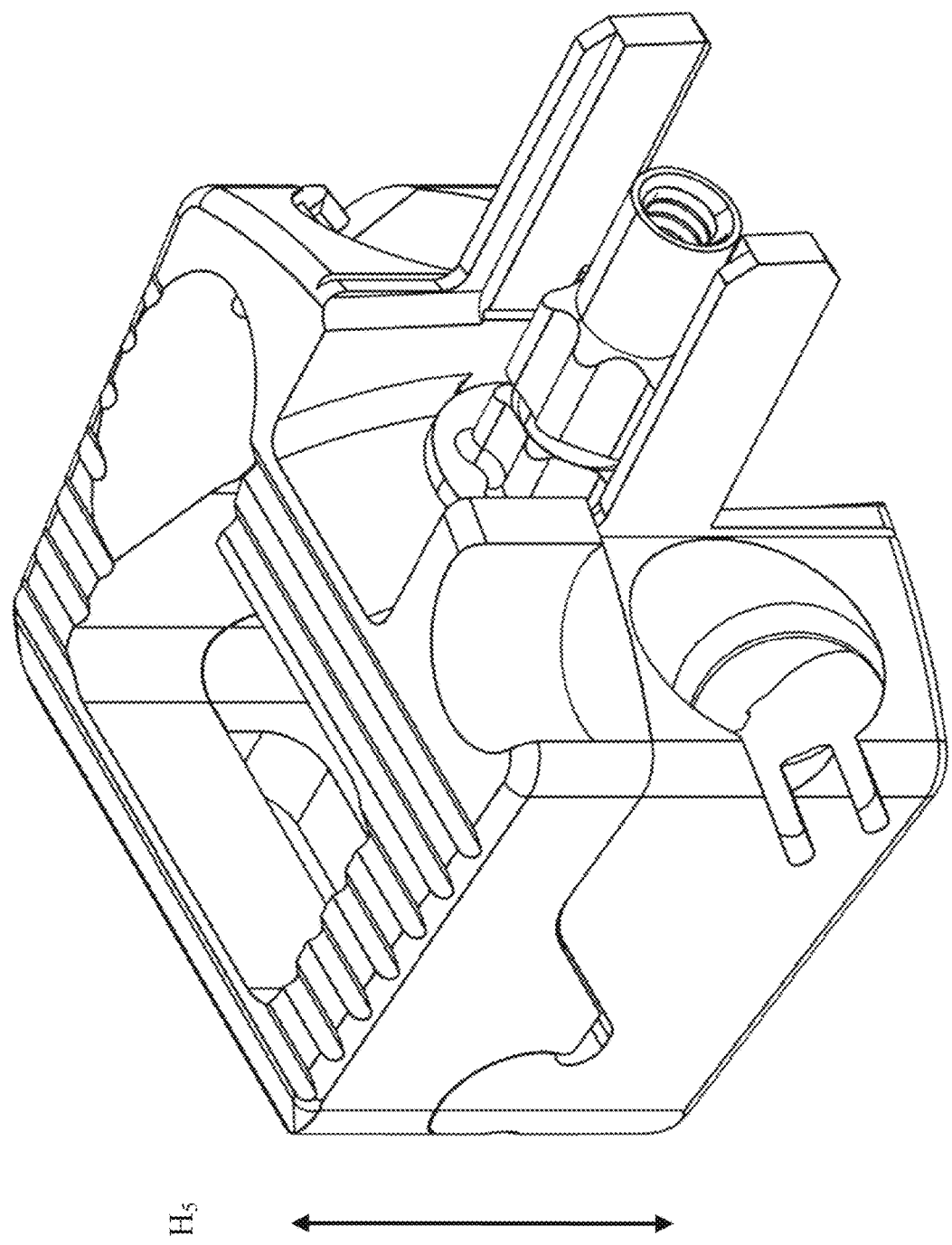
FIG. 15 is a perspective view of a fifth expandable implant.

FIG. 13A is a perspective view of a first expandable implant, FIG. 13B is a perspective view of a second expandable implant, FIG. 14A is a perspective view of a third expandable implant, FIG. 14B is a perspective view of a fourth expandable implant, and FIG. 15 is a perspective view of a fifth expandable implant. In the series of illustrations it is shown that various embodiments in accordance with the principles of this disclosure may be variously sized depending on the particular location in a human body and the particular patient specific human anatomy. For example, FIG. 13A illustrates a first expandable implant 100 having a first height $H_1$ or thickness between the superior endplate 10 and inferior endplate 20, FIG. 13B illustrates a second expandable implant 100 having a second height $H_2$ or thickness, FIG. 14A illustrates a third expandable implant 100 having a third height $H_3$ or thickness, FIG. 14B illustrates a fourth expandable implant 100 having a fourth height $H_4$ or thickness, and FIG. 15 illustrates a fifth expandable implant 100 having a fifth height $H_5$ or thickness. In at least some embodiments, $H_1$ may be about 5 mm, $H_2$ may be about 6 mm, $H_3$ may be about 7 mm, $H_4$ may be about 8 mm, $H_5$ may about 9 mm, for example. In various embodiments, an angle of inclination between the superior endplate 10 and inferior endplate 20 may be about 4 degrees to about 15 degrees in an expanded configuration, e.g., an angled and/or inclined configuration.

Figure 16:
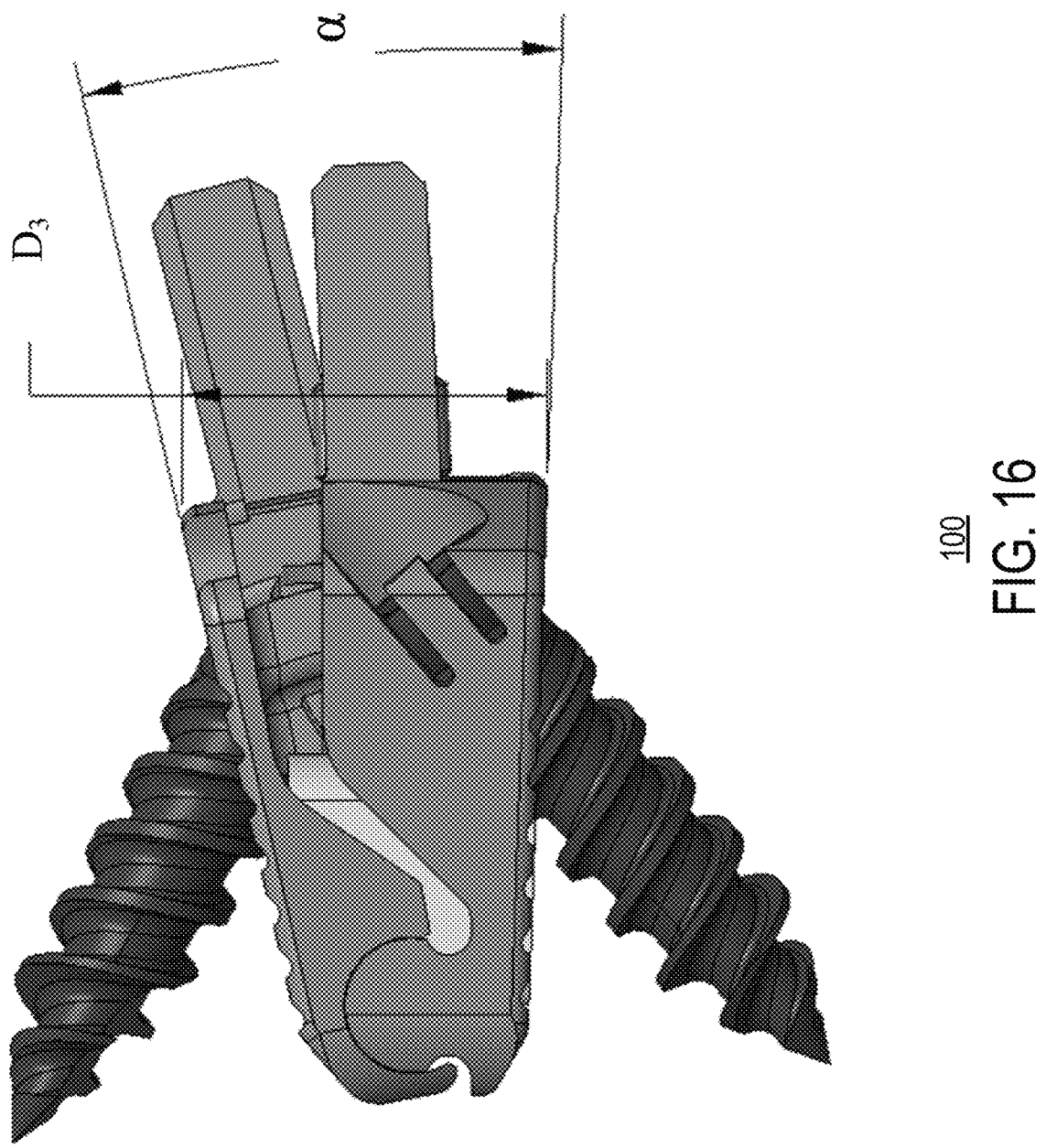
FIG. 16 is a side view of an expandable implant in the expanded configuration.

FIG. 16 is a side view of an expandable implant 100 in the expanded configuration. In an expanded position, a distance $D_3$ between the superior endplate 10 and inferior endplate 20 at the proximal end 100P may be relatively greater than in the closed configuration, for example. Additionally, an angle of inclination a may be relatively greater in an expanded position than in the closed configuration, for example. In this embodiment, implant 100 may have a height $H_1$ corresponding to FIG. 13A and be about 5 mm in a closed configuration. In the illustrated expanded configuration of FIG. 16, $D_3$ may be about 8 mm to 9 mm and a may be about 10 degrees to about 20 degrees. In at least one embodiment, $D_3$ may be 8 mm in a fully expanded position and a may be about 15 degrees, for example.

Figure 17:
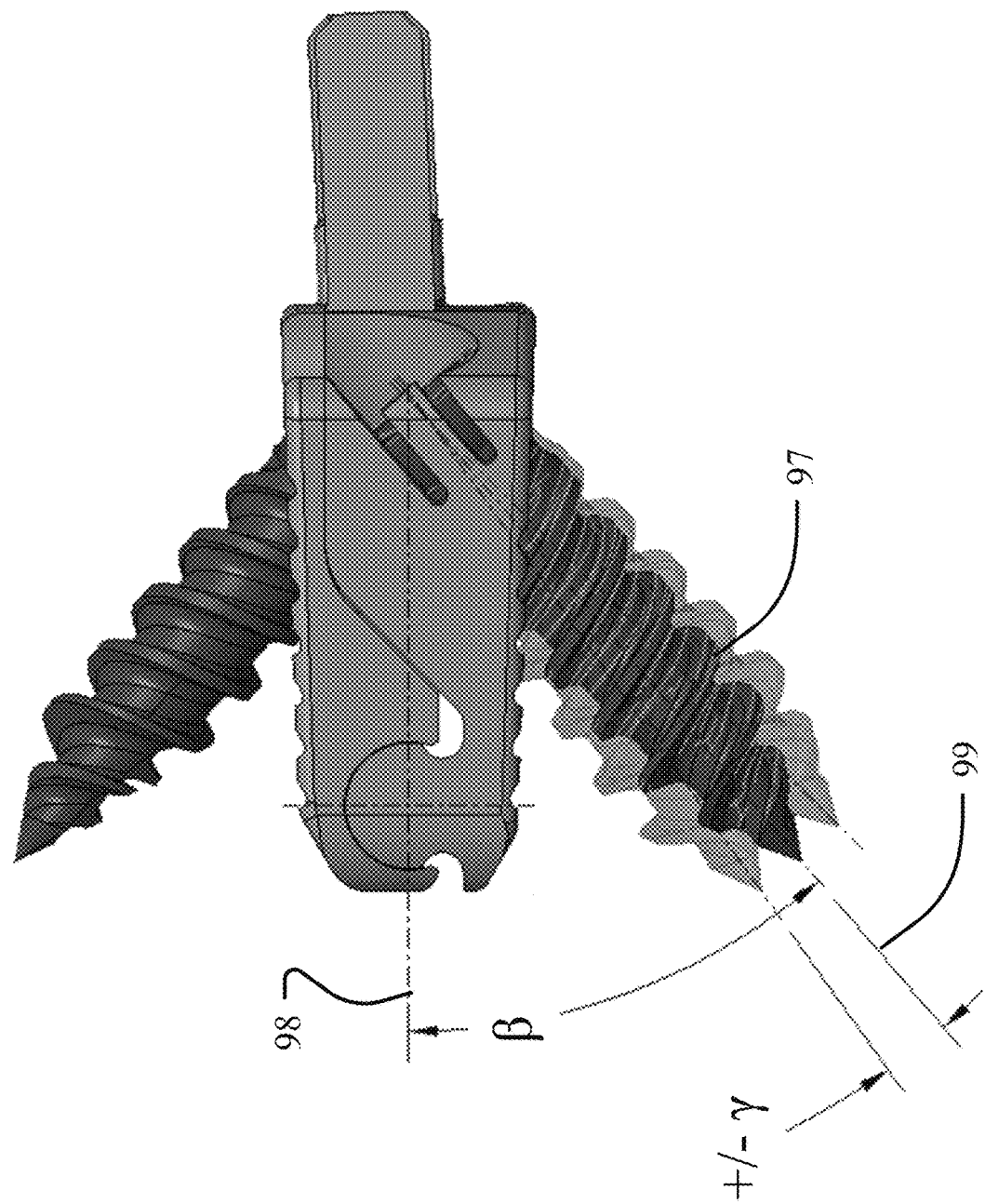
FIG. 17 is a side view of an expandable implant showing a bone screw trajectory.

FIG. 17 is a side view of an expandable implant 100 showing a bone screw trajectory 99. In the example embodiment, it is shown that a centered bone screw trajectory 99 of bone screw 97 is at an angle β with respect to a plane 98 that crosses through a center of the implant from a first lateral side to a second lateral side, for example. Additionally, the bone screw trajectory 99 may be varied +/− by a degree γ, for example. In various embodiments, β may be about 30 degrees to about 50 degrees and γ may be about 2 degrees to about 10 degrees. In the example embodiment, β may be about 40 degrees and γ may be about 5 degrees.

Figure 18:
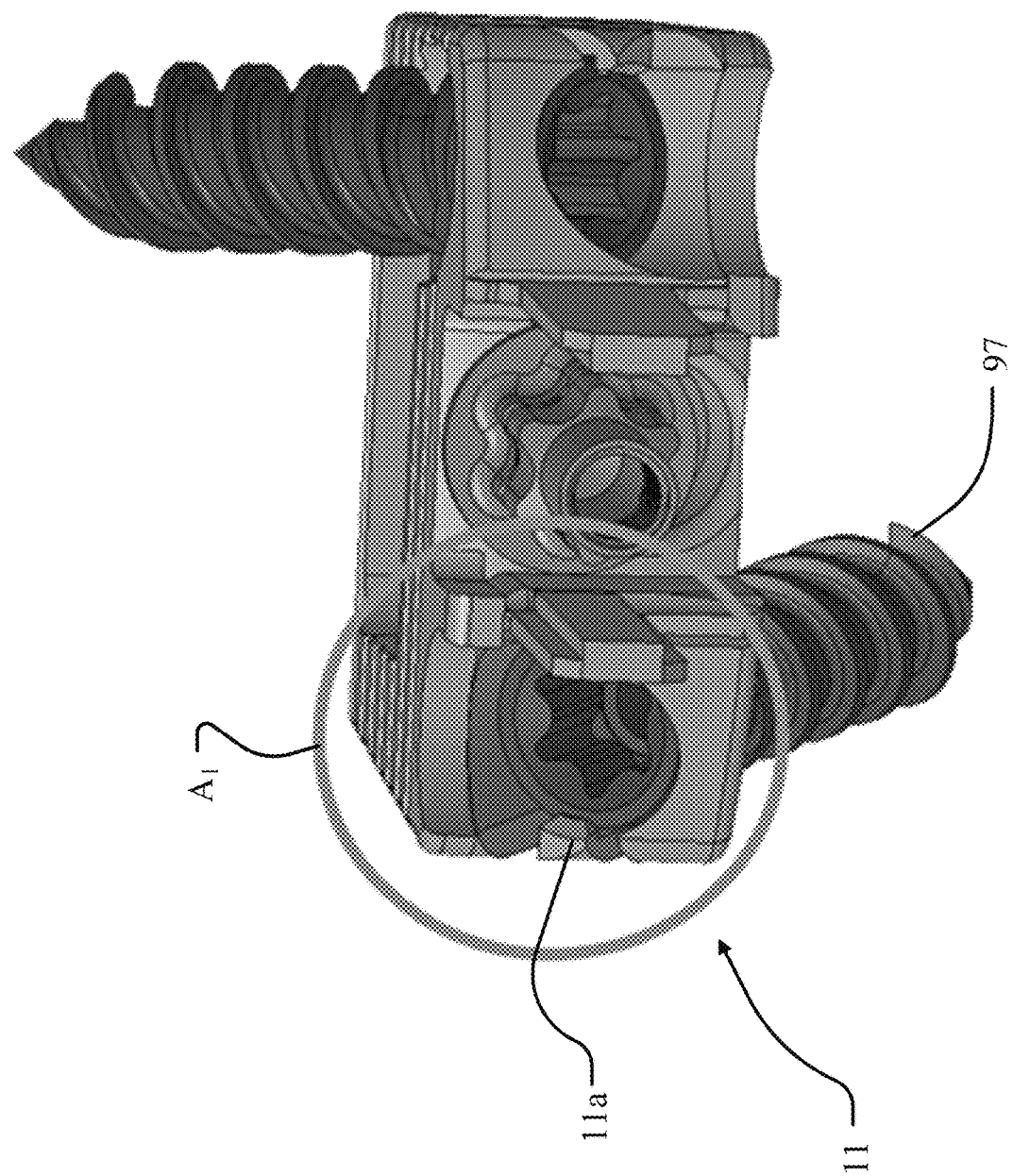
FIG. 18 is a front view of an expandable implant.
Figure 19:
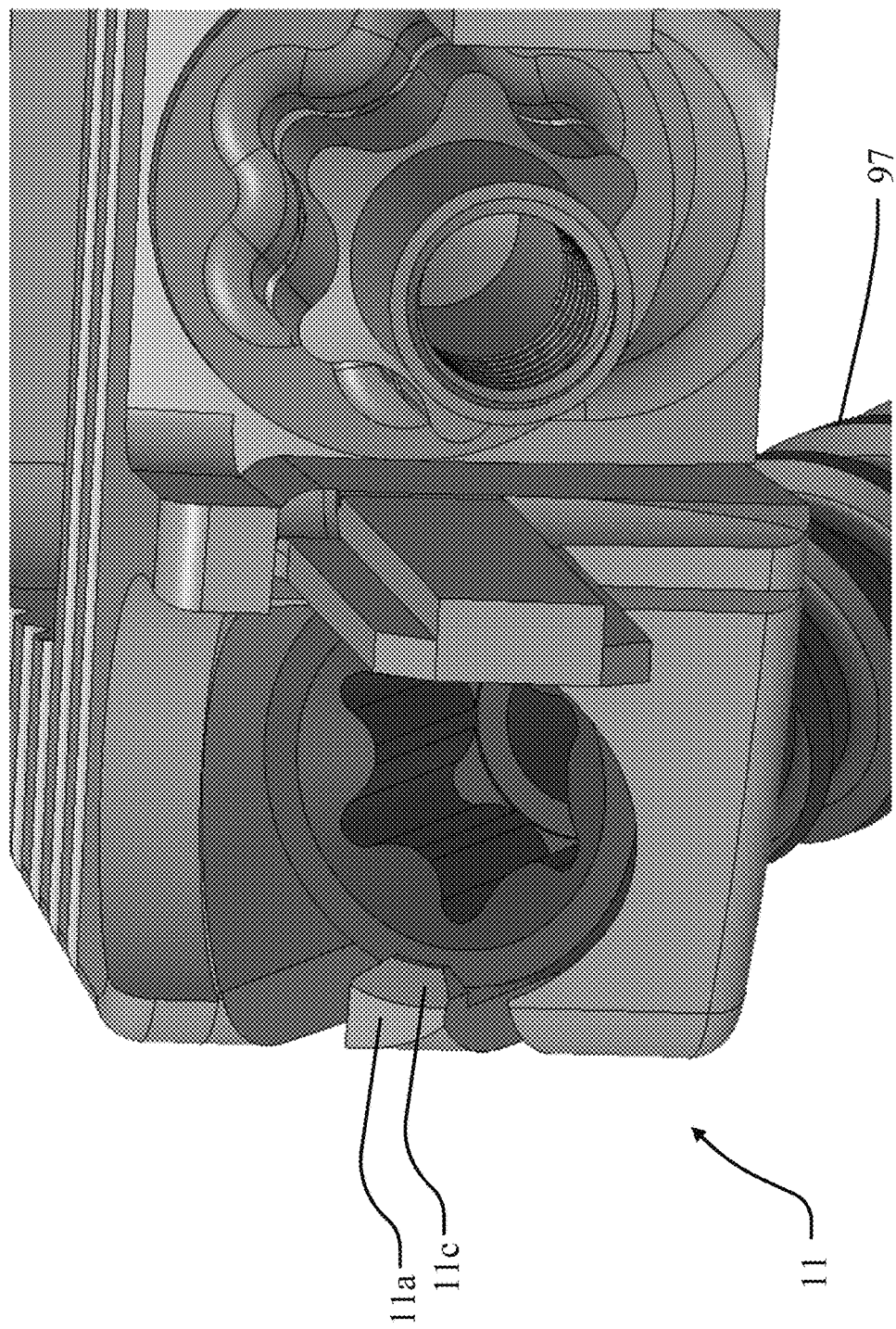
FIG. 19 is a front view of an enlarged area of FIG. 18.
Figure 20:
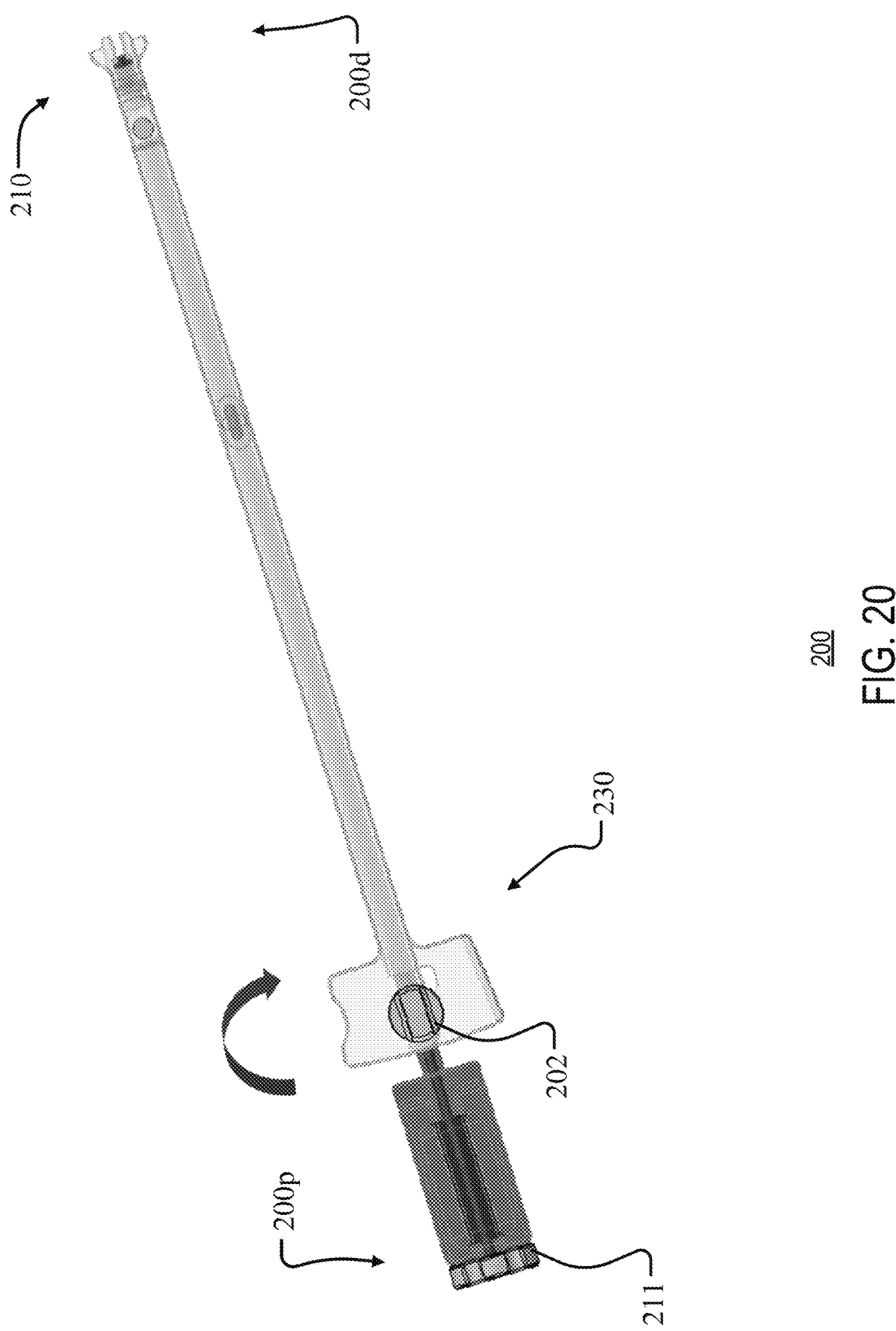
FIG. 20 is a perspective view of an inserter for use with disclosed expandable implants.
Figure 21:
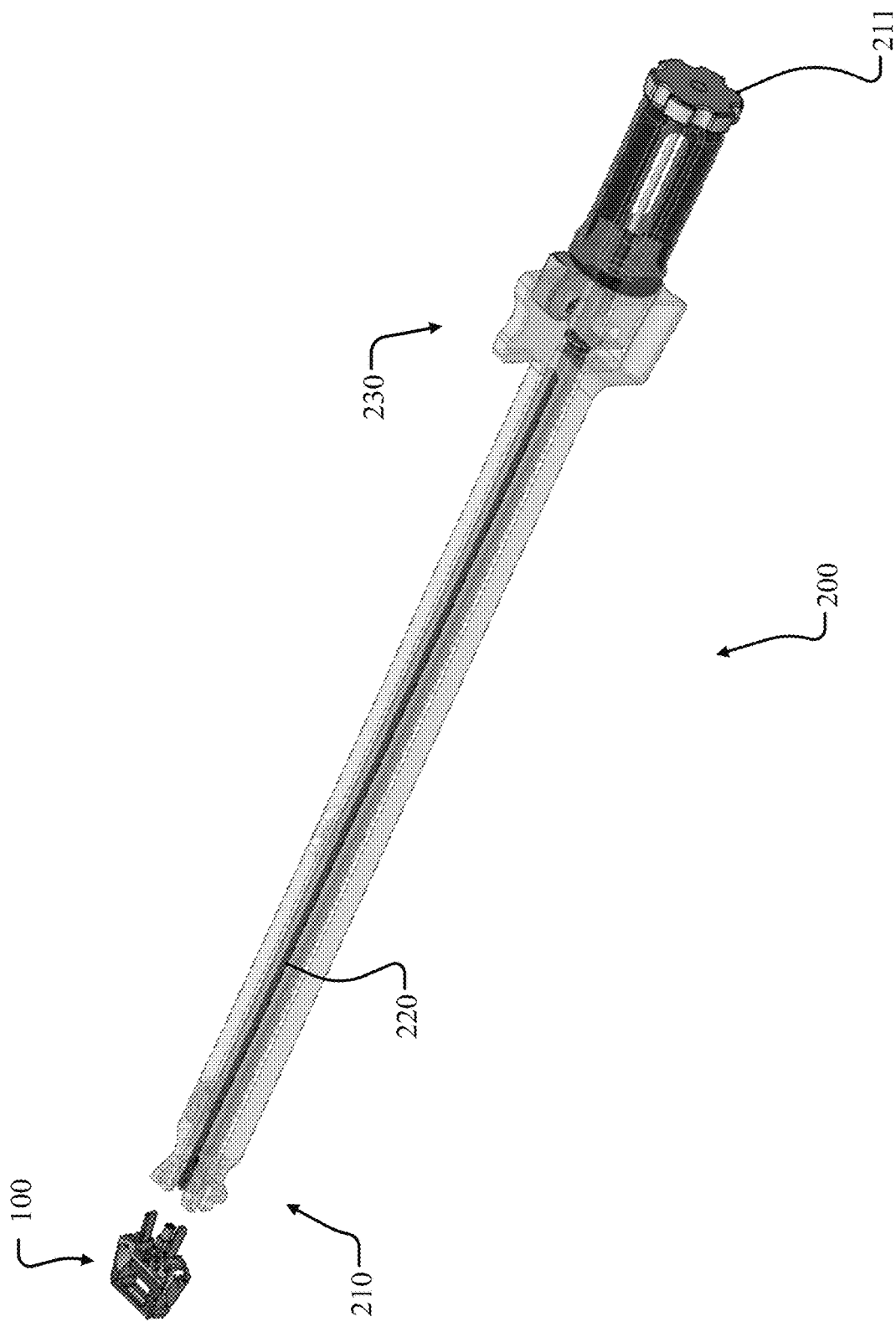
FIG. 21 is a perspective view of an inserter for use with disclosed expandable implants shown in skeleton outlining for ease of understanding.
Figure 22:
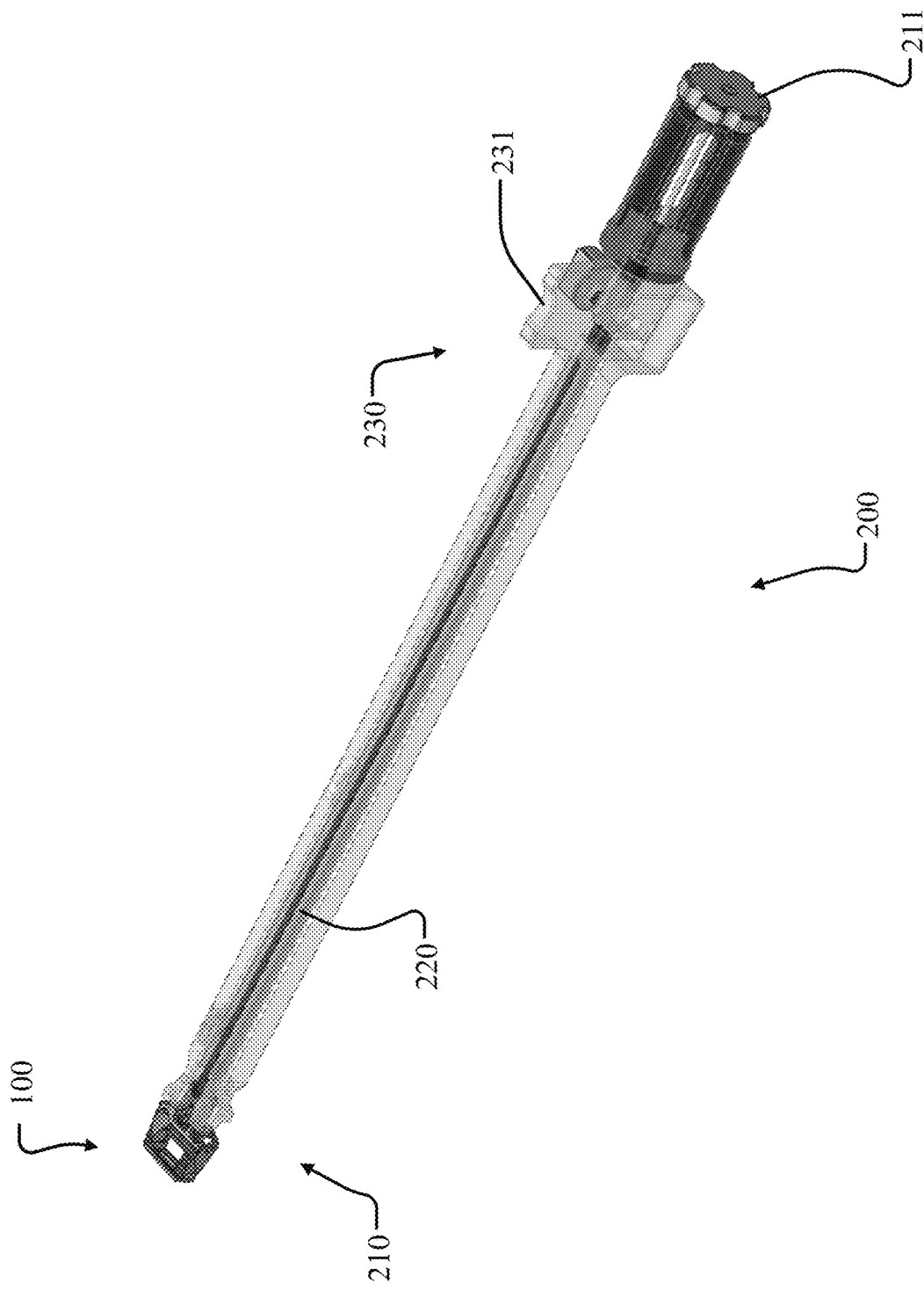
FIG. 22 is a perspective view of an inserter for use with disclosed expandable implants shown in skeleton outlining for ease of understanding.
Figure 23:
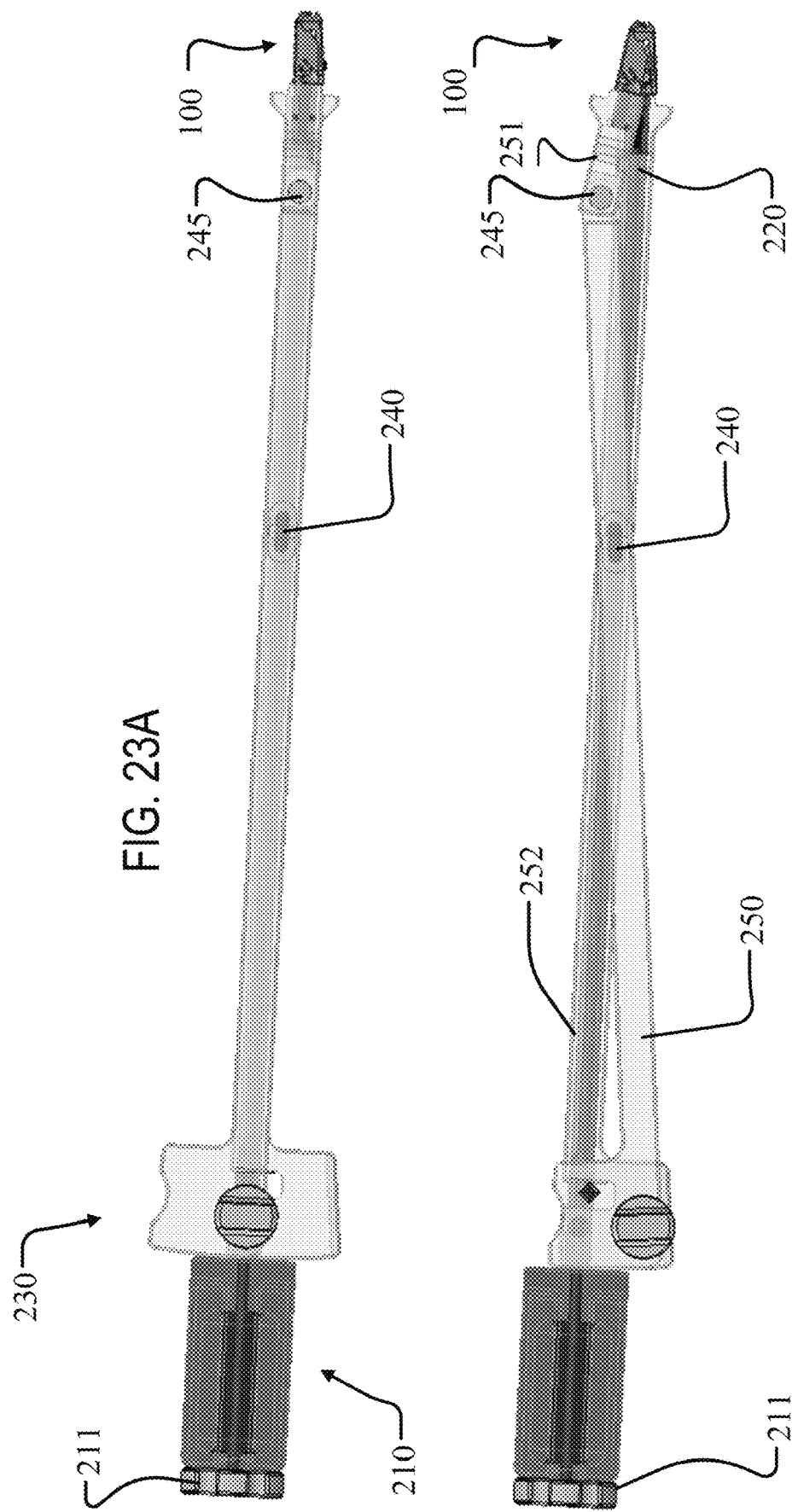
FIG. 23A is a rear view of an inserter in a non-expanded position.
FIG. 23B is a rear view of an inserter in an expanded position.
Figure 24:
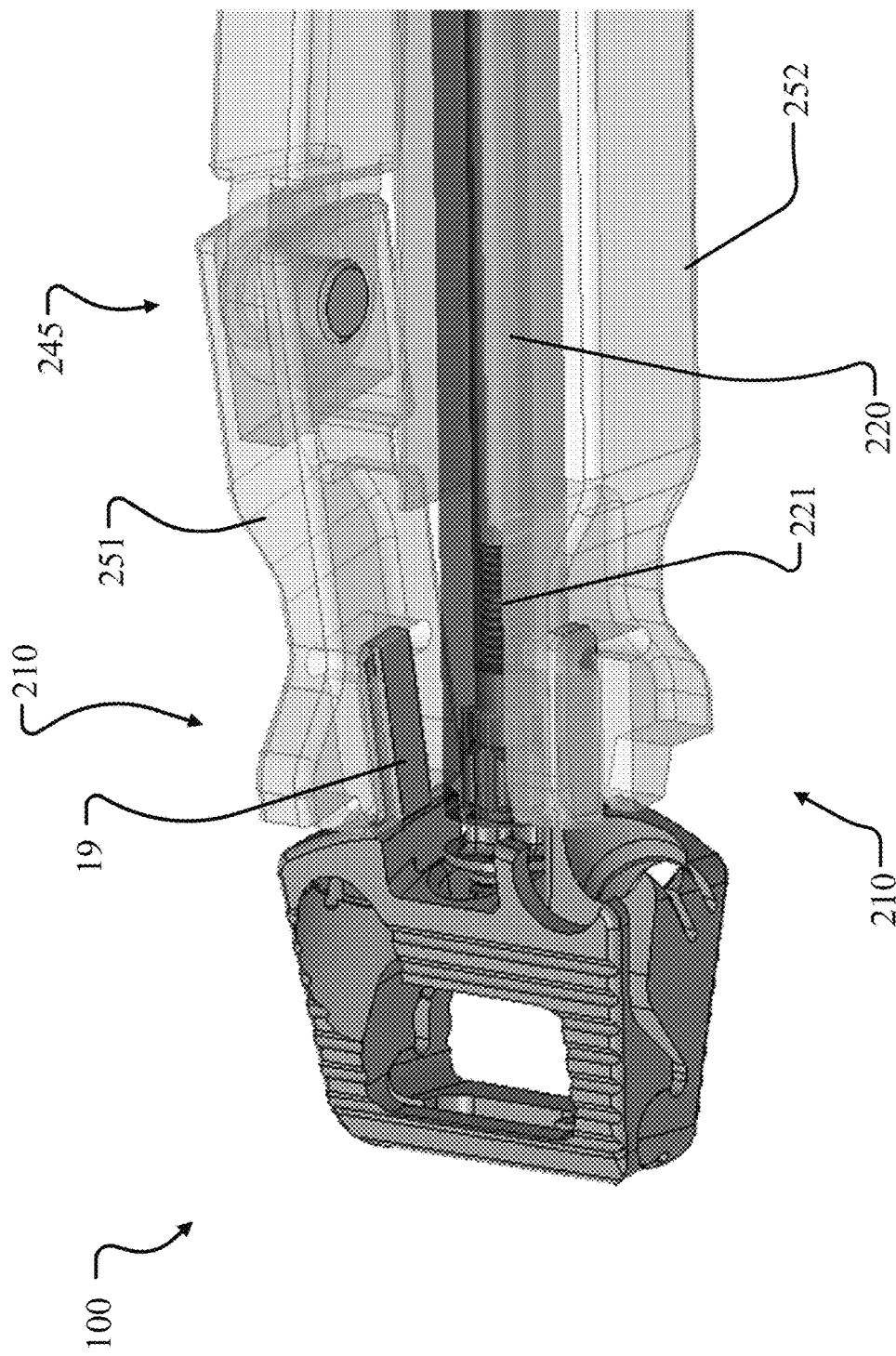
FIG. 24 is an enlarged view of a distal end of an inserter in an expanded position coupled to an example expandable implant in a corresponding expanded position.

FIG. 18 is a front view of an expandable implant showing an area $A_1$ and FIG. 19 is a front view of an enlarged area $A_1$ of FIG. 18. In the example embodiment, bone screw 97 is in a position extending through bone screw aperture 11 where it cannot backout due to bone screw retention mechanism 11a. The bone screw retention mechanism 11a includes an inclined surface 11c such that when bone screw 97 is being installed, an underside of the head portion of bone screw 97 directly contacts the inclined surface 11c thereby pushing the bone screw retention mechanism 11a laterally outward and away from bone screw aperture 11, for example. Thereafter, when bone screw 97 is installed and the head portion of bone screw 97 is beneath inclined surface 11c the bone screw retention mechanism may flex back towards bone screw aperture 11 such that it will prevent bone screw 97 from backing out, e.g., a blocking surface of bone screw retention mechanism 11a may contact an upper surface of the head portion of bone screw 97. In the example embodiment, bone screw retention mechanism 11a comprises flexible arm (or spring tab) having an inclined surface 11c (or ramp) that is disposed on a lateral end of implant 100 adjacent bone screw aperture 11.

Referring generally to FIGS. 20-24 an inserter 200 for use with disclosed expandable implants 100 is illustrated. Inserter 200 may extend in a longitudinal direction from a proximal end 200p to a distal end 200d, for example. Inserter 200 may include a pair of handles 230, a handle lock 202, and mounting arms 210 for securely coupling to mounting tangs 19, 29 of implant 100, for example. Inserter 200 may further include a tightening knob 211 that is connected to a drive shaft 220 having a drive end 221. Drive end 221 may have a size and shape generally corresponding to a size and shape of the various drive features of locking screw 50, for example the internal threaded surface 52, first drive feature 53a, and/or second drive feature 53b. In the example embodiment shown in FIG. 24, drive end 221 includes an end portion having an outside threaded surface with a corresponding size and shape to the internal threaded surface 52 of locking screw 50. In various embodiments, tightening knob 211 may rotate drive shaft 220 and drive end 221 to engage drive end 221 with locking screw 50 and pull implant 100 towards inserter tool 200 such that mounting tangs 19, 29 are securely nested within corresponding channels of mounting arms 210. Additionally, an end user may rotate inserter 200 thereby translating a rotational force through drive end 221 to locking screw 50, e.g., via first drive feature 53a, and/or second drive feature 53b.

As seen best in FIGS. 23A and 23B, inserter 200 may include a pair of handles 230, a stationary arm 252, a primary pivoting arm 250, and a secondary pivoting arm 251. For example, to expand implant 100 an end user may toggle handle lock 202 to an unlocked position and push down on thumb indentation 231 of the handle 230 that is connected to the primary pivoting arm 250 and secondary pivoting arm 251. In doing so, primary pivoting arm 250 may pivot with respect to medial pivot point 240 and secondary pivoting arm 251 may pivot with respect to distal pivot point 245, for example. The path of travel of secondary pivoting arm 251 may lift up on the corresponding mounting tang 19 or 29 and cause the superior endplate 10 and inferior endplate 20 to separate from one another at the proximal end, for example. In doing so, an end user can lordose implant 100 to a desired angle. For example, as seen best in FIG. 24, secondary pivoting arm 251 has lifted up on mounting tang 19, which is nested in a corresponding channel of mounting arm 210.

Once implant 100 is lordosed to a desired configuration, an end user may rotate drive shaft 220 and drive end 221 to tighten locking screw 50 as explained previously. After locking screw 50 is relatively tight, the end user may continue to apply a rotational force to locking screw 50 until a proximal portion comprising the cylindrical part having an internal threaded surface 52, and the first drive feature 53a breaks off at break-off location 55. For example, once locking screw 50 is tightened to a designed torque, the locking screw 50 may shear off as explained previously. At least one advantage of utilizing the locking screw 50, is that it may prevent over tightening which can cause deformation to implant 100. As shown in FIG. 25, implant 100 has been expanded to a desired position and/or lordotic angle. Additionally, locking screw 50 has locked the relative position of the superior endplate 10 with respect to the inferior endplate 20 and the proximal portion of locking screw 50 has been broken off as explained above.

FIGS. 26 and 27 are various views of a surgical instrument 300 for use with disclosed expandable implants 100. In some embodiments, surgical instrument 300 may be referred to as a break-off instrument and may be used to break-off the mounting tangs 19, 29 of implant 100. In the example embodiment, surgical instrument 300 comprises a first instrument 310 and a second instrument 320. First instrument 310 may extend in a longitudinal direction from handle 312 towards gripping end 311. Similarly, second instrument 320 may extend in a longitudinal direction from handle 322 to gripping end 321. Gripping ends 311, 321 may comprise a channel having a size and shape generally corresponding to mounting tangs 19, 29. For example, as seen best in FIG. 27, the mounting tangs 19, 29 may be insert inside of the corresponding channels of gripping ends 311, 321. After the mounting tangs 19, 29 are nested within gripping ends 311, 321 an end user may push laterally outward and/or inward against handles 312, 322 to break-off the corresponding mounting tang 19, 29. For example, as shown in FIG. 28 expandable implant 100 is in an expanded and lordosed configuration and the proximal portion of locking screw 50 and tangs 19, 29 have been broken off.

Figure 29:
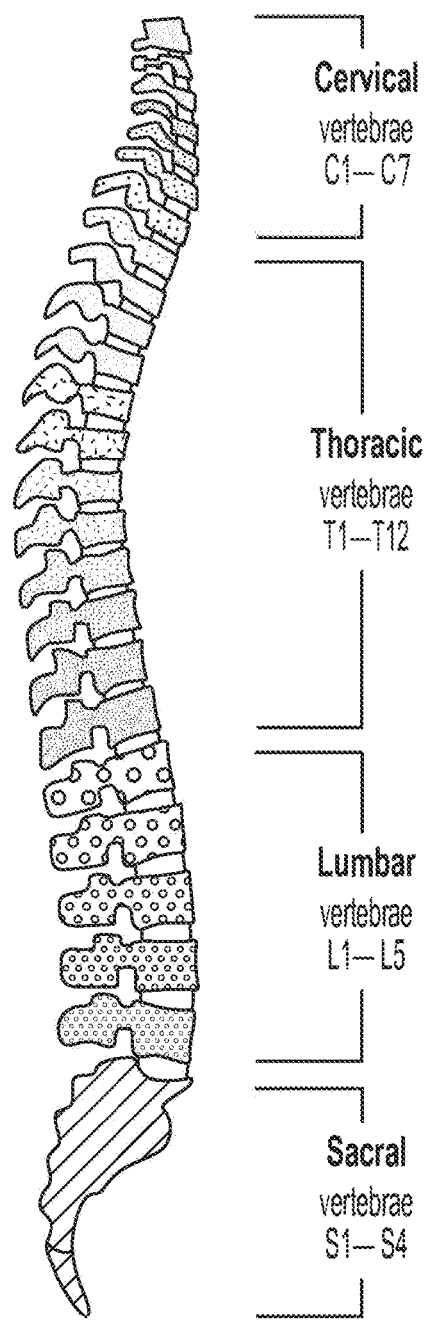
Figure 30:
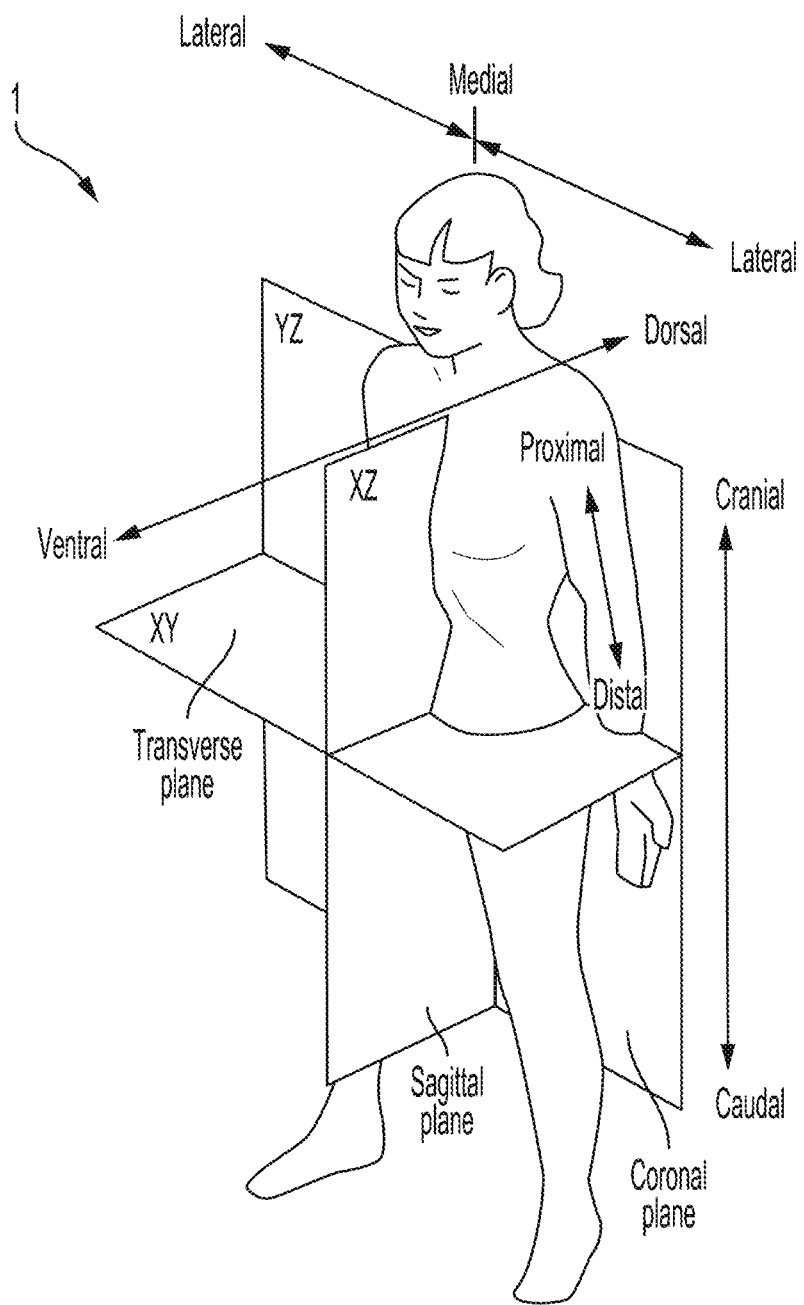
FIG. 30 is a reference drawing showing various planes and reference directions of which the various disclosed implant embodiments may move in or act in with respect to a patient.

FIG. 29 is a reference drawing showing the human spine of which various disclosed implant embodiments may be installed in. FIG. 30 is a reference drawing showing various planes and reference directions of which the various disclosed implant embodiments may move in or act in with reference to a patient 1.

It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

What is claimed is:

1. An expandable implant movable between a contracted position and an expanded position, comprising:
   an expandable body extending from a proximal end to a distal end in a proximal-to-distal direction and extending from a first lateral side to a second lateral side in a widthwise direction, the expandable body being defined by a superior endplate and an inferior endplate opposite the superior endplate; wherein the superior endplate comprises: a channel located adjacent a distal end of the superior endplate and extending in the widthwise direction; and a first core integrally formed with the superior endplate and having a distal engagement surface; wherein the inferior endplate comprises: a rail located adjacent a distal end of the inferior endplate and extending in the widthwise direction, the rail being integrally formed with the inferior endplate and having a size and shape generally corresponding to a size and shape of the channel and being located within the channel; and a second core integrally formed with the inferior endplate and having a proximal engagement surface and a threaded screw aperture; and a threaded locking screw disposed in the threaded screw aperture and movable between a locked position and an unlocked position, wherein, when moving from a contracted position to an expanded position the rail rotates within the channel, and wherein, in the locked position, the threaded locking screw urges the distal engagement surface of the first core into direct contact with the proximal engagement surface of the second core.

2. The expandable implant of claim 1, wherein:
   the superior endplate comprises a first mounting tang extending from a proximal end of the superior endplate; and
   the inferior endplate comprises a second mounting tang extending from a proximal end of the inferior endplate,
   wherein the first mounting tang is disposed opposite the second mounting tang.

3. The expandable implant of claim 2, wherein:
   the first mounting tang comprises a first break-off location; and
   the second mounting tang comprises a second break-off location.

4. The expandable implant of claim 1, wherein:
   the superior endplate comprises a first bone screw aperture disposed on a proximal end of the superior endplate; and
   the inferior endplate comprises a second bone screw aperture disposed on a proximal end of the inferior endplate.

5. The expandable implant of claim 1, wherein:
   the channel located adjacent the distal end of the superior endplate extends in the widthwise direction from the first lateral side to the second lateral side; and
   the rail located adjacent the distal end of the inferior endplate extends in the widthwise direction from the first lateral side to the second lateral side.

6. The expandable implant of claim 5, wherein:
   the superior endplate comprises at least one hook portion adjacent the channel;
   the inferior endplate comprises at least one relief portion adjacent the rail;
   the at least one hook portion has a size and shape generally corresponding to a size and shape of the at least one relief portion; and
   the at least one hook portion is disposed within the at least one relief portion.

7. The expandable implant of claim 6, wherein the channel comprises an arcuate shape-arcuate cross-section and the rail comprises an arcuate cross-section.

8. The expandable implant of claim 1, wherein the first core is disposed proximally with respect to the second core and the threaded locking screw extends through the first core.

9. The expandable implant of claim 1, wherein the threaded locking screw comprises a break-off portion.

10. The expandable implant of claim 1, wherein the threaded locking screw comprises an interior having an exposed circumferential surface including a thread pattern.

11. The expandable implant of claim 1, wherein the implant is expandable via a first mounting tang disposed on a proximal end of the superior endplate and a second mounting tang disposed on a proximal end of the inferior endplate.

12. The expandable implant of claim 1, wherein:
the distal engagement surface of the first core comprises a first curved engagement surface;
the proximal engagement surface of the second core comprises a second curved engagement surface; and
the first curved engagement surface is defined by a radius of a circle having a center point offset from an axis of rotation of the rail.

13. The expandable implant of claim 1, wherein:
the superior endplate comprises a first bone screw aperture disposed on a proximal end of the superior endplate and a first flexible bone screw retention arm for retaining a first bone screw positioned within the first bone screw aperture; and
the inferior endplate comprises a second bone screw aperture disposed on a proximal end of the inferior endplate and a second flexible bone screw retention arm for retaining a second bone screw positioned within the first bone screw aperture.

14. The expandable implant of claim 13, wherein:
the first flexible bone screw retention arm includes a first inclined surface and the second flexible bone screw retention arm includes a second inclined surface.

15. An expandable implant system, comprising:
an inserter tool extending in a lengthwise direction from a proximal end thereof to a distal end thereof, the inserter tool including a drive shaft supporting a drive end adjacent the distal end thereof and a pair of mounting arms adjacent the distal end thereof; and
an expandable implant movable between a contracted position and an expanded position, the expandable implant comprising an expandable body extending from a proximal end to a distal end in a proximal-to-distal direction and extending from a first lateral side to a second lateral side in a widthwise direction, the expandable body being defined by a superior endplate and an inferior endplate opposite the superior endplate;
wherein the superior endplate comprises: a channel located adjacent a distal end of the superior endplate and extending in the widthwise direction; a first mounting tang; and a first core integrally formed with the superior endplate and having a distal engagement surface; wherein the inferior endplate comprises: a rail located adjacent a distal end of the inferior endplate and extending in the widthwise direction, the rail being integrally formed with the inferior endplate and having a size and shape corresponding to a size and shape of the channel and being located within the channel; a second mounting tang; and a second core integrally formed with the inferior endplate and having a proximal engagement surface and a threaded screw aperture; and a threaded locking screw disposed in the threaded screw aperture and movable between a locked position and an unlocked position, wherein, in the locked position, the threaded locking screw urges the distal engagement surface of the first core into direct contact with the proximal engagement surface of the second core, wherein, when moving from a contracted position to an expanded position the rail rotates within the channel, wherein, in an insertion configuration, the first and second mounting tangs of the expandable implant are disposed within the pair of mounting arms of the inserter tool, and wherein the drive end of the inserter tool has a size and shape generally corresponding to a size and shape of a drive end of the threaded locking screw.

16. The system of claim 15, wherein the threaded locking screw comprises a break-off portion.

17. The system of claim 16, wherein the drive end of the inserter tool is configured to shear off the break-off portion of the threaded locking screw.

18. The system of claim 15, wherein:
the first mounting tang extends from a proximal end of the superior endplate; and
the second mounting tang extends from a proximal end of the inferior endplate,
wherein the first mounting tang is disposed opposite the second mounting tang.

19. The system of claim 18, wherein:
the first mounting tang comprises a first break-off location; and
the second mounting tang comprises a second break-off location.

20. The system of claim 19, comprising:
a break-off tool extending in a lengthwise direction from a proximal end thereof to a distal end thereof, the proximal end comprising a handle and the distal end comprising at least one channel for receiving and breaking off at least one of the first mounting tang and second mounting tang.

* * * * *